US010287616B2

(12) United States Patent
Zeng

(10) Patent No.: US 10,287,616 B2
(45) Date of Patent: May 14, 2019

(54) LABEL FREE BIOSENSORS, GRAM-NEGATIVE BACTERIA DETECTION, AND REAL-TIME AND END POINT DETERMINATION OF ANTIBIOTIC EFFECTS

(71) Applicant: Oakland University, Rochester, MI (US)

(72) Inventor: Xiangqun Zeng, Rochester Hills, MI (US)

(73) Assignee: Oakland University, Rochester, MI (US)

( * ) Notice: Subject to any disclaimer, the term of this patent is extended or adjusted under 35 U.S.C. 154(b) by 449 days.

(21) Appl. No.: 14/985,988

(22) Filed: Dec. 31, 2015

(65) Prior Publication Data

US 2016/0355866 A1 Dec. 8, 2016

Related U.S. Application Data

(60) Provisional application No. 62/172,621, filed on Jun. 8, 2015.

(51) Int. Cl.
*G01N 33/48* (2006.01)
*C12Q 1/18* (2006.01)
*G01N 27/416* (2006.01)

(52) U.S. Cl.
CPC ........... *C12Q 1/18* (2013.01); *G01N 27/4166* (2013.01)

(58) Field of Classification Search
None
See application file for complete search history.

(56) References Cited

PUBLICATIONS

Karasinski et al. (Biosensors and Bioelectronics, 2007, 22, 2643-2649).*
Ma, et al.; "Glycosylation of Quinone-Fused Polythiophene for Reagentless and Label-Free Detection of *E. coli*" Analytical Chemistry; 2015; vol. 87; pp. 1560-1568.
Ma, et al.; "Antimicrobial Susceptibility Assays Based on the Quantification of Bacterial Lipopolysaccharides via a Label Free Lectin Biosensors"; Analytical Chemistry; 2015; vol. 87; pp. 4385-4393.

(Continued)

*Primary Examiner* — Larry D Riggs, II
(74) *Attorney, Agent, or Firm* — Dierker & Kavanaugh, P.C.

(57) ABSTRACT

Real-time and end point determination of antibiotic effects are disclosed herein. In one example, a surface of a label free biosensor is exposed to a sample including a gram-negative bacteria. A frequency and/or a current of the biosensor is then allowed to reach a constant value. The surface of the biosensor is then exposed to an antibiotic. Using the biosensor, i) a frequency change versus time and a damping resistance versus time, or ii) a current versus voltage or the current versus time at a fixed potential, or iii) both i and ii are then measured. The frequency change versus time and the damping resistance versus time and/or the current versus voltage or the current versus time are correlated to determine an effect of the antibiotic on the gram-negative bacteria. Examples of the label free biosensors and methods for detecting gram-negative bacteria using the label free biosensors are also disclosed.

21 Claims, 22 Drawing Sheets

(56) References Cited

PUBLICATIONS

Wang, et al.; "Glycosylated aniline polymer sensor: Amine to imine conversion of protein-carbohydrate binding"; Biosensors and Bioelectronics; 2013; vol. 46; pp. 183-189.
Shen, et al. "Nonlabeled Quartz Crystal Microbalance Biosensor for Bacterial Detection Using Carbohydrate and Lectin Recognitions" Analytical Chemistry; 2007; pp. A-H.

* cited by examiner

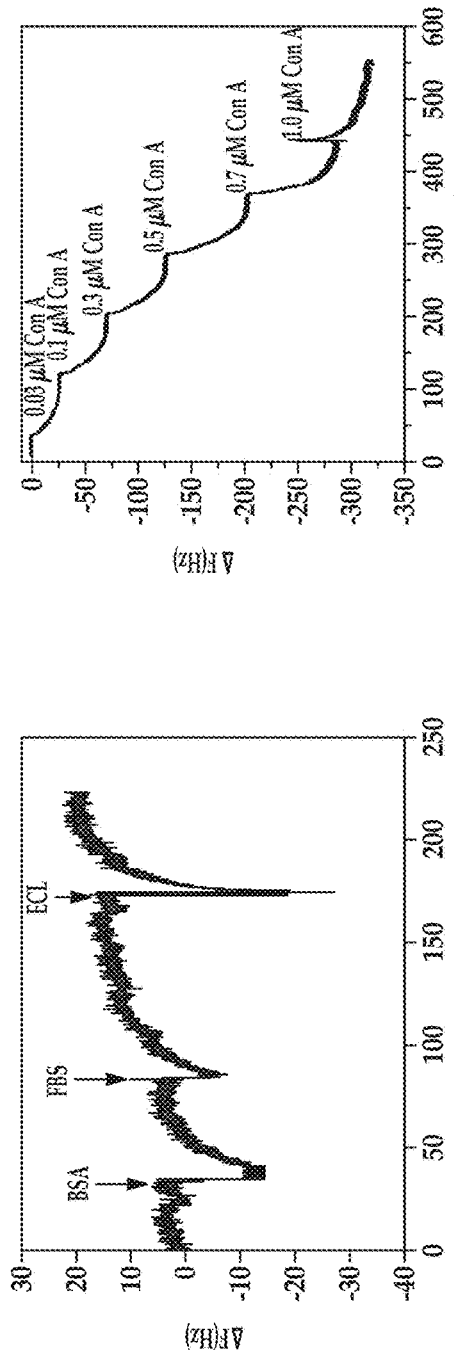
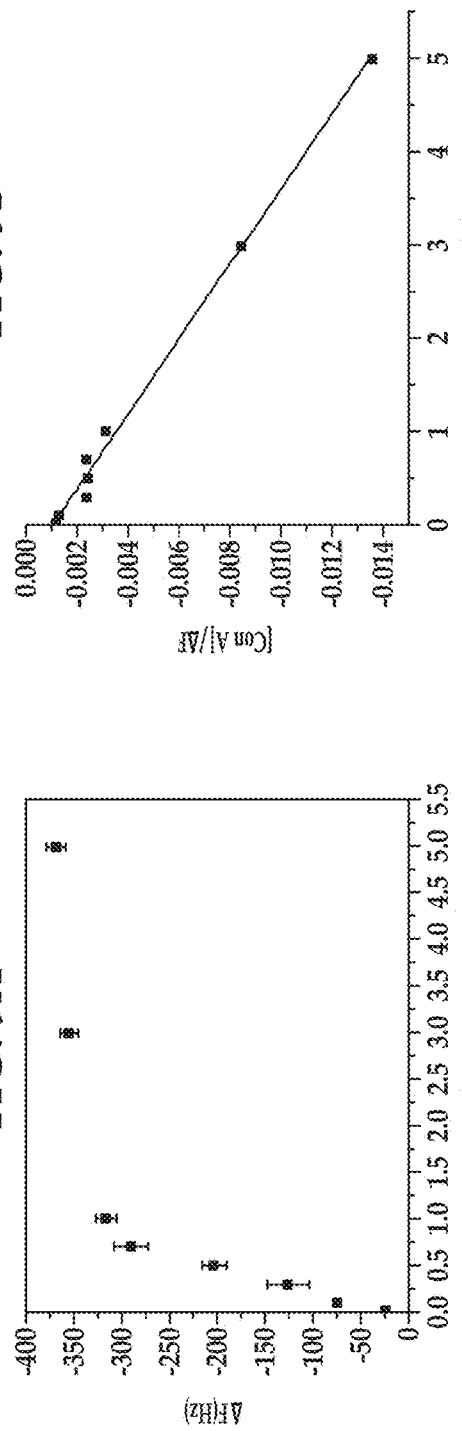
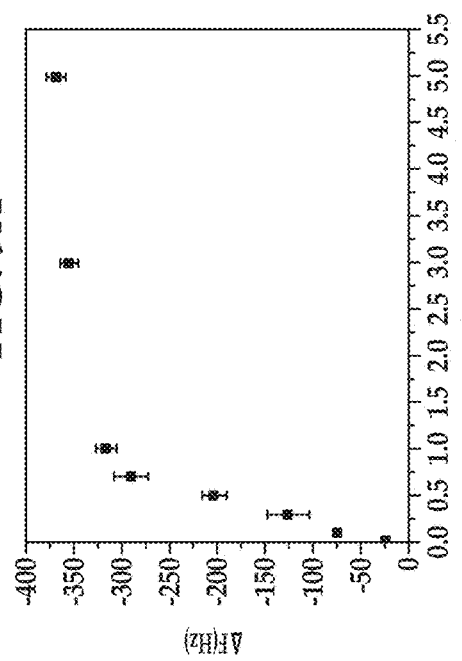
FIG. 9A
FIG. 9B
FIG. 9C
FIG. 9D

U.S. 10,287,616 B2

LABEL FREE BIOSENSORS, GRAM-NEGATIVE BACTERIA DETECTION, AND REAL-TIME AND END POINT DETERMINATION OF ANTIBIOTIC EFFECTS

CROSS-REFERENCE TO RELATED APPLICATIONS

This application claims the benefit of U.S. Provisional Application Ser. No. 62/172,621, filed Jun. 8, 2015, which is incorporated by reference herein in its entirety.

BACKGROUND

Early diagnosis of bacterial infections increases the possibility of successful medical treatment. The detection and identification of causative bacterial pathogens often utilizes microbiological techniques that rely on the culture and biochemical identification of the pathogen. Depending upon the source of the culture, the pathogen growth rate, specific nutritional needs, and the inoculum size, the presence of a pathogen may not be confirmed for up to 5 days, with another 24 to 48 hours often needed to biochemically identify the bacterial species. These delays can lead to empiric use of broad spectrum, and often multiple, antibiotics, which in turn can lead to increased rates of antibiotic resistance.

The continued evolution of antibiotic resistance in pathogenic bacteria has reached a level of concern that is highlighted by frequent references in the media due to super bugs. Extensive research has been directed toward synergistic combinations of antimicrobial agents. Such combinations are vital for treating infections that fail to respond to a single therapeutic agent. However, injudicious, empiric use of antibiotics has contributed to the emergence of more resistant pathogens and may also cause septic shocks in patients.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

(FIG. 4A) a direct $E.$ $coli$ detection using fimbriae protein binding (e.g., pili-mannose binding); and (FIG. 4B) a Concanavalin A (Con A)-mediated $E.$ $coli$ detection using LPS binding via a lectin mediator (e.g., LPS-mannose binding);

FIG. 9A is a graph depicting the frequency change versus time (minutes) when BSA, FBS, and ECL were added to the SM/TQ modified gold electrode (in a quartz crystal microbalance (QCM) setup, i.e., SM/TQ-QCM sensor);

FIG. 9B is a graph depicting the frequency change versus time (minutes) when different concentrations of Con A solutions were added sequentially to the SM/TQ-QCM sensor in HEPES buffer (pH 7.4) with 1 mM $Mn^{2+}$ and 1 mM $Ca^{2+}$;

FIG. 9C is a graph depicting the frequency changes as a function of the Con A concentration for the solution used to generate FIG. 9B;

FIG. 9D depicts the linearized adsorption isotherm of FIG. 9C, where the solid line is the best fit to the experimental data from which the dissociation constant $K_d$ was determined;

FIG. 17A represents SWV electrochemical signals, while FIG. 17B represents QCM frequency signals; and where (17a) in each figure represents the pili-mannose binding via the SM/TQ interface and (17b) in each figure represents Con A mediated binding via the Con A/SM/TQ interface;

(FIG. 26B) ciprofloxacin; (FIG. 26C) tetracycline with concentrations of 1 mg/L (26a), 10 mg/L (26b) and 30 mg/L (26c), in 1 mL of stirred HEPES with 1 mM $Mn^{2+}$ and 1 mM $Ca^{2+}$;

DETAILED DESCRIPTION

The biosensor disclosed herein has a unique sensing interface with a built-in solid state redox probe that allows for the label-free and reagentless transduction of both electrochemical and quartz crystal microbalance (QCM) sensing mechanisms. As such, the single biosensor integrates both electrochemical sensing and QCM sensing. While the single biosensor integrates both electrochemical sensing and QCM sensing, the biosensor may be utilized for one transduction mode, for example, either electrochemical sensing or QCM sensing. However, the ability to perform both electrochemical sensing and QCM sensing with the single biosensor provides different, orthogonal sets of signals/results. For example, the electrochemical sensing technique is a signal OFF approach, (i.e., an increase in analyte concentration results in a decrease of the signal) while the QCM sensing technique is a signal ON approach (i.e., an increase in analyte concentration results in an increase of the signal). The orthogonal sets of signals/results can be used for cross-validation of each other. The sensing interface of biosensor is also orthogonal, in that it can directly detect fimbriae protein binding or it can detect lipopolysaccharide (LPS) binding via a lectin mediator. Overall, the orthogonalities provide the biosensor with enhanced sensitivity, a broad, dynamic range of detection, and greater reliability via cross-validation when both electrochemical sensing and QCM sensing are performed.

As will be described in detail herein, the biosensor may be used for detecting gram-negative bacteria and/or for detecting the effect(s)/action(s) of an antibiotic on gram-negative bacteria.

Biosensor

The biosensor disclosed herein includes an electrode and an interface formed thereon. The interface includes a conductive polymer that contains fused quinone moieties which are then glycosylated to form a carbohydrate platform for bacterial detection, antibiotic effect/action detection, etc. As mentioned above, this interface can be used for label-free and reagentless detection, by electrochemical and/or QCM transducers, and by using the direct fimbriae protein binding as well as lectin mediated LPS-carbohydrate binding.

Figure 1:
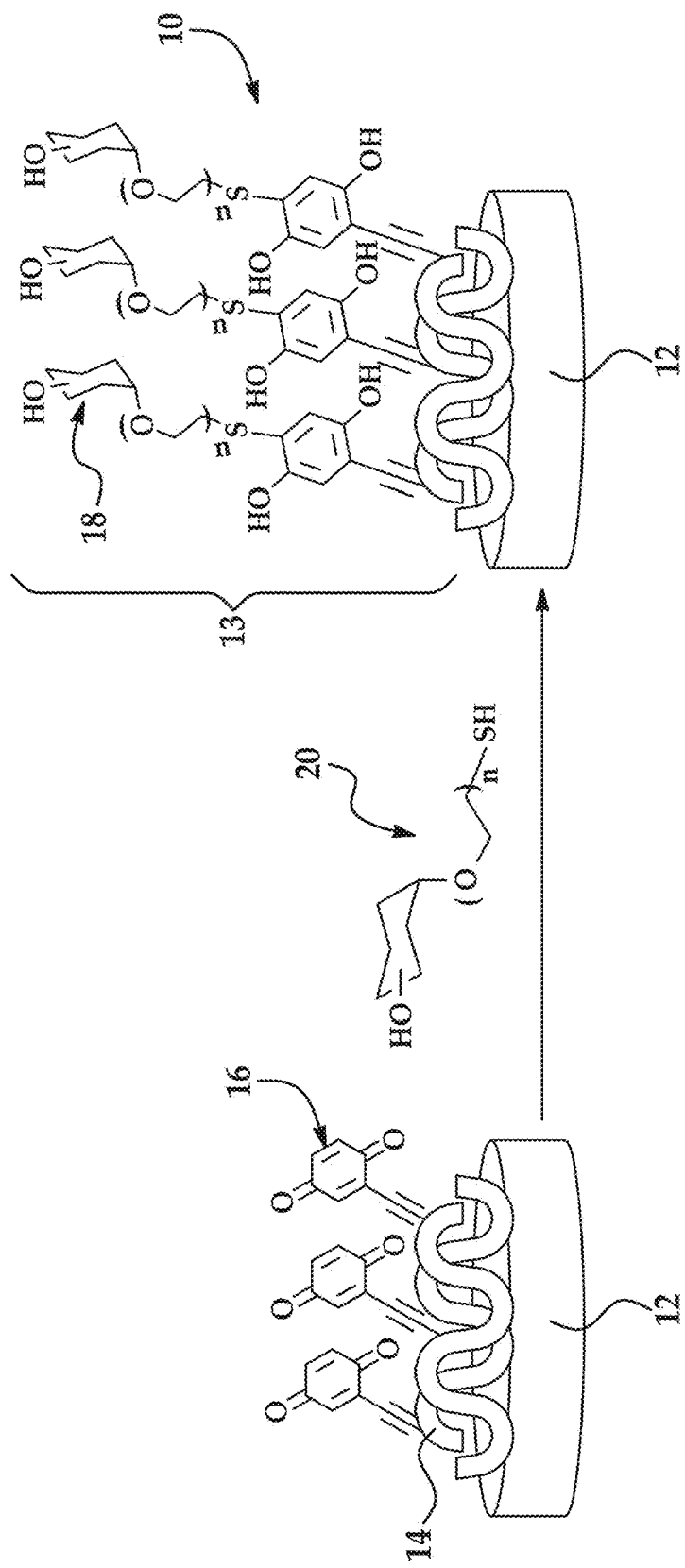
FIG. 1 is a schematic, partially perspective view of an example of the formation of a label free biosensor.

Referring now to FIG. 1, the biosensor 10 includes the electrode 12 and the carbohydrate platform 13 formed on a surface of the electrode 12. The carbohydrate platform 13 includes a conductive polymer 14 immobilized on the surface of the electrode 12, quinone moieties 16 attached/fused to the conductive polymer 14, and carbohydrates 18 attached to respective quinone moieties 16. While not shown, the electrode 12 may be a quartz crystal microbalance (QCM) electrode, which includes two conductive electrodes coated on opposite sides of a quartz plate/wafer (e.g., an AT-cut crystal). In the biosensor 10 formed on a QCM electrode, one of the two electrodes, which can be exposed to a liquid, is the transducer for electrochemical measurements, and the other of the two electrodes, which can be exposed to air, is used to generate the oscillation of the quartz plate/wafer for QCM frequency measurements. For electrochemical measurements, two other electrodes are used, one of which serves as the counter electrode and the other of which serves as the reference electrode. The counter electrode (e.g., a platinum wire) allows current to pass through, and the reference electrode (e.g., Ag/AgCl) allows an accurate potential to be applied on electrode 12.

With the single biosensor 10, the QCM measurements and the electrochemical measurements may be recorded in series (i.e., one after the other) or in parallel (i.e., simultaneously).

The electrode 12 (e.g., the two electrodes of the QCM electrode) may be formed of any suitable conductive material, such as gold (Au), aluminum (Al), carbon (C), cobalt (Co), copper (Cu), molybdenum (Mo), nickel (Ni), palladium (Pd), platinum (Pt), silver (Ag), titanium (Ti), tungsten (W), zinc (Zn), or indium tin oxide (ITO).

Any conductive polymer 14, such as those containing heterocyclic aromatics as monomeric units, may be utilized. Conductive polymers containing heterocyclic aromatics as monomeric units are suitable precursors, in part because they provide uniform and strongly adherent films. Moreover, these films can be electrochemically deposited onto a small area with a high degree of geometrical conformity and controllable thickness. Examples of the conductive polymer 14 include the following:

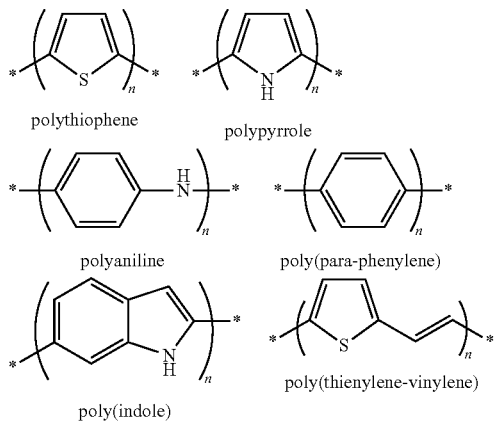

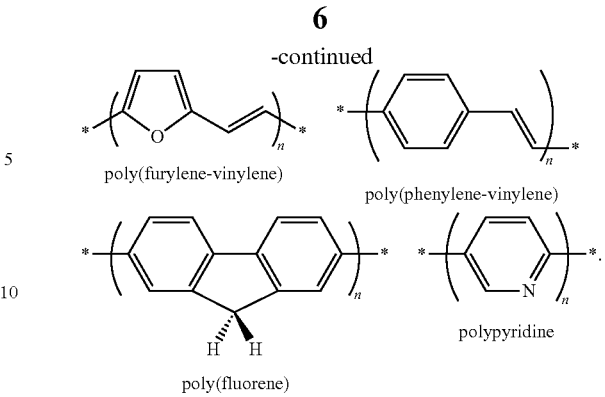

While several examples have been provided, it is to be understood that other conductive polymers 14 may also be used. Examples of other suitable conductive polymers 14 that may be used include polyvinyl ferrocene and polyacetylene.

The quinone moieties 16 are attached/fused to the backbone of the conductive polymer 14. The quinone moiety 16 may be a pendant group of the monomer that is polymerized to form the conductive polymer 14. For example, the monomer may be 3-((2,5-dimethoxyphenyl)-ethynyl thiophene (abbreviated "TQ", and shown in FIGS. 4A and 4B), which has the quinone moiety 16 as a pendant group on the thiophene monomer. In this example, thiophene is used because of its good thermal and chemical stability and relative ease of functionalization with the quinone (Q)/hydroquinone (H2Q) functionality. Polythiophene with π-conjugated quinone moieties also displays low formal potential around 0.42 V vs an Ag/AgCl reference electrode.

The biosensor 10 disclosed herein utilizes the benefits of quinone functionalized conducting polymers as a solid state redox probe, and quinone based coupling chemistry for incorporating the carbohydrate functionality. The addition and substitution reactions of quinones with nucleophiles, particularly thiol and amino groups, enable the incorporation of the carbohydrate functionality (i.e., the carbohydrate moiety 18) to the conductive polymer units 14. The use of the coupling chemistry allows the conjugation of a broad range of carbohydrates 18 (e.g., monosaccharide, oligosaccharides and polysaccharides, etc.) to the conductive polymers 14 while maintaining the carbohydrate bioactivities. This method is better than one in which the carbohydrate is conjugated in the monomers of the conductive polymer.

The carbohydrate moiety 18 may be a monosaccharide or an oligosaccharide. Some examples of suitable carbohydrate moieties include D-(+)-mannose (Man), methyl α-D-mannopyranoside (MeMan), D-(+)-glucose (Glc), D-(+)-galactose (Gal), lactose, acetylglycosamine, 2-O-α-D-mannopyranosyl-D-mannopyranose (Man2), 3,6-di-O-(α-D-mannopyranosyl)-D-mannopyranose, Galα1-3Gal oligosaccharides, fucosylated oligosaccharides, gangliosides, and sialylated oligosaccharides. Prior to its attachment to the quinone moiety 16, the carbohydrate moiety 18 may be a thiol modified carbohydrate 20, as shown in FIG. 1. The thiol modified carbohydrate 20 may be attached to the quinone moiety 16 through the Michael addition of the thiol group to the quinone moiety 16, as shown in FIG. 1. Coupling of the thiol-modified carbohydrate 20 to the quinone moiety 16 may be accomplished by repeatedly scanning the modified electrode (12, 14, 16) in a suitable potential region in a buffer containing the thiol-modified carbohydrate 20 and a catalytic amount of a strong base.

Chronoamperometry (i.e., a potential step method) may also be used to link the thiol-modified carbohydrate 20 to the modified electrode (12, 14, 16).

As mentioned above, the carbohydrate platform 13 or sensing interface of the biosensor 10 is orthogonal, in that it can directly detect fimbriae protein binding or it can detect lipopolysaccharide (LPS) binding via a lectin mediator. As such, the biosensor 10 is capable of label free detection of two bacterial cell surface biomarkers (i.e., fimbriae proteins and LPS).

Figure 2:
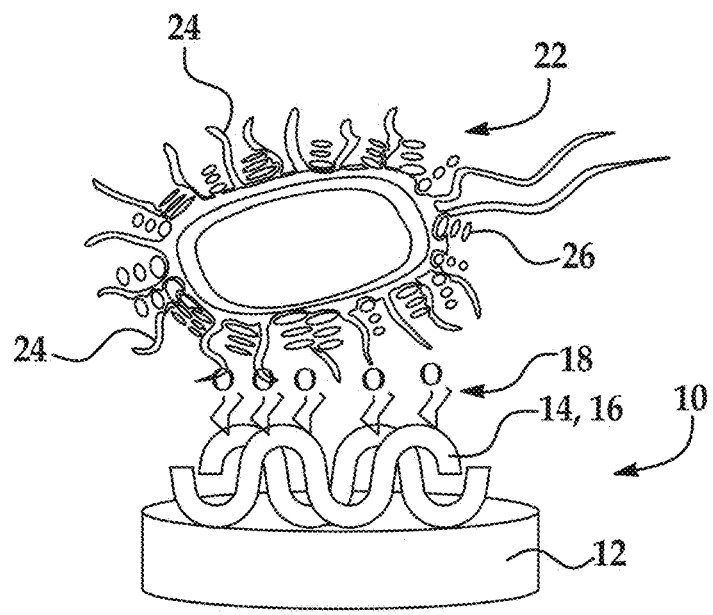
FIG. 2 is a schematic, partially perspective view of an example of direct fimbriae protein binding using an example of the label free biosensor.
Figure 3:
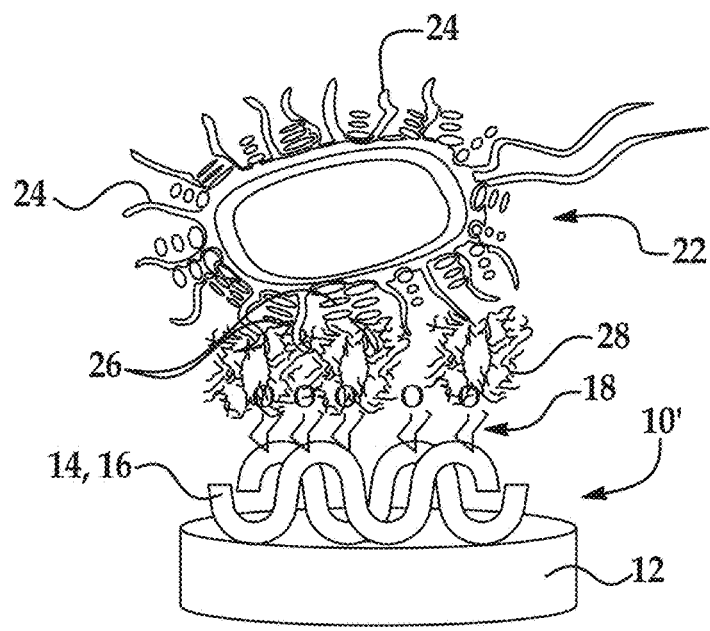
FIG. 3 is a schematic, partially perspective view of an example of lipopolysaccharide (LPS) binding via a lectin mediator using another example of the label free biosensor.

As shown in both FIGS. 2 and 3, gram-negative bacteria 22 includes pili 24 (composed of fimbriae proteins) and LPS 26 at its surface. Examples of gram-negative bacteria 22 include those in the group proteobacteria, which include *Escherichia coli* (e.g., *E. coli* W1485, a wild type of *E. coli* K-12), *Salmonella*, *Shigella*, *Vibrio*, *Helicobacteria*, *Yersinia*, other *Enterobacteriaceae*, *Pseudomonas*, *Moraxella*, *Stenotrophomonas*, *Bdellovibrio*, acetic acid bacteria, *Legionella*, etc. Other notable groups of gram-negative bacteria include the cyanobacteria, spirochaetes, green sulfur, and green non-sulfur bacteria.

The fimbriae protein binding is shown in FIG. 2. With fimbriae protein binding, the fimbriae proteins on the pili 24 of the gram-negative bacteria 22 directly bind to the carbohydrate moiety 18.

The LPS binding is shown in FIG. 3. With LPS binding, the LPS 26 of the gram-negative bacteria 22 binds to a lectin mediator 28 of an example of the biosensor 10'. In an example, the lectin mediator 28 may be attached to the carbohydrate moiety 18 by immersing and incubating the biosensor 10' in a buffer solution containing a predetermined concentration of the lectin mediator 28 and divalent cations (e.g., 2 mM $Ca^{2+}$, $Mn^{2+}$, etc.). The divalent cations can generate an active lectin mediator conformation, which can bind to the carbohydrate moiety 18. Additionally, the proteins on the pili 24 are extracellular proteins that may require calcium (or another divalent cation) for their stability and regulation. The oxygen atoms in the sugars also function as a good divalent cation (e.g., calcium) ligand.

Examples of the lectin mediator 28 include *Anguilla anguilla*, *Artocarpus integrifolia*, *Bauhinia purpurea*, *Canavalia ensiformis*, *Dolichos biflorus*, *Datura stramonium*, *Erythrina cristagalli*, *Galanthus nivalis*, *Griffonia simplicifolia*-I, *Griffonia simplicifolia*-II, *Helix pomatia*, *Lens culinaris*, *Lotus tetragonolobus*, *Maackia amurensis*, *Persea Americana*, *Arachis hypogaea*, *Glycine max*, *Sambucus nigra*, *Solanum tuberosum*, *Ulex europaeus*-I, and *Triticum vulgare*. Some lectins have specificity for binding to a specific carbohydrate. As such, while several examples have been given, it is to be understood that the lectin mediator 28 may be any lectin that functions as an adhesion promoter that is capable of binding to both the corresponding carbohydrate moiety 18 and the LPS 26. For example, the lectin mediator 28 may be Concanavalin A (Con A), which can bind to the surface LPS O-antigen glucose receptor of *E. coli* W1485 and the mannose of the conductive polymer 14 immobilized on biosensor 10.

The biosensor's unique collective properties are very sensitive to very minor perturbations, which result in significant changes of electrical conductivity and provide amplified sensitivity and improved limits of detection (i.e., 25 cell/mL for electrochemical sensor and 50 cells/mL for QCM sensor), a widened logarithmic range of detection (i.e., 3-7 for pili-mannose binding and 2-8 for Con A mediated binding), high specificity and selectivity, and an extraordinary reliability by a mechanism of internal validation. With these analytical performances, the described biosensor 10, 10' is envisaged for being capable of differentiating Gram-negative bacterial strain and species, for many important applications (including antibiotic susceptibility assays).

Figure 4A:
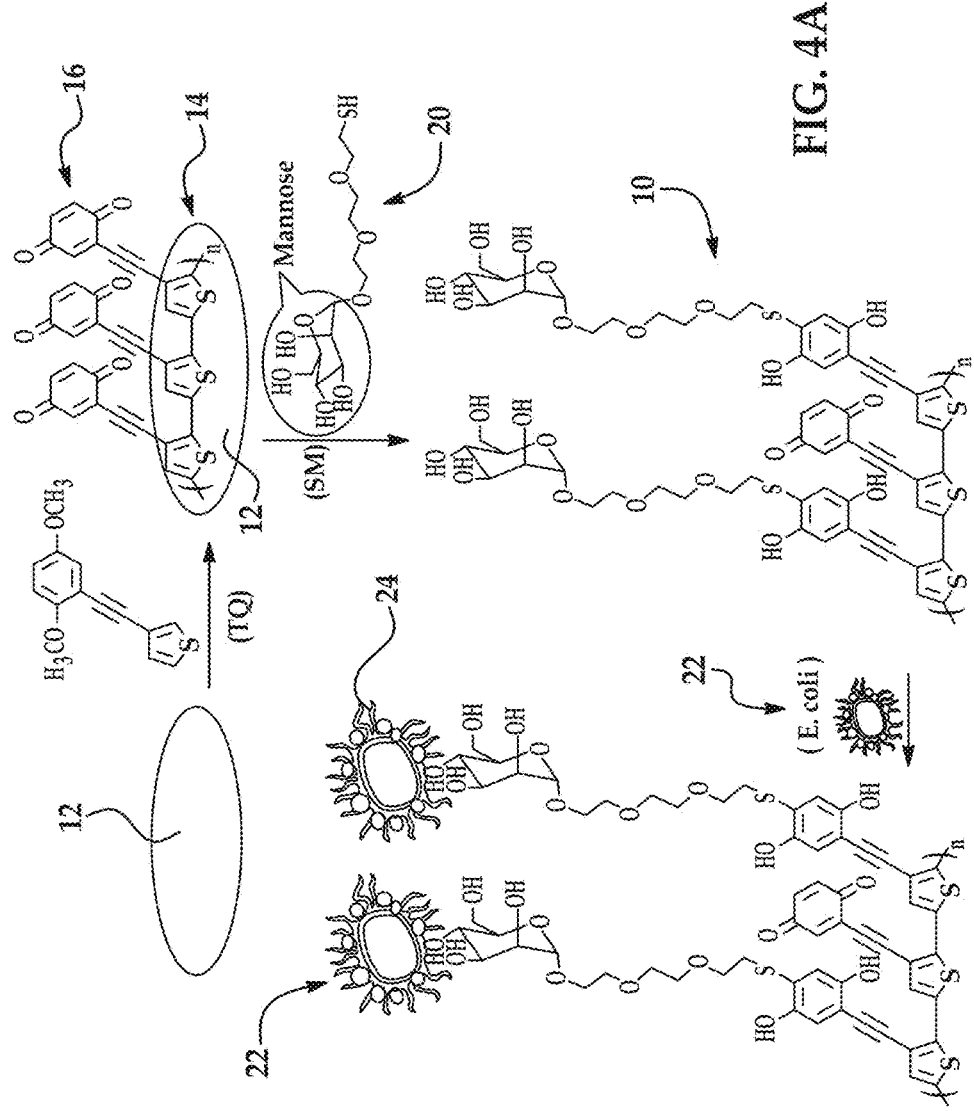
FIGS. 4A and 4B depict schematic representations of different modes of $E.$ $coli$ detection.
Figure 4B:
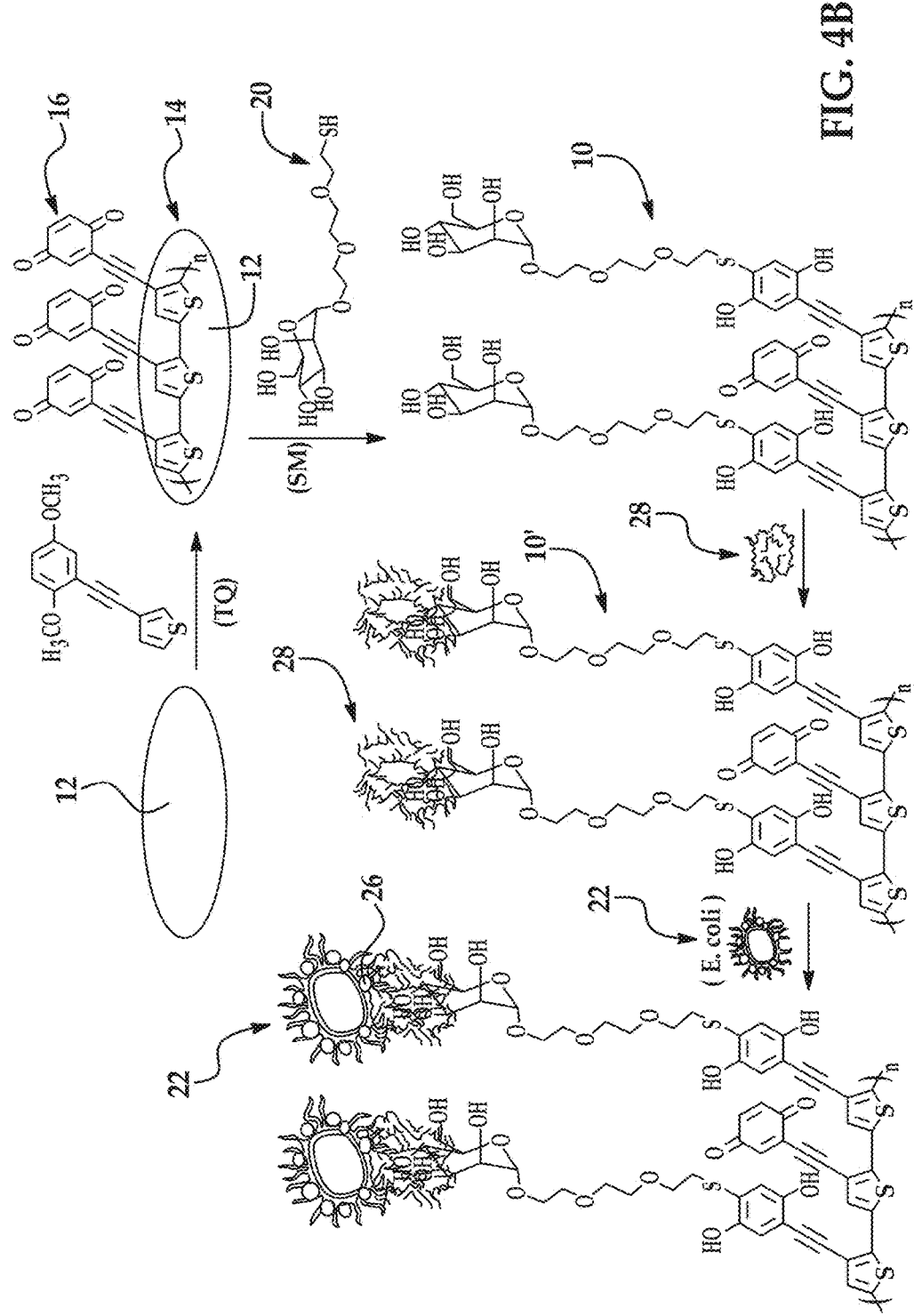

FIGS. 4A and 4B respectively depict specific examples of the directly detect fimbriae protein binding and the LPS binding via the lectin mediator 28. In these examples, the thiophene monomer containing fused quinone moieties (abbreviated TQ in both FIGS. 4A and 4B) are immobilized on the gold electrode 12 by electrochemical polymerization to form a polythiophene layer 14 having fused quinone moieties 16. Electrochemical polymerization of the monomer may be carried out using potentiometry, galvanometry, or cycle voltammetry techniques. Multiple cycles may be used to grow a relatively uniform polymer film.

In the examples shown in FIGS. 4A and 4B, the polythiophene layer 14 having fused quinone moieties 16 enables the coupling of the thiol-modified mannose 20, α-D-mannopyranoside, 2-[2-(2-mercaptoethoxy)ethoxy]ethyl (abbreviated SM in FIGS. 4A and 4B), to the gold electrode 12 based on 1,4-reductive addition of the Michael type.

The SM/TQ-glycosurface of the biosensor 10 that is generated allows label-free detection of the fimbriae proteins on bacterial pili 24 (as shown in FIG. 4A) using orthogonal QCM and electrochemical readouts (EQCM). The biosensor 10 can also be further modified with a lectin mediator 28 as shown in FIG. 4B to form the biosensor 10'. The SM/TQ-glycosurface of the biosensor 10' that is generated allows label-free detection of the LPS 26 on gram-negative bacteria 22 using orthogonal QCM and electrochemical readouts (EQCM).

Example 1 below describes a systematic study of this biointerface using these two different transduction mechanisms. Together with a panel of conductive polymer based biointerfaces targeting LPS and pili proteins, the described biosensors 10, 10' will be able to measure the subtle differences among gram-negative microorganisms based on their surface lectins and LPS biomarkers for differentiating gram-negative bacterial strains and species.

The biosensor and the methods for making the biosensor provide flexibility and control for coupling various sugars on the quinone moiety 16 on the polymer layer 14 with controlled density of the sugar units.

Methods for Detecting Gram-negative Bacteria

The biosensors 10, 10' disclosed herein may be used in several methods, including a method for detecting gram-negative bacteria. In this example of the method, the biosensor 10 or 10' is exposed to a sample containing gram-negative bacterial 22. When the biosensor 10' is to be used, the biosensor 10 may first be exposed to a solution including the lectin mediator 28 in order to form the biosensor 10'.

The biosensor 10 or 10' is then used to measure a frequency signal, a damping resistance signal, and/or an electrochemical signal of the sample.

The frequency, damping resistance, and/or electrochemical signals of the biosensor 10, 10' may be used to quantitatively estimate the bacteria concentration. For example, a linear relationship has been observed between square wave voltammetry responses (i.e., peak current) or net frequency responses derived from *E. coli* binding and the logarithm of known *E. coli* concentrations. Thus, any unknown *E. coli* concentration can be quantified using the square wave voltammetry responses or net frequency responses and calibration curves. The slope of the calibration curves from linear regression fitting represents the sensitivity of the square wave voltammetry responses or net frequency responses toward the *E. coli* concentration. The linear equation of the calibration curves can then be used to determine the *E. coli* concentration in an unknown sample. In particular, the linear fit of the square wave voltammetry responses or the net frequency responses versus the logarithm of the *E. coli* concentration may be used to determine the unknown *E. coli* concentration because the signal(s) of the sample including the unknown concentration can be measured. This type of quantification can be performed for other types of bacterial cells that exhibit a similar linear relationship between square wave voltammetry responses (or other electrochemical responses), net frequency responses, or net motional resistance responses derived from bacterial cell binding and the logarithm of known bacterial cell concentrations. With other types of bacterial cells, it is to be understood that the biosensor 10, 10' may have a different carbohydrate 18 or carbohydrate 18 and lectin mediator 28.

The previously described example of the method may also be used to identify an unknown bacterial cell. Samples of known bacterial cells may be complex, as background noise may be present. As such, in these instances, an array of biosensors 10, 10' may be used. The biosensors 10, 10' in the array may be fabricated with different carbohydrates 18 and/or carbohydrates 18/lectin 28 combinations in order to detect many different bacteria. The recorded electrochemical, frequency and/or damping resistance signal(s) of the biosensors 10, 10' when exposed to the unknown bacterial cell may be compared with a library of recorded electrochemical, frequency and/or damping resistance signal(s) of the biosensors 10, 10' when exposed to known bacterial cells. If there is little binding signal from a particular biosensor 10, 10' for either QCM or electrochemical measurements, it can be concluded that the particular bacteria detectable by the particular sensor 10, 10' is not present. If a positive signal is generated by the particular sensor 10, 10', it can be concluded that the particular bacteria is present. The type of cell may be identified when the recorded changes for the unknown bacterial cell match the data of a known bacterial cell.

Methods for Real-time and End Point Determination of Antibiotic Effects

The concerns with antibiotic resistance have escalated the need for reliable and effective assays for antimicrobial susceptibility testing. Evolution of multi-drug resistant bacteria is a major challenge, especially if it occurs in immunocompromised patients. The diversity in the genes responsible for drug resistance is an additional challenge. Established techniques for assays, e.g., broth dilution and disc diffusion, involve multiple time-consuming steps including: (1) preculturing of isolated bacteria to enrich cell density to detectable levels (24-45 48 h), (2) incubation of cells with antibiotics in 96-well plates or Petri dishes (24-48 h), and (3) determination of bacterial growth using absorption spectroscopy or by visual assessment. Moreover, these assays typically require significant quantities of patient samples such as blood, sputum, or urine for analysis.

Molecular genetics techniques (e.g., polymerase chain reaction (PCR) and microarrays) are also common, but these techniques are based on the detection of β-lactamases directly from a clinical sample. The number of lactamases is too many to propose universal primers for their detection. The direct method based on the spectrophotometric detection of lactam hydrolysis using cell extracts is labor-intensive and cannot be used routinely.

Matrix-assisted laser desorption ionization time-of-flight (MALDI-TOF) mass spectrometry (MS) has recently been introduced for the characterization of the antibiotic resistance mechanisms, but the relatively small mass of antibiotics (~1000 Da) complicates their analysis because of their interactions with the matrix and the resulting high noise levels. Instrument and its maintenance costs are additional issues in this regard.

The examples disclosed herein utilize biosensor assays for susceptibility testing. It has been found that bacterial cells express both carbohydrate and lectin adhesion structures on their outer cell walls. Certain antibiotics can act on cell wall biosynthesis, which can dramatically affect the cell surface carbohydrate and lectin expression in the cell envelope, i.e., cytoplasmic membrane and cell wall. These effects, such as the alternation of lipopolysaccharide (LPS) chain length or the alteration in lectin expressions, can significantly affect the bacterial binding with the substrates. The biosensor 10' disclosed herein can quantitatively measure the binding between the lectin mediator 28 immobilized at the carbohydrate platform 13 surface and the LPS 26 on gram-negative bacteria 22.

Because antibiotics from different classes have different mechanisms of action and the antibiotic effects on bacterial morphology and viability are concentration and time dependent, the present inventors believe that the effects of antibiotics on the LPS properties of a gram-negative bacteria may be class and concentration dependent. The biosensor 10' disclosed herein, which specifically measures the binding of gram-negative bacteria LPS 26, can be used to quantify this effect. Therefore, the measurement of the magnitude of binding is an indirect measure of the antibiotic susceptibility under various physiological conditions. The sensor 10' disclosed herein has high sensitivity (as there might be only very small changes in the LPS expressions), broad dynamic range (to accommodate different antibiotic actions and different physiological conditions), and an innovative mechanism to have the least possible interferences from the reagents used in the test. From the two different binding expressions disclosed herein (i.e., fimbriae protein binding or LPS binding), the mechanism that uses LPS structures and mediated by the lectin mediator 28 (e.g., Concanavalin A (Con A)) is shown to have more rigid character, thus leading to very high sensitivity and low detection limit (i.e., up to 50 cells/mL). Therefore, in some of the examples disclosed herein, the function of Con A is utilized to mediated LPS detection of the biosensor 10'.

Moreover, the utilization of integrated quartz crystal microbalance and electrochemical readouts (EQCM) transduction mechanism provides internal validation that significantly enhances the reliability of detection.

Using this biosensor 10', real-time and end point measurements and information may be obtained. The sensor 10' enables fast bacterial susceptibility testing, and the results may be used to explain the fundamental mechanisms of the differences in mode of action of antibiotics, their influence on cell surface morphology, and antibiotic efficacies. Moreover, many physiological complications such as septic shock, which is associated with antibiotic released endotoxins (LPS), can by identified and treated.

In an example of the method for real-time determination of antibiotic effects, the biosensor 10' is exposed to a sample including gram-negative bacteria 22. After sample exposure, the frequency, current, or both the frequency and the current of the biosensor 10' is/are allowed to reach a constant value. This serves to immobilize the bacteria 22 via lectin-LPS binding. The constant value provides a baseline reading that indicates that the binding of the gram-negative bacteria 22 is complete.

The biosensor 10' is then exposed to the antibiotic. Any antibiotic may be used. In an example, the antibiotic is one that is believed to have an effect on the gram-negative bacteria 22. Examples of the antibiotic include ciprofloxacin, ceftriaxone, tetracycline, or the like.

QCM measurements and/or electrochemical measurements are then measured using the biosensor 10'. In an example, the measurements are taken immediately after antibiotic exposure and after a predetermined incubation period(s). QCM measurements include frequency changes versus time and/or damping resistance versus time. Electrochemical measurements include current versus voltage curves. The current versus voltage curve enables a peak current to be seen. For some electrochemical measurements, the potential at peak current will be selected. This potential will be set and the current will be monitored versus time (similar to frequency versus time measurement). In these examples, the change of current is the signal that is monitored to obtain the information of the effects of antibiotic for bacterial killing or injuring.

The frequency changes versus time and damping resistance versus time measurements and/or the current versus voltage or current versus time (at a specific voltage/fixed potential) measurements are correlated to an effect of the antibiotic on the gram-negative bacteria 22. As examples, the effect may be the antibiotic killing the bacteria 22 or the antibiotic inhibiting growth of the gram-negative bacteria 22. Any antibiotics that can lead to the change of cell morphology and/or with alternation of the cell membrane ultrastructure that ultimately increases drug intake can be correlated to the QCM and electrochemical measurements. For example, antibiotics lead to bacterial killing through interactions with the membrane that result in pore formation or activation of cell-wall stress systems and membrane depolarization, or lead to changes in cell morphology that are associated with the primary drug-protein interaction. The lysis-dependent cell death mechanism, however, has proven to be much more complex, involving many active cellular processes. For example, antibiotics that are a cell wall synthesis inhibitor can result in changes to cell shape and size, induce cellular stress responses, and culminate in cell lysis.

One example of correlating the data to an antibiotic effect includes recognizing that the frequency changes versus time and damping resistance versus time measurements and/or the current at certain voltage measurements shift in a direction opposite to the respective corresponding signals measured after the biosensor 10' is exposed to the sample including the gram-negative bacteria 22. Signals observed during gram-negative bacteria 22 exposure are indicative of bacteria cell binding, and when opposite signals are observed after antibiotic exposure, the opposite signals indicate that binding is reduced and/or the bacteria has changed (e.g., cell morphology and/or alteration of the cell membrane ultrastructure), which is an indication of bacterial killing or injuring.

In this example of the method, an effective concentration or dosage of the antibiotic for treating the gram-negative bacteria 22 may be identified by measuring the signal(s) at different antibiotic concentrations. When a little change is observed between signals at two different concentrations and the change is bigger than the statistically determined noise level, the lower of the two concentrations may be determined to be the effective concentration or dosage. In other words, when two concentrations of antibiotics are tested and both generate signal changes, the antibiotic with the smaller concentration compared with the baseline signal can be regarded as the one that is effective.

In this example of the method, a response time of the antibiotic may be identified by measuring the signal(s) at different incubation times. As an example, when comparing the results of several antibiotics, a smaller change in frequency at the same incubation time indicates that the antibiotic is less effective at killing the gram-negative bacteria 22 being tested. This allows a determination to be made for the same concentration of different antibiotics with regard to how long each antibiotic interacts with bacteria. This determination can indicate the effectiveness of the antibiotic for bacterial killing, and may be used for drug delivery design. For example, if a low dose of a drug is available, a drug delivery design may be identified that will allow the drug to be active in the body for longer time, which can be as effective as a high dose of the drug that is not in the body long enough. Incubation time information may also be used to reduce drug toxicity.

When both QCM measurements and electrochemical measurements are taken, the results may be used for cross-validation. The QCM or electrochemical measurements alone can provide the antibiotic susceptibility assay, but with both measurements, the results are validated by each other, thus making them more reliable and accurate. Cross-validation enables one to identify false positive(s) or false negative(s) in the real world conditions where interferences may be abundant.

In an example of the method for end point determination of antibiotic effects, the biosensor 10' is exposed to a sample including gram-negative bacteria 22 and the antibiotic. The sample may be incubated either before it is exposed to the surface of the biosensor 10' or after it is exposed to the surface of the biosensor 10'.

QCM measurements and/or electrochemical measurements are then measured using the biosensor 10'. The measurements may be taken immediately after sample exposure and/or after a predetermined incubation period(s). As mentioned above, QCM measurements include frequency changes versus time and/or damping resistance versus time. Electrochemical measurements include current versus voltage curves and/or current at a fixed potential versus time curve.

The method may further involve normalizing i) the frequency of the sample to a frequency obtained for a control sample including the gram-negative bacteria and no antibiotic, or ii) the damping resistance of the sample to a damping resistance obtained for a control sample including the gram-negative bacteria and no antibiotic, or ii) the electrochemical signal of the sample to an electrochemical signal obtained for a control sample including the gram-negative bacteria and no antibiotic. Normalizing the data to a control shows the relative change of the signals (versus the control or baseline signal) which enables the identification of a percentage change of the binding of the gram-negative bacteria for a given concentration of the antibiotic. The binding percentage can then be correlated to an effect of the antibiotic on the gram-negative bacteria 22. For example, if the binding percentage is reduced compared to a control, it can be concluded that the antibiotic inhibited the growth of the gram-negative bacteria 22 and affected the LPS 26 integrity and function so that a smaller number of gram-negative bacteria 22 bound to the biosensor 10'. Several antibiotics could be tested and the results compared in order to determine if their strengths in inhibiting bacteria growth and binding.

In this example of the method, an effective concentration or dosage of the antibiotic for treating the gram-negative bacteria 22 may be identified by measuring the signal(s) at different antibiotic concentrations. When a little change is observed between signals at two different concentrations, the lower of the two concentrations may be determined to be the effective concentration or dosage. In an example, the minimum effective dosage is the one which gives signals that are higher than three times the standard deviation of the baseline signal changes.

In this example of the method, a response time of the antibiotic may be identified by measuring the signal(s) at different incubation times. As an example, when comparing the results of several antibiotics, a bigger change in frequency at the same incubation time indicates that the antibiotic is more effective at killing the gram-negative bacteria 22 being tested.

When both QCM measurements and electrochemical measurements are taken, the results may be used for cross-validation. As mentioned above, the QCM or electrochemical measurements alone can provide the antibiotic susceptibility assay, but with both measurements, the results are validated by each other, thus making them more reliable and accurate. Cross-validation enables one to identify false positive(s) or false negative(s) in the real world conditions where interferences may be abundant.

The example methods disclosed herein are unlike the monosaccharide-quinone biointerface for electrochemical probing of protein binding, which can be time consuming (about 12-36 hours) due to slow self-assembled monolayer (SAM) immobilization, the instability of the S—Au bond at reductive potentials, and the high mobility of the SAM monolayer due to the weakness of the S—Au bond.

To further illustrate the present disclosure, examples are given herein. It is to be understood that these examples are provided for illustrative purposes and are not to be construed as limiting the scope of the present disclosure.

EXAMPLES

Example 1

Biosensor Used in Gram-negative Bacteria Detection

Chemicals and Materials
4-(2-Hydroxyethyl)-1-piperazineethanesulfonic acid (HEPES) was purchased from VWR International. Concanavalin A (Con A) and *Erythrina cristagelli* (ECL) were purchased from Sigma. *Staphylococcus aureus* serotype 1 (*S. aureus*) (ATCC 12598), *E. coli* O86: K61 (B7) (ATCC 12701), and *E. coli* W1485 (ATCC 12435) were obtained from ATCC. *E. coli* W1485, a wild type of *E. coli* K-12, was used as the model Gram-negative bacterial analyte in order to demonstrate the described improvements in the biosensor detection system. *E. coli* W1485 is a "semirough" bacterial strain in which the intact LPS core is capped by a single O-antigen subunit consisting of glucose and N-acetylglucosamine, which could be recognized by specific Con A.

All other reagents and materials were analytical grade and solvents were purified by standard procedures. Biograde and deionized water was used throughout the experiments.

3-((2,5-dimethoxyphenyl)ethynyl)thiophene (abbreviated TQ in FIGS. 4A and 4B and throughout this Example) and α-D-mannopyranoside, 2-[2-(2-mercaptoethoxy) ethoxy]-ethyl (abbreviated SM in FIGS. 4A and 4B and throughout this Example) were prepared as described below.

The cultures of *E. coli* strains were grown in sterilized Luria-Bertani broth (LB broth) prepared by adding 10 g of tryptone, 5 g of yeast extract, and 10 g of NaCl into 1 L of biograde water adjusted to pH 7.4 at 37° C. for 18 hours in a shaking incubator. The viable cell number was determined by conventional agar plate counting. The crude cultured bacteria sample was directly diluted with 10 mM HEPES buffer to the desired concentrations and frozen for further use without any washing steps. The unit, cells/m L, was used to quantify the number of bacteria in the HEPES buffer rather than colony-forming unit per milliliter.

Biosensor Interface Fabrication
A QCM gold electrode consisted of a thin AT-cut quartz crystal wafer with vapor deposited gold electrode on each side (10 MHz, non-polished with 1000 A gold) (Internaltional Crystal Manufacturing Co. Inc.). The gold electrode had an exposed gold area of 0.22 cm$^2$ and QCM active Au area of 0.20 cm$^2$. The gold electrode was cleaned with Piranha solution (1:3 30% $H_2O_2$: concentrated $H_2SO_4$) for 5 minutes to remove organic adsorbate impurities from the gold surfaces. The gold electrode was then rinsed thoroughly with deionized water and subsequently dried with nitrogen flow. The gold QCM surface roughness factor was determined to be 2.92 by integrating the anodic peak of the gold oxidation in 0.5 M $H_2SO_4$ and comparing it with the standard value (390 μC/cm2) of the Au oxidation processes in 0.5 M aqueous $H_2SO_4$ (limit to extent of formation of the quasi-two-dimensional oxide state on Au electrodes).

A mannosylated fused polythiophene film (containing fused quinone moieties) (SM/TQ) was fabricated on the QCM gold electrode. First, 3-((2, 5-dimethoxyphenyl) ethynyl)thiophene (abbreviated TQ, see "3" below in scheme 1) and α-D-Mannopyranoside, 2-[2-(2-mercaptoethoxy) ethoxy]ethyl (abbreviated SM, see "7" below in scheme 2) were synthesized.

To synthesize TQ, 3-ethynyl thiophene, (0.85 g, 7.8 mmol) (see "2" below in scheme 1) was added into a solution of 1-bromo-2,5-dimethoxybenzene (1.87 g, 8.6 mmol) (see "1" below in scheme 1) in 30 mL anhydrous THF.

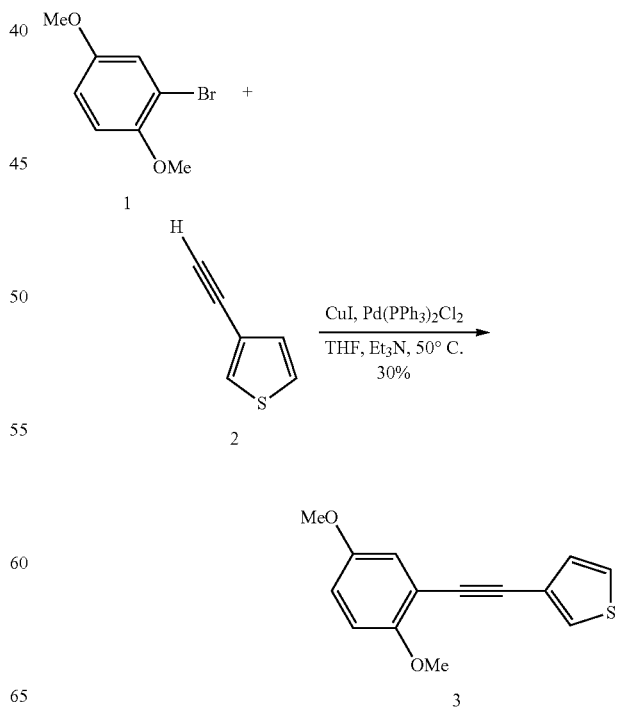

Scheme 1

When 2 was added into 1, Pd(PPh$_3$)$_2$Cl$_2$(165 mg, 0.24 mmol), CuI (45 mg, 0.24 mmol), triphenylphosphine (62 mg, 0.24 mmol) and 20 mL triethylamine were also added under dry nitrogen atmosphere. The mixture was stirred over night at 50° C. under dry nitrogen atmosphere. After the completion of the reaction (which was monitored by TLC), the reaction mixture was concentrated under reduced pressure, diluted with methylene chloride, and washed with aqueous 1 N HCl, distilled water and brine. The organic layer was collected and dried over anhydrous sodium sulfate. The crude product was purified by silica gel column chromatography (hexane/methylene chloride/ethyl acetate, 3/6/1.5) to obtain compound 3 in scheme 1 as brown oil (570 mg, 30%). $^1$H NMR (400 MHz, CDCl$_3$): δ 7.49 (d, J=2.8 Hz, 1H), 7.23 (dd, J=4.8, 2.8 Hz, 1H), 7.17 (d, J=4.8 Hz, 1H), 6.98 (d, J=2.8, 1H), 6.80 (d, J=2.8, 1H), 6.78 (s, 1H), 3.81 (s, 3H), 3.73 (s, 3H). $^{13}$C NMR (100 MHz, CDCl$_3$): δ154.6, 153.4, 130.2, 129.0, 125.4, 122.6, 118.2, 116.0, 113.0, 112.2, 88.7, 85.3, 57.0, 56.7, 56.0.

SM (compound 7) was synthesized according to a reported procedure, the steps of which are shown in Scheme 2. $^1$H NMR (400 MHz, CD$_3$OD): δ 4.78 (d, J=1.2 Hz, 1H), 3.84-3.79 (m, 4H), 3.71-3.55 (m, 12H), 2.64 (t, J=6.8 Hz, 2H).

cycles. The yellow-brown film modified gold electrode was washed with CH$_3$CN and water, and was characterized as described below. Then it was incubated in a solution of 4 mg/mL of the thiol modified mannose (SM) in 10 mM HEPES buffer containing a catalytic amount of triethanolamine. The mannosylation of quinone-fused polythiophene was obtained by repeatedly scanning in the potential region from −0.2 V to 0.8 V at a scan rate of 20 mV/s for 20 cycles. The gold surface was washed with biograde water and HEPES buffer to give the SM/TQ modified gold electrode.

Biosensor Interface Characterization

In this Example, a RQCM (Research Quartz Crystal Microbalance, MAXTEK Inc.) and a GAMRY electrochemical workstation were used to characterize the biointerface and its binding events with proteins and bacteria, respectively.

For QCM characterization and measurements, the SM/TQ (i.e., the mannosylated fused polythiophene film) modified gold electrode of QCM was mounted in a custom-made Kel-F cell. A baseline was recorded in 1 mL of 10 mM HEPES buffer containing 1 mM Ca$^{2+}$ and 1 mM Mn$^{2+}$. Each of the samples to be analyzed was then introduced into the detection cell after stabilization of resonance frequency

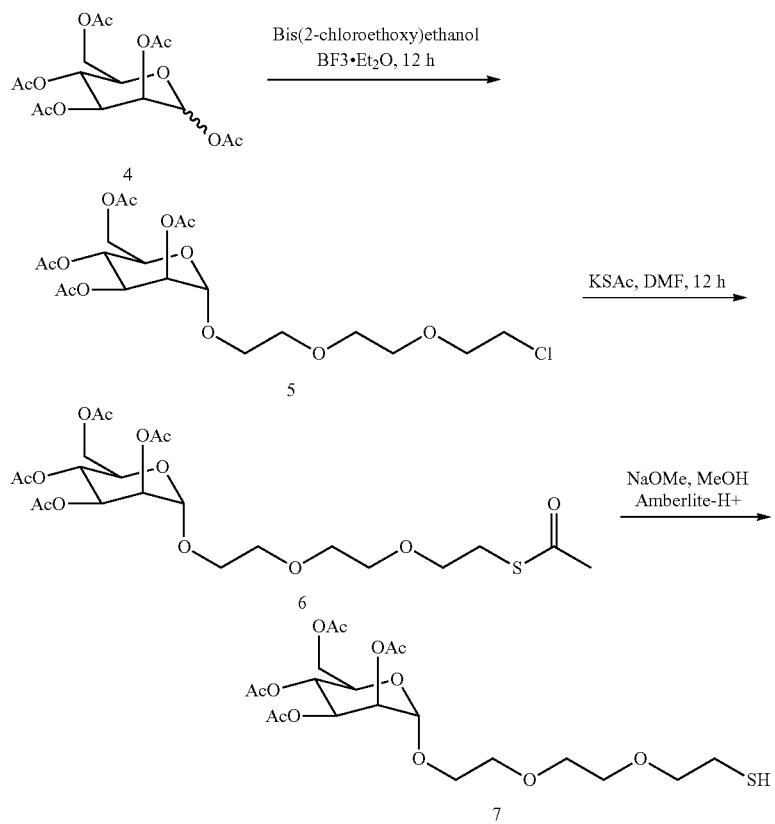

(shift less than 1 Hz·min$^{-1}$). Then, different concentrations of Con A or *E. coli* was injected into the Kel-F cell. A small magnetic stir bar was used to increase the mass transfer through convection. The frequency changes of the RQCM (Research Quartz Crystal Microbalance, MAXTEK Inc.) were monitored in real time.

The electrochemical polymerization and deposition of TQ on the gold electrode took place in CH$_3$CN with 0.1 M LiClO$_4$ as a supporting electrolyte. The polymerization and deposition was performed by repeatedly scanning in the positive potential region from 0 V to 1.2 V (vs Ag/AgCl wire/reference electrode) at a scan rate of 20 mV/s for 20

For electrochemical characterization and measurements, a GAMRY electrochemical workstation was used. A three-electrode system was used. Before formation of SM/TQ, the TQ modified gold electrode was used as the working electrode, a platinum wire was used as the counter electrode, and an Ag/AgCl (saturated in KCl) electrode was used as the reference electrode. After the SM/TQ interface was prepared, the SM/TQ modified gold electrode of QCM was used as the working electrode, the platinum wire was used as the counter electrode, and the Ag/AgCl (saturated in KCl) electrode was used as the reference electrode. 1 mL of 10 mM HEPES buffer containing desired concentration of Con A or E coli was added into the fixed electrochemical cell for 60 min at about 25° C., followed by extensive rinsing with incubation buffer to remove any physically adsorbed Con A or *E. coli*. Then, 1 mL of 10 mM HEPES buffer was placed into the cell. Cyclic voltammetric and square wave voltammetric measurements were performed under ambient conditions (~25° C.). Each measurement had been repeated at least three times with the TQ modified electrode or the TQ/SM modified electrode.

TQ and SM/TQ Characterization

The proposed glycosurface chemistry for the biointerface fabrication was characterized. The electrochemical polymerization of TQ at the Au electrode was characterized, and the coupling of mannose thiol (SM) with quinone derivatized polythiophene via 1, 4-reductive Michael-type addition to form an SM/TQ modified gold electrode at the sensing interface was characterized. Cyclic voltammetry (CV) was used.

Figure 5:
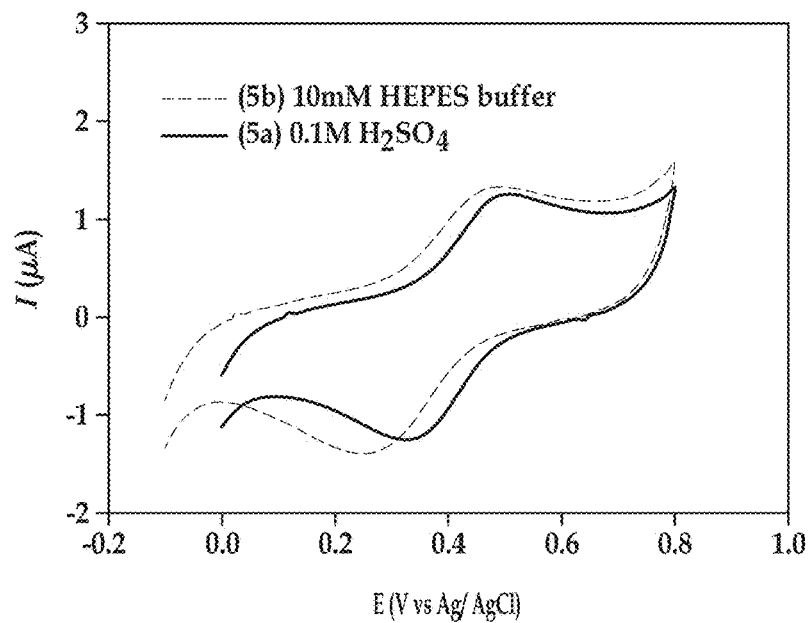
FIG. 5 is a graph depicting cyclic voltammograms (CVs) of a 3-((2,5-dimethoxyphenyl)-ethynyl thiophene (abbreviated "TQ") modified gold electrode recorded in 0.1 M $H_2SO_4$ (a) and 10 mM HEPES (pH 7.4) (b) after electrochemical polymerization of TQ in $CH_3CN$ with 0.1 M $LiClO_4$ for 20 cycles, scan rate: 20 mV/s.

CVs in 0.1 M $H_2SO_4$ (FIG. 5, curve 5a) and 10 mM HEPES buffer (FIG. 5, curve 5b) were recorded. From curve 5a, the formal potential ($E^{o'}$) was determined to be +0.42±0.004 V with a peak separation ($\Delta E$) of 0.14±0.008 V in 0.1 M $H_2SO_4$. Compared to the CV recorded in 0.1 M $H_2SO_4$, the $E^{o'}$ shifted negatively toward +0.37±0.002 V with the broader $\Delta E$ of 0.18±0.006 V calculated from curve b in 10 mM HEPES buffer (pH=7.4). As shown in FIG. 5, curve 5b, the anodic peak of TQ (+0.48 V) lied between +0.15 V (the characteristic peak of quinone, not shown) and 0.75 V (the characteristic peak of polythiophene), which indicates that the redox process of TQ is the result of the conjugated thiophene and quinone moieties in TQ, not thiophene or quinone alone.

Additionally, the CVs of FIG. 5 displayed the full width at half-maximum to be about 150 mV, which is much larger than the ideal Nernstian value for a surface-confined two-electron redox couple (45 mV), that may have resulted from lateral interactions between the head groups in the monolayer and from the influence of thiophene group in the TQ.

The estimated surface coverage of TQ ($\Gamma_{TQ}$) of $1.54 \times 10^{-10}$ mol/cm$^2$ was calculated by integrating the cathodic peak area in the curve (FIG. 5, curve b) and considering the two-electron process for the Q/H$_2$Q couple and the gold surface roughness factor 2.92. Previously reported values for a full monolayer coverage of Q/H$_2$Q attached to a gold electrode with a different linker are between $2.0 \times 10^{-12}$ mol/cm$^2$ and $5.6 \times 10^{-10}$ mol/cm$^2$. The $\Gamma_{TQ}$ in this Example is consistent with these values, suggesting that the TQ packed tightly under the conditions tested and is a monolayer.

Figure 6:
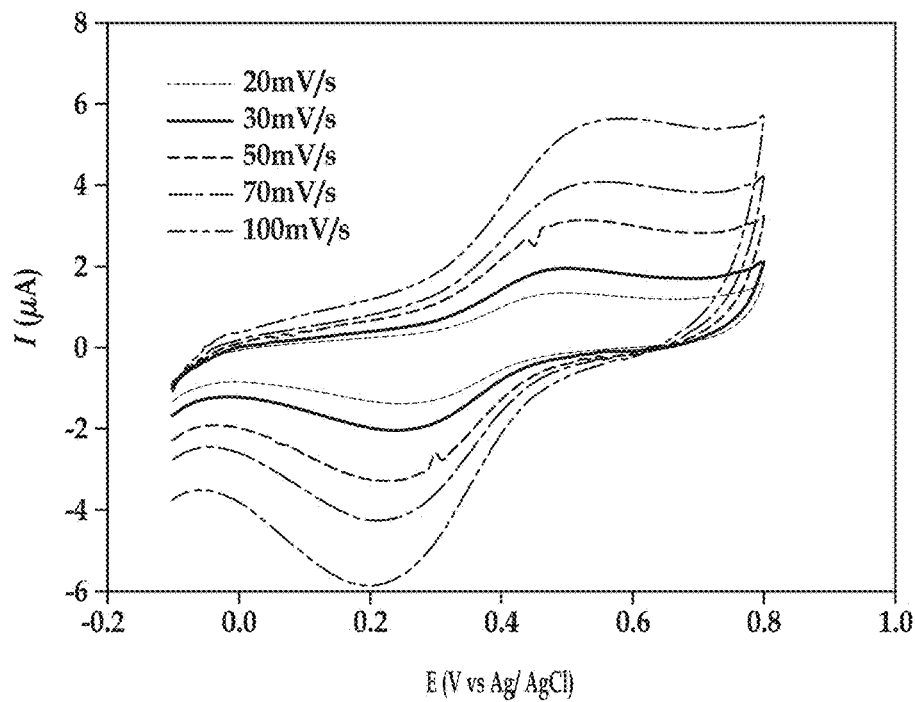
FIG. 6 is a graph depicting the CVs of TQ modified gold electrodes recorded in 10 mM HEPES (pH 7.4) at scan rates of 0.020 V/s, 0.040 V/s, 0.060 V/s, 0.080 V/s, and 0.100 V/s.

FIG. 6 displays CV curves as a function of scan rate for the TQ modified gold electrode in 10 mM HEPES (pH 7.4). From these curves, it can be calculated that the anodic and cathodic peak currents for the H$_2$Q/Q redox couple scaled linearly with scan rate from 20 mV/s to 100 mV/s, which is consistent with a surface-bound redox moiety.

Figure 7:
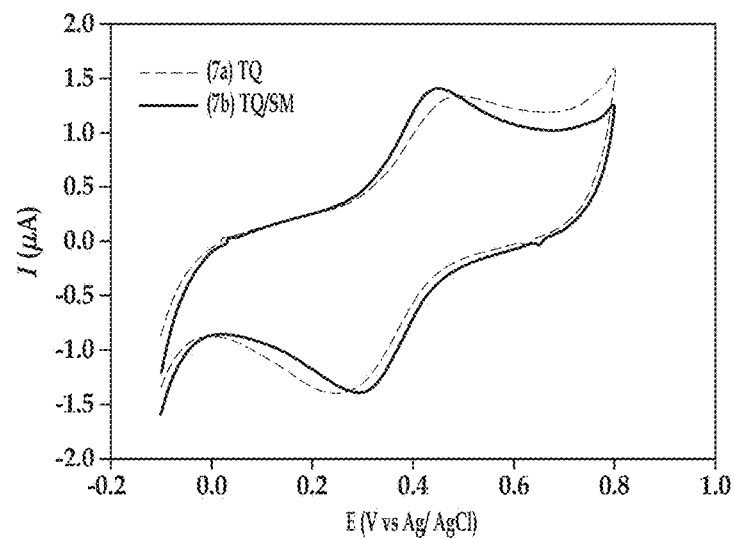
FIG. 7 is a graph depicting the CVs of the TQ modified gold electrode (7a) and a 2-[2-(2-mercaptoethoxy)ethoxy]ethyl/3-((2,5-dimethoxyphenyl)ethynyl)thiophene (SM/TQ) modified gold electrode (7b) recorded in 10 mM HEPES (pH 7.4) at a scan rate of 20 mV/s.

FIG. 7 depicts CV curves of the TQ (7a) and the SM/TQ (7b) modified gold electrodes in 10 mM HEPES buffer. Compared to curve 7a, curve 7b showed that the anodic peak potential shifted negatively and the cathodic peak potential shifted positively. As shown in curve 7b, $E^{o'}$ negatively shifts from +0.37 to +0.35 V along with the $\Delta E$ decreasing from 0.18 V to 0.12 V after introducing mannose thiol to TQ, which is possibly attributed to the increased electron transfer rate (ET). Based on resonance structure of the addition product of SM to the quinone ring of TQ, two possible mechanisms account for the increased ET reaction at the electrode. The first possible mechanism is that the addition of the SM to the quinone ring of TQ may change the mechanism of proton-coupled ET of Q/HQ center. The second possible mechanism, based on Marcus formalism, is that with the addition of SM there may be a smaller inner sphere reorganizational energy (i.e., smaller changes in bond lengths between the oxidized and the reduced states) and changes of microenvironment of Q/HQ, which would accelerate the ET. The negatively shifted $E^{o'}$ and decreased $\Delta E$ in FIG. 7 confirmed that SM was successfully confined to the TQ modified gold electrode, and gave a strong electrochemical signal produced by Q/HQ couple (indicating the sensor is suitable as an electrochemical sensor for Con A and bacterial detection).

The characterization data indicates that the method of this Example, using quinone fused polythiophene with sugar thiol, does not involve time consuming immobilization via self-assembled sugar thiol that results in instable S-Au bond. The characterization data also indicates that the biosensor has a built-in solid state redox probe for electrochemical readout.

SM/TQ Binding Characterization

The SM/TQ modified gold electrode was characterized by cyclic voltammetry in a 5.0 mM $K_3Fe(CN)_6$-0.10 M KCl solution.

Figure 8A:
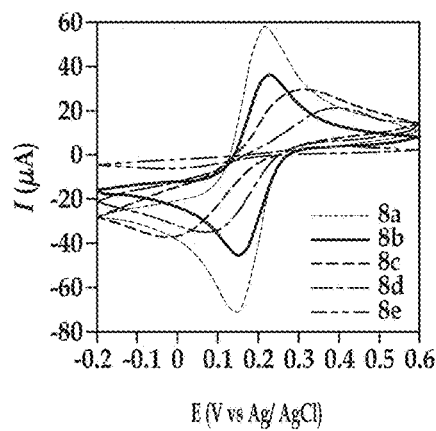
FIG. 8A is a graph depicting the CVs of (8a) a bare gold electrode, (8b) TQ modified gold electrode, (8c) SM/TQ modified gold electrode, (8d) the SM/TQ modified gold electrode treated with 300 nM Con A in 50 mM HEPES buffer (pH 7.4), and (8e) the Con A/SM/TQ modified gold electrode treated with $5.0\times10^2$ $E.$ $coli$ W1485, each recorded in a 5.0 mM $K_3Fe(CN)_6$-0.10 M KCl solution at a scan rate of 100 mV/s.

As shown in FIG. 8A, at the bare gold electrode (curve 8a), $Fe(CN)_6^{3-}$ reduction had a peak separation value ($\Delta E_p$) of ~96 mV and an anodic peak current ($I_{pa}$) of 57 µA. In comparing the data for curves 8a and 8b, it is shown that after the TQ was attached to the bare gold electrode using electrochemical polymerization, there was a significant decrease in $I_{pa}$ by about 38%, and $\Delta E_p$ increased to 102 mV. This behavior was consistent with the electrical conductivity of TQ and the resistance as a result of HQ/Q group of TQ immobilization, because the electrical conductivity of the HQ/Q unit is limited.

As the SM was coupled to the quinone group of the TQ (FIG. 8A, curve 8c), the $\Delta E_p$ increased from about 102 mV to about 236 mV and $I_{pa}$ decreased from 38 µA to 29 µA. The biointerface of the SM/TQ modified gold electrode could hinder $Fe(CN)_6^{3-}$ redox processes in solution, leading to the decrease in redox current of $Fe(CN)_6^{3-}$.

After Con A was captured onto the surface of SM/TQ modified gold electrode, the $\Delta E_p$ increased from about 236 mV to about 423 mV and the $I_{pa}$ decreased from 29 µA to about 12 µA (FIG. 8A, curve 8d). This was attributed to the fact that an insulating layer on the surface of SM/TQ modified gold electrode was generated and the electron transfer of $[Fe(CN)_6]^{3-}$ to the surface of gold electrode was prohibited. After the Con A/SM/TQ modified gold electrode was treated with a low concentration of *E coli* ($5.0 \times 10^2$), the $\Delta E_p$ further increased from about 423 mV to about 432 mV and the $I_{pa}$ greatly decreased from about 12 µA to about 2.1 µA (FIG. 8A, curve 8e). The changed $I_{pa}$ showed that the SM/TQ modified gold electrode can also be used to detect *E coli* using $Fe(CN)_6^{3-}$ as a probe. However, the lower concentration of E. coli and greatly decreased $I_{pa}$ indicated that the detection range may possibly be very narrow if using $Fe(CN)_6^{3-}$ as the probe. The result indicated that the interaction between Con A and E. coli occurred on the surface of SM/TQ and the sensing interface of SM/TQ worked successfully.

Con A Binding Characterization

Con A has identical subunits of 237 amino acid residues (MW 27,000). At neutral pH, Con A is predominantly tetrameric with optimal activity. At a pH ranging from 2.0 to 5.5, Con A exists as a single dimer. Two metal ions ($Mn^{2+}$ and $Ca^{2+}$) can bind to Con A, and both are present for carbohydrate binding. Therefore, Con A was used to examine the QCM performance of the SM/TQ modified gold electrode.

To examine the SM/TQ modified gold electrode specificity, ECL, a galactose specific legume lectin; FBS, the most widely used serum in the culturing of cells, tissues, and organs; and BSA, used as a nutrient in cell and microbial culture, were selected as negative controls. As shown in the FIG. 9A, there were negligible frequency changes (ΔF) for the addition of FBS, ECL and BSA. These results indicate that the SM/TQ modified QCM sensor is antigen specific.

FIG. 9B shows the QCM frequency change (ΔF) versus time when different concentrations of Con A were consecutively added to the QCM cell. Initially, the ΔF increased corresponding to more concentration of Con A bound to the SM/TQ modified QCM, and then reached a plateau at 1.0 μM. FIG. 9C displays the correlation between the ΔF and the concentration of Con A. Clearly, at the relatively high concentration, the binding of Con A to the surface bound SM/TQ approaches saturation. These results demonstrate that the SM/TQ modified QCM sensor has high sensitivity and specificity for binding to the Con A.

To obtain the affinity constant of Con A binding with the mannose of SM/TQ, an experimental condition was used in which mass transfer was very fast and was not the rate-limiting step. This condition involved thoroughly stirring the solution using a magnetic stir bar. Under this condition, the binding is the rate-limiting step and the apparent binding affinity for Con A binding to the SM/TQ modified QCM surface can be estimated by using the Langmuir adsorption model. According to the following equation, the mass change at equilibrium was related to the original concentration of Con A (FIG. 9B).

$$\frac{[CON\ A]}{\Delta M} = \frac{[CON\ A]}{\Delta M_{max}} + \frac{1}{\Delta M_{max} K_A} \quad (1)$$

In this equation (1), $\Delta M_{max}$ is the maximum binding amount, ΔM is the measured binding amount at equilibrium, and [Con A] is the original concentration of Con A. As mentioned above, FIG. 9C displays the correlation between the frequency change and the concentration of Con A, and at the relatively high concentration, the binding of Con A to the surface bound SM/TQ approaches saturation. As shown in FIG. 9D, [Con A]/ΔF is proportional to [Con A]. From the linear fit in FIG. 9D, the $K_A$ value was determined to be $4.2 \pm 0.2 \times 10^6$ $M^{-1}$. This result is in good agreement with reported literature values [($5.6 \pm 1.4 \times 10^6$ $M^{-1}$] and the inventors' previous work ($8.7 \pm 2.8 \times 10^5$ $M^{-1}$ (QCM) and ($3.9 \pm 0.2 \times 10^6$ $M^{-1}$ (SPR).

The SM/TQ and Con A binding characterization results confirmed that the SM/TQ modified QCM sensor can be used to detect biomacromolecules (e.g., lectin) and that Con A can be further used as a mediator for the binding between LPS and mannose.

Optimization of Con A-Mediated E. coli LPS and Mannose Binding

Figure 10:
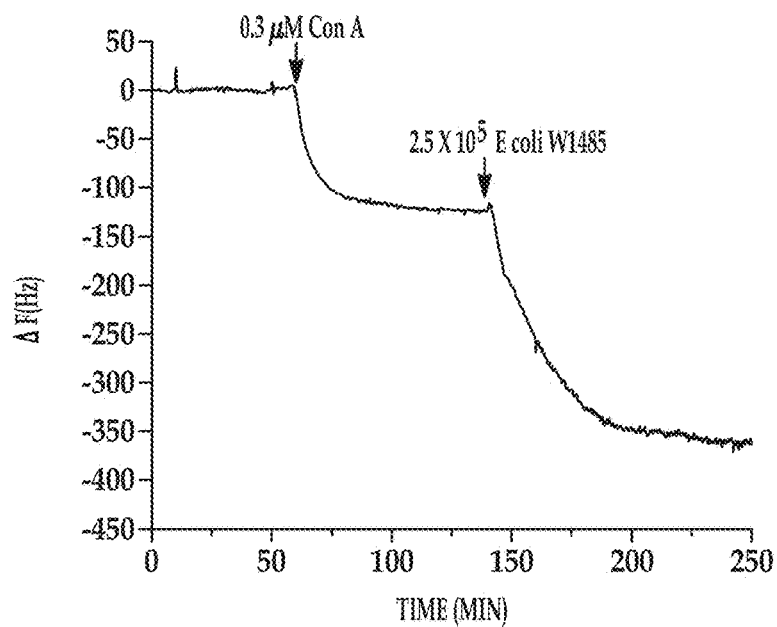
FIG. 10 is a graph depicting frequency change versus time (minutes) when the SM/TQ-QCM sensor was first exposed to 300 nM Con A, followed by the addition of $E.$ $coli$ in 1.0 mL of stirred HEPES buffer (pH 7.4) with 1 mM $Ca^{2+}$ and 1 mM $Mn^{2+}$.

Experimental conditions were studied to demonstrate that the Con A adsorbed on the E. coli surface facilitates the binding of E. coli to the mannose receptor rather than free Con A in the mixture of bacteria that binds to the mannose receptor. To investigate the role of Con A, a low concentration of Con A was first added to the mannose sensor test chamber. The concentration of Con A added was relatively low so that the mannose surface was not saturated based on the Con A/mannose-binding experiment (FIG. 9B) and the surface still had a plethora of available mannose-binding sites. After the Con A-mannose binding reached equilibrium, E. coli was added. At this time, small amounts of free Con A in the bulk solution will facilitate the binding of E. coli to the mannose receptor. As shown in FIG. 10, the addition of 300 nM Con A to the SM/TQ modified QCM sensor generated about ΔF of 125-Hz at equilibrium. The subsequent addition of $2.5 \times 10^5$ of E. coli provided a large binding signal (250 Hz). This result shows that the presence of Con A in the binding solution leads to signal enhancement. It is believed that Con A in the binding solution aggregates on the E. coli bacterial walls through binding to the glucose unit in their O-antigen structures, which promotes the formation of rigid adhesion onto SM/TQ modified QCM sensor.

Figure 11:
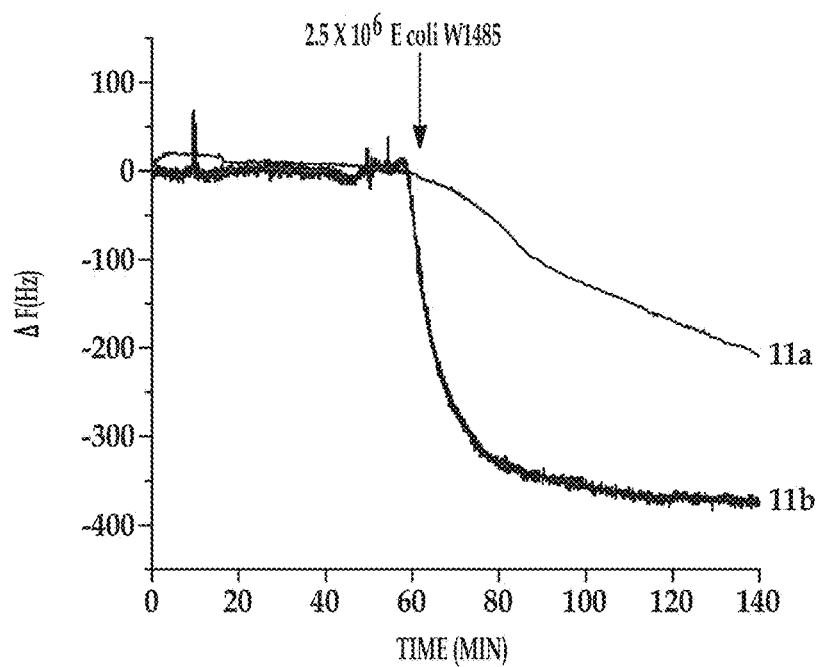
FIG. 11 is a graph depicting frequency change versus time (minutes) when the SM/TQ-QCM sensor, pretreated with Con A, was exposed to $E.$ $coli$ in 1.0 mL of stirred HEPES buffer with pH 5.0 (11a) and pH 7.4 (11b) with 1 mM $Ca^{2+}$ and 1 mM $Mn^{2+}$.

To further confirm the multivalent binding property of Con A to E. coli, the SM/TQ modified QCM sensor, after incubation with 300 nM Con A, was exposed to solutions containing E. coli in buffer with pH 5.0 and 7.4. The results are shown in FIG. 11, where curve 11a is at pH 5.0 and 11b is at pH 7.4. As shown in curve 11a, when the Con A/SM/TQ modified gold electrode was exposed to solutions containing E. coli with pH 5.0, the QCM generated ΔF of about 220 Hz. When the Con A/SM/TQ modified gold electrode was incubated with the same concentration E. coli in pH 7.4 buffer, the QCM provided a larger ΔF of 375 Hz. One possible reason for these results is that Con A exists as a dimer of two covalently linked subunits with an approximate molecular weight of 55,000 Da between pH 2 and 5.5, whereas at pH values above 5.5, a tetramer with a molecular weight of 110,000 Da predominates. The result of FIG. 11 confirmed the multivalent binding property of Con A in the 10 mM HEPES buffer with pH 7.4, which results in an enhancement of the sensor response.

EQCM Measurements

This example demonstrates the fabrication and validation of the mannosylated polythiophene biointerface for detection of Gram-negative bacteria E. coli by combined EQCM methods, as summarized in FIGS. 4A (direct detection) and 4B (lectin-mediated detection). More particularly, the detection of E. coli via binding of SM/TQ with the type 1 pili protein directly (carbohydrate sensor, FIGS. 2 and 4A) or upon binding of LPS on the bacterial surface via the Con A bridge at the SM/TQ modified gold electrode (carbohydrate-lectin sensor, FIGS. 3 and 4B) was characterized by electrochemical and QCM readouts. The use of a thiophene biointerface enables the flexibility of control of the polythiophene polymerization process and the rapid construction of an array of carbohydrate functionalized biointerfaces for subsequent assays, with two distinguishable biomarkers (pili proteins and LPS) at the bacterial surface.

The EQCM measurement was performed with the single SM/TQ modified gold electrode of QCM, rather than dual QCM electrodes in which a reference nonmodified electrode is simultaneously used in each experiment. The QCM and electrochemical measurements were made in series using the systems previously described.

EQCM Detection of E. coli via Pili-Mannose Binding

Figure 12A:
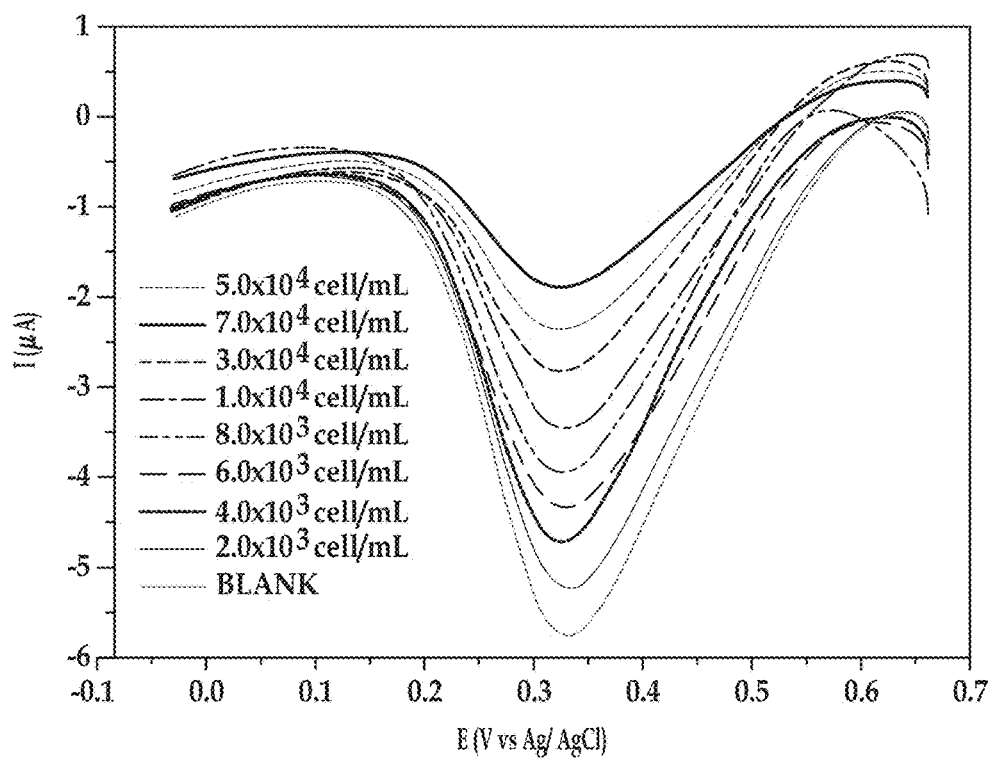
FIG. 12A is a graph depicting the square wave voltammetry (SWV) responses of an SM/TQ modified gold electrode after incubation with different concentrations of $E.coli$ cells/mL.
Figure 12B:
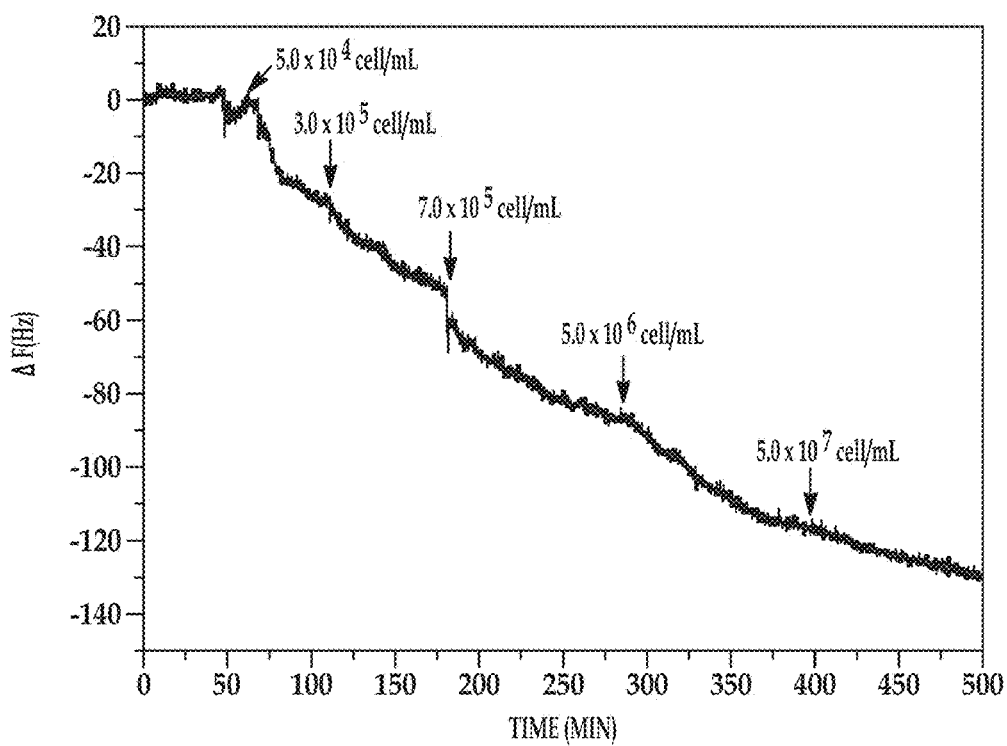
FIG. 12B is a graph depicting frequency change versus time (minutes) when SM/TQ-QCM sensor was exposed to different concentrations of $E.$ $coli$ cells in HEPES buffer (pH 7.4) with 1 mM $Mn^{2+}$ and 1 mM $Ca^{2+}$.

There are two important elements in the Gram-negative bacterial cell wall for specific bacterial adhesion. One is carbohydrate binding lectins in many bacteria, usually in the form of fimbriae (or pili). The other one is glycoconjugates, called LPS, in all Gram-negative bacterial cell walls, which are present in the outer monolayer of the outer membrane along with phospholipids (inner leaflet) and proteins, which are lectin binding sites. The glycosylated polythiophene biointerface disclosed herein can explore both types of these binding activities. In the first case, the binding between E. coli and mannose receptor on the SM/TQ surface can occur, which provides simultaneous detection signals for both electrochemical and QCM readouts, as shown in FIGS. 12A and 12B. This direct binding of cells leads to the formation of an adsorption layer, which in turn should lead to a change at the electrode interface. The adsorption layer hinders the electron transfer process of quinone/thiophene moieties in the conducting polymer modified electrode, which quantitatively depends upon the binding sites occupied as well as the binding strength of each individual interaction. This is consistent with a previously reported partially blocked electrode and generates changes of electrochemical signals.

It has been shown experimentally that square wave voltammetry (SWV) is more sensitive than cyclic voltammetry (data not shown). Therefore, SWV was used to characterize the biointerface for determination of E. coli (FIG. 12A) via electrochemical readout. When an increasing number of E. coli cells were introduced into the sensor chamber, a consistent decrease in the peak current was observed, which indicates a signal OFF readout mechanism. By using the electrochemical approach, E. coli was detected in the concentration range of $2.0 \times 10^3$ cells/mL to $7.0 \times 10^4$ cells/mL with a detection limit calculated according to S/N=3 to be $8.0 \times 10^2$ cells/mL.

QCM measurements were performed to evaluate the same binding process. For these measurements, the SM/TQ-QCM sensor was exposed to different concentrations of E. coli cells in HEPES buffer (pH 7.4) with 1 mM $Mn^{2+}$ and 1 mM $Ca^{2+}$. The results are shown in FIG. 12B. The cells are soft structures; and their attachment to the interface can generate viscoelastic changes at the interface that can confuse the mass sensing results. In most cell based studies, frequency-dissipation analysis or frequency-resistance analysis is typically used to exclude viscoelastic changes. In this example, the frequency-resistance analysis was utilized.

Figure 13:
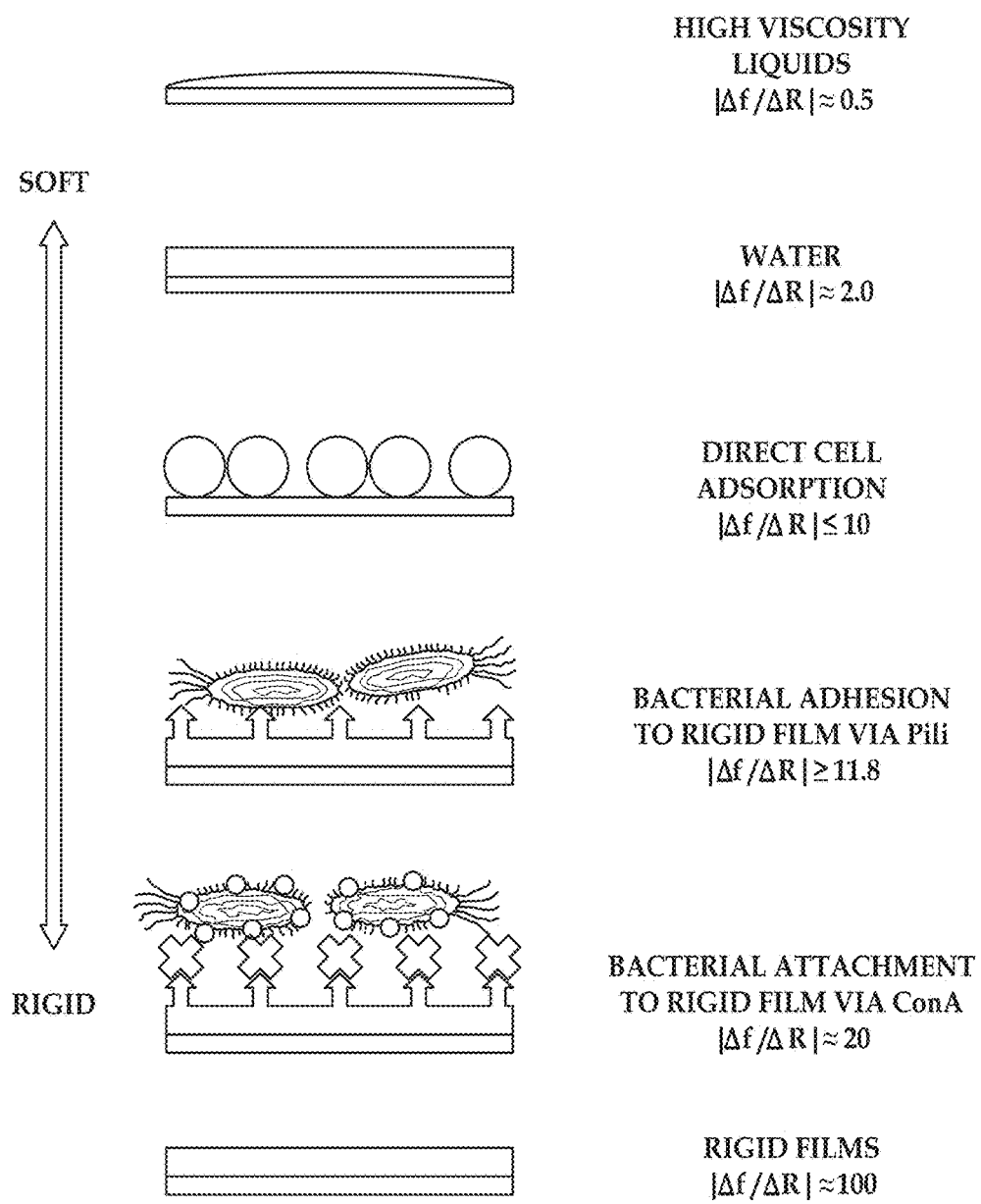
FIG. 13 is a schematic illustration depicting a comparison of typical soft and rigid interfaces with the interfaces of the example biosensors disclosed herein, and their corresponding frequency-resistance ratios.

FIG. 13 gives a comparison of such analyses for typical soft and rigid interfaces and their corresponding $|\Delta f_0/\Delta R_1|$ values. When a highly viscous fluid (e.g., silicone oils, ionic liquids) is present at the QCM interface, the damping resistance of the acoustic waves is too high, thereby decreasing the decay length. Thus, the resulting $|\Delta f_0/\Delta R_1|$ values are less than 1 (e.g., 0.2 for silicone oil). When the interface is changed to typical fluids such as water, the $|\Delta f_0/\Delta R_1|$ value is typically around 2.0, which indicates that the resistance changes are very high in comparison to mass changes. This value can be increased even further (e.g., to about 4.1) by increasing the roughness of the surface. This clearly shows that the rigidity of the interface is related to the slip behavior of the contacting fluid or film. When we increase the roughness of the surface, we decrease the slip, thereby increasing the value of $|\Delta f_0/\Delta R_1|$, even for the real fluids. Thus, the fluids can also be made to show a bit of rigidity by roughness manipulations.

For the direct cell adsorption on the QCM surface, with the cells being very soft structures, the slip effect is reasonably large, and thus the $|\Delta f_0/\Delta R_1|$ values are still less than 10. Even in that case, it has been shown that the external load (e.g., cancer cells), if connected to the interface, can be sensed by the QCM while they are lying outside the decay length of the acoustic wave. However, in this example, the cells are not directly attached to the QCM. Rather, there is a polymer film, which is typically rigid. When these films are produced by the electrochemical polymerization, the homogeneity of the films makes them even more rigid than those polymer films made by casting or spin coating. Polymer surfaces are much rougher than the QCM surface, thereby decreasing the slip and increase the rigidity of the interface. When the bacterial cells are attached to this film via the pili on their surface, the resulting interface is not completely rigid. However, because of the presence of string-like attachments, $|\Delta f_0/\Delta R_1|$ values are ≥11.8 (see FIG. 14, where the experiments were performed with the same conditions as FIG. 12B), which is larger than reported threshold values. At this value, the damping resistance is so small that the viscoelastic effects, despite their presence, can be ignored. Thus, the cells can be detected by the QCM while lying outside the extinction depth of the acoustic wave.

Figure 15:
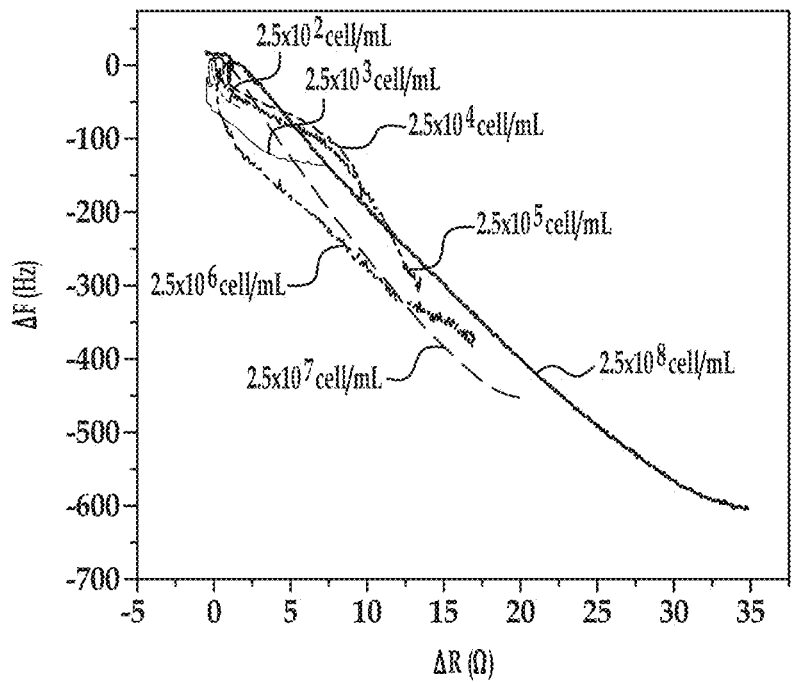
FIG. 15 is a graph depicting the relationship between ΔF vs. ΔR after a Con A/SM/TQ-QCM sensor (i.e., the SM/TQ-QCM sensor with Con A bound thereto) was exposed to different concentrations of $E.$ $coli$ in HEPES buffer (pH 7.4) with 1 mM $Mn^{2+}$ and 1 mM $Ca^{2+}$.
Figure 16A:
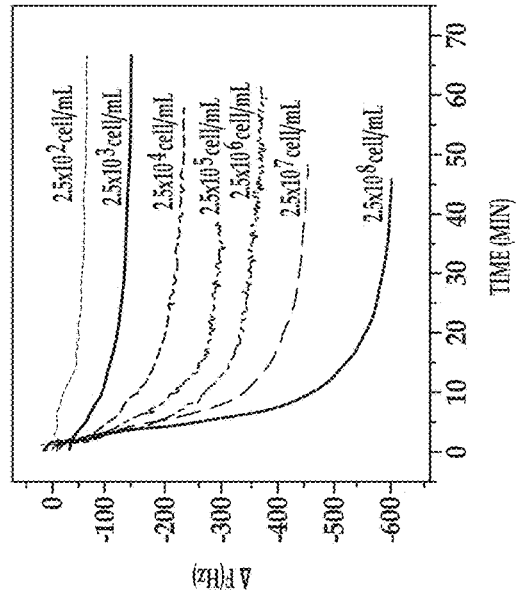
FIG. 16A is a graph depicting the square wave voltammetry (SWV) responses of an SM/TQ modified gold electrode after incubation with 300 nM Con A and different concentrations of E. coli.
Figure 16B:
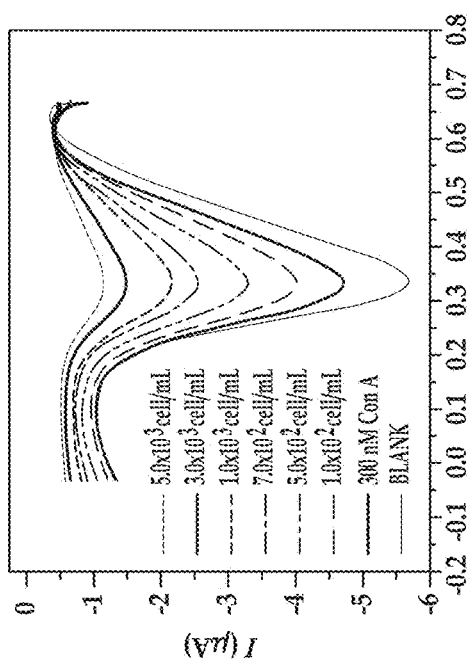
FIG. 16B is a crystal quartz microbalance (QCM) frequency change versus time curve when Con A/SM/TQ electrodes were exposed to different concentrations of E. coli in 1 mL of stirred HEPES with 1 mM $Mn^{2+}$ and 1 mM $Ca^{2+}$.

Moving onto bacterial binding to the same polymer film via Con A mediation, the bacterial attachment is in glued-like fashion, making it even more rigid, thereby increasing the $|\Delta f_0/\Delta R_1|$ values to ~20 (see FIG. 15, where the experiments were performed with the same conditions as FIG. 16B). The changes (%) in damping resistances when SM/TQ or Con A/SM/TQ modified gold electrodes were exposed to different concentrations of E. coli cells were determined (see Table 1).

TABLE 1

Figure 14:
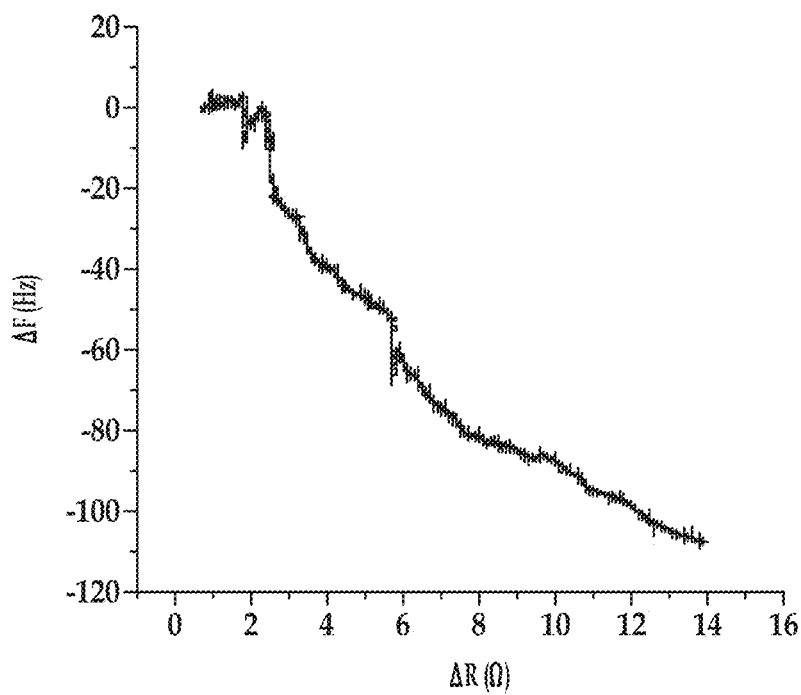
FIG. 14 is a graph depicting the relationship between ΔF vs. ΔR when the SM/TQ-QCM sensor was exposed to different concentration of $E.$ $coli$ cells in HEPES buffer (pH 7.4) with 1 mM $Mn^{2+}$ and 1 mM $Ca^{2+}$.

Changes (%) in Damping Resistances and the slopes of ΔF vs. ΔR for Experiments Shown in FIGS. 14 and 15

| | $R_0$ (Ω) | ΔR (Ω) | $\Delta R/R_0$ (%) | Slope of ΔF vs. ΔR (Hz $\Omega^{-1}$) | Concentration of E. coli (cell/mL) |
|---|---|---|---|---|---|
| SM/TQ | 256 | 14 | 5.4 | 11.8 | $5 \times 10^7$ |
| ConA/SM/TQ | 308 | 1.5 | 4.87 | 30.4 | $2.5 \times 10^2$ |
| | 310 | 7.3 | 2.4 | 17.1 | $2.5 \times 10^3$ |
| | 313 | 9.7 | 3.1 | 29.5 | $2.5 \times 10^4$ |
| | 307 | 13 | 4.2 | 29.5 | $2.5 \times 10^5$ |
| | 309 | 17 | 5.5 | 19.7 | $2.5 \times 10^6$ |
| | 312 | 20 | 6.4 | 28 | $2.5 \times 10^7$ |
| | 319 | 34.5 | 10.8 | 21.2 | $2.5 \times 10^8$ |

From this data, it can be seen that the values of $\Delta R/R_0$ are smaller than 15%. This suggests that the bacterial attachment can be considered as rigid, rather than a viscoelastic behavior. These results also show that the Con A/SM/TQ film is more rigid than the SM/TQ film and that the binding between LPS of E. coli and Con A is stronger than that of fimbriae of E. coli and mannose attached to the gold surface. However, this theoretical threshold $|\Delta f_0/\Delta R_1|$ value (i.e., 11.6 for 10 MHz QCM) cannot be considered as the digital switch. Rather, the above analysis gives an indication that there is a gradual change in this value while moving from a soft to more and more rigid interfaces. At the threshold level, there is no sudden shift in behavior, and the viscosity effects are quite minimal.

It has been shown that if the attachment of the cells to the interface is intact, the cells can be detected while lying outside the decay length of the acoustic wave generated by QCM. Thus, in this case, although the length of the pili is comparable to the extinction depth of the acoustic wave, the anchoring of the cells at a rigid polymer film by the pili will not significantly affect their detection by the QCM. Despite all these reasons to believe that the responses shown in this example are predominantly due to mass changes at the interface, the viscosity effects might be present and thus cannot be considered as true Sauerbrey's responses. In this example, possible error in the calculation has been circumvented by avoiding the application of Sauerbrey's equation in calculating the affinity constant and by using the signal versus the concentration of cells for calibration.

For the quantitative analysis, different concentrations of E. coli were introduced into the measuring chamber and the frequency shift of the QCM was recorded as shown in FIG. 12B. With increasing number of E. coli cells, the shift in frequency increases as well, indicating a signal ON readout mechanism. By using this approach, bacteria E. coli was detected in a different concentration range than the electrochemical approach, i.e., $5.0 \times 10^4$ cells/mL to $5.0 \times 10^7$ cells/mL with a detection limit calculated according to S/N=3 as $1.7 \times 10^4$ cells/mL. This linear range is broader than that in our previous work (i.e., $2.9 \times 10^7$ cells/mL to $2.7 \times 10^8$ cells/mL) using mannose SAM as the glycosurface, thereby indicating that the SM/TQ as the biointerface has higher mannose binding sites than those in mannose SAM.

Theoretically speaking, if QCM is regarded as a mass sensor, the binding of the bacterial cells should generate a much larger response considering the length and weight of one E. coli are about 2 μm and $1 \times 10^{-12}$ g, respectively. The theoretical mass of a close packed monolayer of E. coli at a 0.22 cm² gold electrode is about 125 μg. However, the observed response is a few orders smaller than this value. The plausible explanation for such a smaller response is that the surface area of the gold electrode is only a rough estimate of the polythiophene biointerface area. Furthermore, the QCM mass sensor senses surface binding phenomena and requires rigid and tight binding. As discussed earlier, the fimbriae-mediated adhesion is relatively weak and flexible. With high mobility of the bacteria, it creates a large freedom of movement of the bacterial cells on the QCM surface. This weak and flexible binding of the fimbriae to the mannose may also result in a displacement of one species with another. Consequently, the surface is only a temporary host to the E. coli and the net change of mass is very small. This is why the measured mass was often smaller than expected when QCM was used to detect big targets such as bacteria. Therefore, the second type of recognition events, which are based on tight and rigid binding via Con A mediated sandwich assay, were also evaluated.

EQCM Detection of E. coli via Con A Mediated LPS-Mannose Binding

As discussed above, a binding on the sensor surface which is not rigid is not as sensitive for bacterial detection, especially if the mass sensitive sensing mechanism is utilized. Thus, the key principle in these measurements is to ensure adequate bacterial binding by using recognition molecules with high affinity and multiple binding sites. Distinct LPS structures present on Gram-negative bacteria are particularly advantageous in this regard that can be recognized by lectins. For this purpose, lectin Con A was used as an E. coli adhesion promoter to strongly attach E. coli to the mannose, so a rigid binding layer would be formed on the electrode surface, thereby generating the Con A/SM/TQ interface depicted in FIG. 4B. FIGS. 8A, 8B, and 9A-9D depict similar characterization data for fabricating the Con A/SM/TQ (the carbohydrate-lectin sensor) interface and FIGS. 10 and 11 depict the characterization data of Con A binding with the SM/TQ interface to obtain the optimum conditions.

The Con A-modified surface was exposed to different concentrations of E. coli cells and the SWV measurements were performed. The results are shown in FIG. 16A. For the Con A/SM/TQ mode, the peak currents decreased upon increasing of the concentration of E. coli in the concentration range of $1.0 \times 10^2$ cells/mL to $5.0 \times 10^3$ cells/mL and the calculated detection limit was 25 cells/mL. This result, on one hand, shows a 32-fold enhancement in the detection limit with a totally different linear detection range, but also supports the fact that a tight binding of the target is beneficial for the electrochemical measurements as well.

In order to perform the QCM measurements using this binding mechanism, the SM/TQ modified QCM sensor was first exposed to the 300 nM Con A solution for 1 hour to reach binding equilibrium as a Con A/SM/TQ modified QCM sensor. This step ensures consistency between each experiment, and then E. coli samples ranging from $2.5 \times 10^2$ cells/mL to $2.5 \times 10^8$ cells/mL were injected into the Con A/SM/TQ modified QCM sensor chambers, which also contained 1 mL of 10 mM HEPES buffer with 1 mM $Mn^{2+}$, 1 mM $Ca^{2+}$. Much faster and larger responses were observed for this interface as compared to the SM/TQ only interface (comparing FIG. 16B with FIG. 12B). The detection limit was calculated to be 50 cells/m L, with three decades wider detection range than the early SM/TQ modified QCM sensor.

Figure 17A:
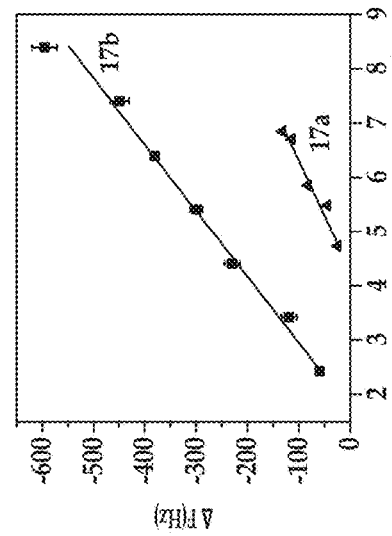
FIGS. 17A and 17B are calibration curves of sensor signals drawn against logarithm of E. coli concentrations, where
Figure 17B:
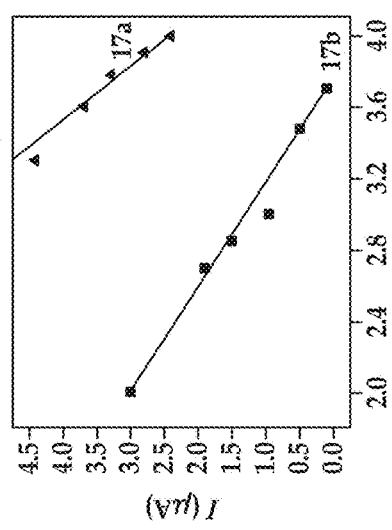

For a quantitative comparison, calibration curves were drawn for all these measurements using the plot of sensor signals against logarithm of bacterial cell concentrations. FIGS. 17A and 17B show the well fitted linear curves for both the electrochemical (FIG. 17A) and QCM data (FIG. 17B), whereas the (17a) and (17b) notations represent the SM/TQ and Con A/SM/TQ interfaces, respectively. From FIGS. 17A and 17B, three important conclusions can be drawn.

First, from the comparison of (17a) and (17b) curves both in the electrochemical as well as in QCM data, it is quite clear that the signals are much stronger for the Con A/SM/TQ interface, and thus, the detection limit for this interface is 32-fold lower for electrochemical measurements and more than 300-fold lower for QCM measurements, as detailed in Table 2.

TABLE 2

Comparison of the Analytical Performance of Two Orthogonal Sensing Interfaces - Direct Binding and Con A Mediation

|  |  | Mannose/E. Coli (Direct binding) | Mannose/Con A/E. Coli (Con A Mediated Binding) |
|---|---|---|---|
| Linear Range | SWV | $2.0 \times 10^3$ to $1.0 \times 10^4$ cells/mL | $1.0 \times 10^2$ to $5.0 \times 10^3$ cells/mL |
|  | QCM | $5 \times 10^4$ to $5 \times 10^7$ cells/mL | $2.5 \times 10^2$ to $2.5 \times 10^8$ cells/mL |
| Sensitivity | SWV | −3.33 (μA/log(cells/mL)) | −1.71 (μA/log(cells/mL)) |
|  | QCM | −49.52 (Hz/log(cells/mL)) | −81.79 (Hz/log(cells/mL)) |
| Detection Limit | SWV | $8.0 \times 10^2$ cells/mL | 25 cells/mL |
|  | QCM | $1.7 \times 10^4$ cells/mL | 50 cells/mL |

This significant increase in sensitivity of the interface is due to rigid binding of the bacteria via LPS on its surface and by using Con A mediation as described earlier. One major issue that should be considered in this type of bacterial detection is the antigenic or phase variation. As a result of this phase variation, type 1 E. coli bacteria might shift from a fimbriated phase to a nonfimbriated phase and back spontaneously, which might affect the fimbriated E. coli attachment. Various environmental factors, such as centrifuge, can also change the phase of the type 1 E. coli bacteria from a fimbriated phase to a nonfimbriated phase. Therefore, in order to accommodate these variations in the sensor, and to detect multiple types of bacteria at the same time, the bacterial pili must also be targeted for binding, which can be done by the direct binding of the pili to the mannosylated interface. The data from these measurements and from the LPS binding processes can then be fed into multidimensional data analysis tools in order to draw conclusions about the nature and type of bacteria.

Second, from the comparison of the electrochemical data (FIG. 17A) and QCM data (FIG. 17B) for both SM/TQ and Con A/SM/TQ interfaces, it is again quite clear that the range of analysis is quite different; rather orthogonal for the two methods. For the SM/TQ interface, the logarithmic range for the SWV data starts from about 3 and goes until 4, whereas for the same interface the logarithmic range is about 4.5 to 7 for the QCM data. This depicts that the overall range is broadened from 3 to 7 by utilizing these orthogonal methods, which otherwise was not that simple. The electrochemical method is a signal OFF approach, thus providing at least a signal at logarithmic range of 4, and cannot go further up in concentration unless a new interface is designed. Contrarily, the QCM is a signal ON approach and cannot measure less than 4.5 of logarithmic concentration. In the similar manner, the logarithmic ranges in the case of the ConA/SM/TQ interface (17b curves) are 2 to 3.7 and 2.4 to 8 for electrochemical and QCM detection, respectively. Thus, it is evidently shown that the proposed strategy can be used to increase the detection dynamic range of the two orthogonal sensing platforms, thereby enhancing the overall sensing performance.

Figure 8B:
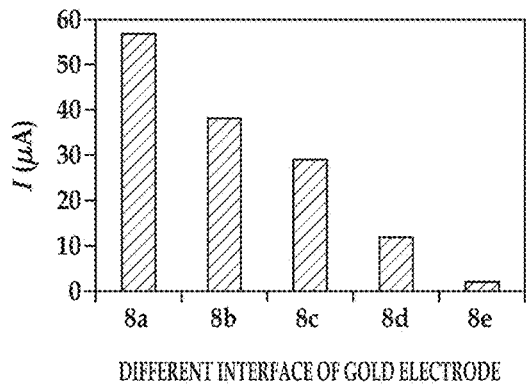
FIG. 8B is a bar graph illustrating the anodic peak current ($I_{pa}$) for 8a through 8e.

Moreover, at many points, the two sensing mechanisms supplement each other as well in terms of detection range. For example, the logarithmic range of 2.4 to 3.7 can be covered by both electrochemical and QCM sensor based on Con A/SM/TQ interface. These points can serve as an internal validation system, thereby eliminating the need for expensive external validations. The reliability of each and every measurement is enhanced too, in this manner. Furthermore, as shown in FIGS. 8A and 8B, if $Fe(CN)_6^{3-}$ is used as the electrochemical probe for the SM/TQ modified electrode, the $I_{pa}$ of $Fe(CN)_6^{3-}$ continuously decreased during the process of the sensor fabrication, particularly, when the E. coli bound to the SM/TQ modified gold electrode pretreated by the Con A. The result indicates that an SM/TQ modified gold electrode can be used to detect E. coli using $Fe(CN)_6^{3-}$ as well. However, the lower concentration (500 cells/mL) of E. coli and greatly decreased Ipa (from 12 µA Ma to 2.1 µA) indicated that the detection range of E. coli possibly is very narrow if using $Fe(CN)_6^{3-}$ as a probe. Therefore, it can be concluded that this new interface with built-in electrochemical probe has much better prospects in bacterial detection.

Third, in comparison to the Con A/SM/TQ sensor, the SM/TQ sensor exhibited much lower sensing performances, both sensors are still better than those for previously reported interfaces and protocols being used. Table 3 shows the performance evaluation of this sensor and the comparative analysis of the other techniques reported.

TABLE 3

Comparison of Techniques for the Detection of E. Coli

| Reference | E. Coli Strain | Assay Principle | Detection Limit (LOD) (cells/mL) | Linear Ranges (cells/mL) |
|---|---|---|---|---|
| Akanda, M., et al. | O157:H7 | Electrochemical ELISAs combined with redox cycling | $10^3$ | $10^3$-$10^8$ |
| Tlili, C., et al. | B | Loop-mediated isothermal amplification with EIS | 800 (EIS) 100 (LAMP) | $10^3$-$10^9$ (EIS) $10^2$-$10^9$ (LAMP) |
| Maalouf, R., et al. | CIP 76.24 | EIS and SPR | $10^7$ (SPR) 10 (EIS) | |
| Mannoor, M., et al. | O157:H7 | Antimicrobial Peptides array | $10^4$ | $10^4$-$10^7$ |
| Mannoor, M., et al. | O157:H7 | Chemiluminescence flow-through DNA microarray | 136 (stop circle 35) 4000 (stop circle 30) | $10^2$-$10^4$ (stop circle 35) $10^5$-$10^7$ (stop circle 30) |
| Shabanim A., et al. | K12 | T-4 modified microarrays with EIS | 100 | $10^2$-$10^8$ |
| This Example | W1485 | SM/TQ - SWV | 800 | $2.0 \times 10^3$ to $1.0 \times 10^4$ |
| This Example | W1485 | Con A/SM/TQ - SWV | 25 | $1.0 \times 10^2$ to $5.0 \times 10^3$ |
| This Example | W1485 | SM/TQ - QCM | $1.7 \times 10^4$ | $5 \times 10^4$ to $5 \times 10^7$ |
| This Example | W1485 | Con A/SM/TQ - QCM | 50 | $2.5 \times 10^2$ to $2.5 \times 10^8$ |
| This Example | W1485 | Con A/SM/TQ - $Fe(CN)_6^{3-}$ as probe | 500 | |

The detection limit of the sensors disclosed herein is many fold lower than the value of 1000 cfu/mL of E. coli O157:H7 obtained from a peptide based impedimetric biosensor, and is even lower than 136 cells/mL of E. coli O157:H7 obtained from a DNA based chemiluminescence biosensor. The high sensitivity obtained by the example sensors may be ascribed to employing Con A as the mediator for the binding between LPS of E. coli and mannose and TQ as the signal producing compound.

Tables 2 and 3 list the limits of detection (LOD) obtained using antibody or DNA recognition elements as reported in the literature and the reliable quantitative detection via the two methods we used (carbohydrate or carbohydrate/lectin recognition elements). From Table 3, the detection limit and linear response range of this SM/TQ modified QCM sensor using Con A as mediator are impressive in comparison with the detection limit of $8\times10^2$ cfu/mL obtained from the bacteriophage-impedimetric/loop-mediated isothermal amplification dual-response biosensors, the detection limit of 1000 cfu/mL obtained from the electrochemical sensor using enzymatic amplification combined with electrochemical-chemical-chemical redox cycling, and the detection limit of the QCM sensor combined with the self-assembled thiol modified mannose monolayers previously developed.

The present system is also comparable with other sensors or sensing methods developed. Although the detection limit of the SM/TQ modified QCM sensor is higher than that of the above electrochemical sensor, the carbohydrate QCM sensor has large linear range. Therefore, the SM/TQ modified interface can be used extensively for detection of biomacromolecule combined QCM and electrochemical techniques. The high sensitivity and broad response range obtained in this example may be ascribed to the new SM/TQ biointerface designed, which has many advantages, such as the following: (1) compared with the monomolecular layer monosaccharide reported previously, the multilayer of the conducting polymer with a three-dimensional structure could bring in more molecular recognition elements to improve the sensitivity of the sensor. (2) The cross-linked conducting polymer creates unique multivalent recognition sites that complement the analytes in chemical functionality and in size and shape and prevent the nonspecific adsorption of protein to the substrate and ensure that only specific interactions between soluble proteins or bacteria and immobilized ligands occur. (3) Con A, a multivalent specific binding lectin, is used to increase the binding of E. coli on the mannose-coated sensor, and a sensitive response is achieved.

Sensor Specificity

Figure 18A:
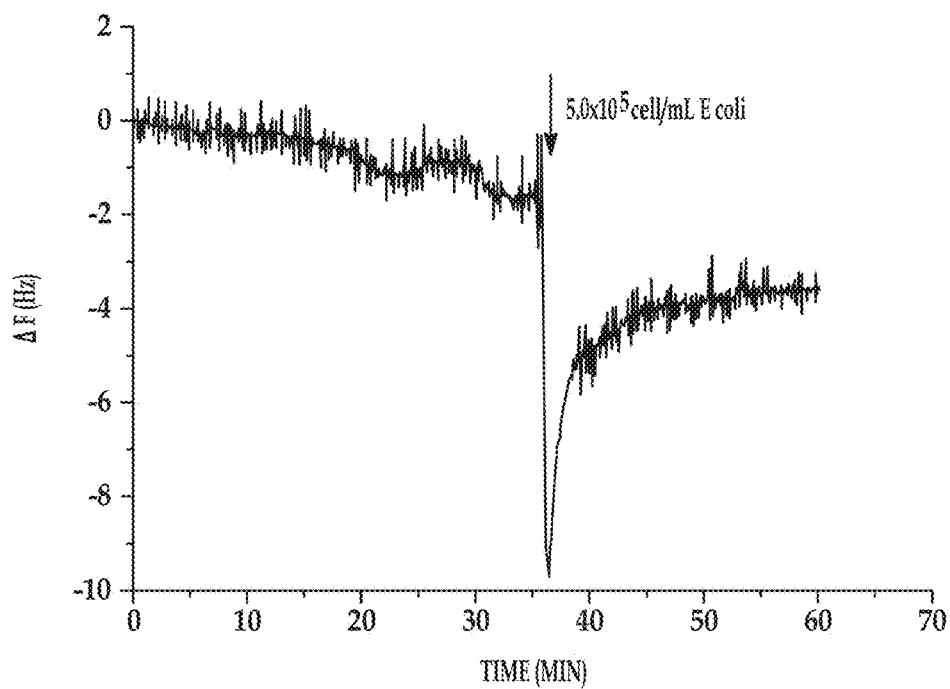
FIGS. 18A and 18B are graphs depicting frequency change versus time (minutes) when the TQ modified gold electrode was (18A) exposed to $5.0 \times 10^5$ cell/mL E. coli in HEPES buffer (pH 7.4) with 1 mM $Mn^{2+}$ and 1 mM $Ca^{2+}$, and (18B) incubated in 300 nm Con A and then exposed to $5.0 \times 10^5$ cell/mL E. coli in HEPES buffer (pH 7.4) with 1 mM $Mn^{2+}$ and 1 mM $Ca^{2+}$.
Figure 18B:
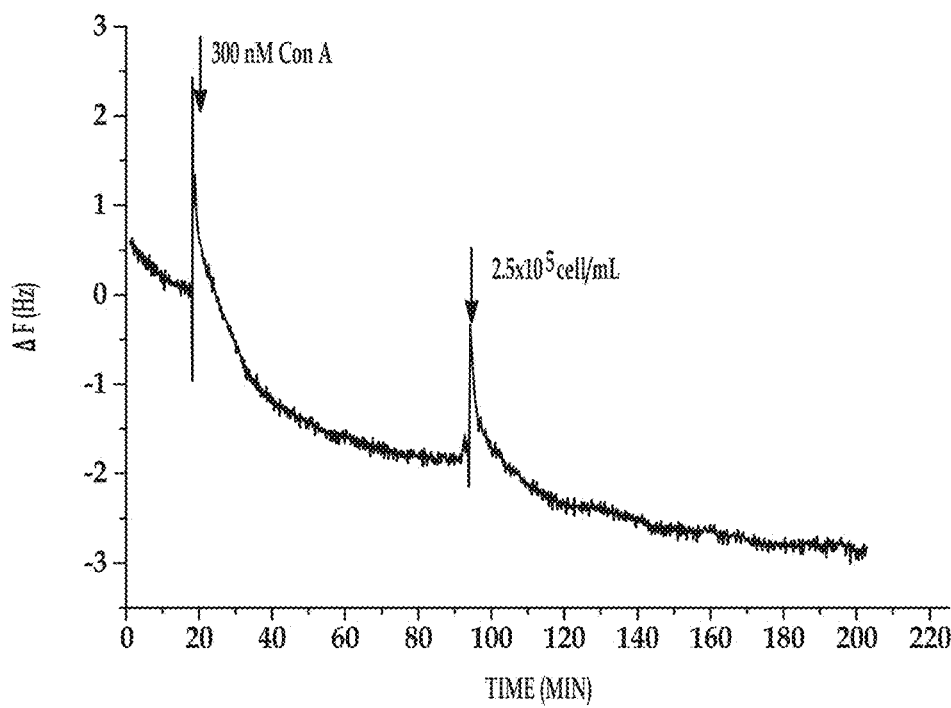

Several control experiments were performed to characterize sensor specificity. The TQ modified gold electrode (no mannose attached to the TQ modified gold electrode) was first tested. For one example, the TQ modified gold electrode was exposed to $5.0\times10^5$ cell/mL E. coli in HEPES buffer (pH 7.4) with 1 mM $Mn^{2+}$ and $Ca^{2+}$. For another example, the TQ modified gold electrode was incubated with 300 nM Con A, and then was exposed to $2.5\times10^5$ cell/mL E. coli in HEPES buffer (pH 7.4) with 1 mM $Mn^{2+}$ and $Ca^{2+}$. As shown in FIGS. 18A and 18B, the QCM gave little frequency change with or without Con A present when E. coli was added. In contrast, when the SM/TQ modified gold electrode was first exposed to 300 nM Con A solution for about 1 hour and formed a Con A/SM/TQ modified gold electrode, E. coli W1485 was added with a final concentration of $2.5\times10^5$ cells/mL and generated a large signal response (about 240 Hz) (FIG. 19, curve 19a), which was about 2.3 times larger than the adhesion of $2.5\times10^7$ cells/mL of E. coli BL(21)DE onto the SM/TQ modified gold electrode (about 104 Hz, FIG. 19, curve 19b). The possible reason is that E. coli BL(21)DE is a descendant of the E. coli B strain, which is similar to the K strain. E. coli O86 was used additionally to examine the specificity of the above system. With the same experimental condition as for the FIG. 19, curve 19a, a very small signal (39 Hz) was observed for the addition of $2.5\times10^7$ cells/mL of E. coli O86 (FIG. 19, curve 19c) because the O-antigen of E. coli O86 contains no Con A specific binding glucose, Nacetylglucosamine, or mannose. S. aureus, a Gram-positive bacterium, was further used as a negative control. When S. aureus was added to the Con A pretreated SM/TQ modified gold electrode, only a negligible frequency change was detected, which resulted from no LPS in the bacterial wall of S. aureus (FIG. 19, curve 19d).

Figure 19:
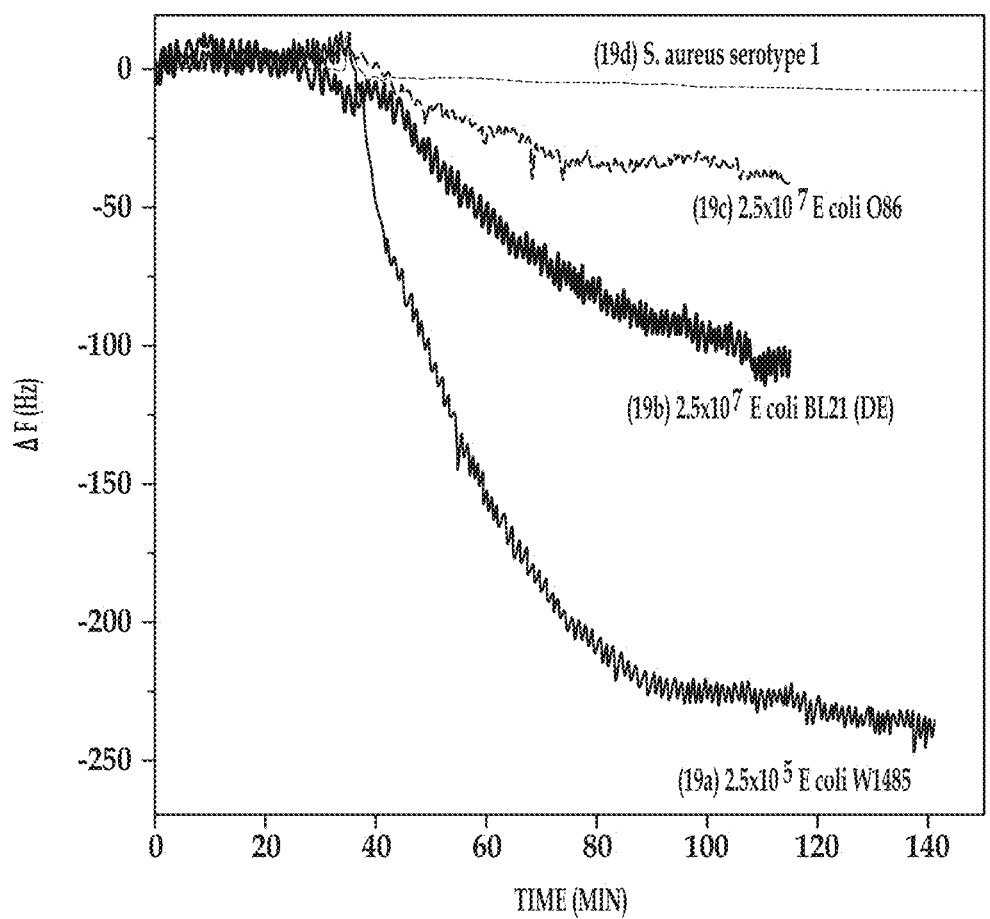
FIG. 19 is a graph depicting a comparison of sensor specificity, where different electrodes (Con A pretreated mannose electrodes with Con A in the binding solution) were exposed to (19a) $2.5 \times 10^5$ E. coli W1485, (19b) $2.5 \times 10^7$ E. coli BL21 (DE), (19c) $2.5 \times 10^7$ E. coli O86, and (19d) S. aureus serotype 1, where (19b), (19c), and (19d) were added to the Con A pretreated mannose electrode with Con A in the binding solution; all the test chambers contained 1.0 mL of stirred HEPES buffer (pH 7.4) with 1 mM $Mn^{2+}$ and 1 mM $Ca^{2+}$.

The control experiments in FIG. 19 indicated that the extracellular matrix did not interfere with the E. coli detection. The results also verified that Con A in the binding solution aggregated onto the E. coli W1485 wall and thus enhanced the sensitivity and specificity for mannose binding with E. coli W1485 by promoting the formation of rigid attachment to the mannose modified QCM surface.

Conclusions for Example 1

The results in this example show an integrated approach to address the concerns of carbohydrate based biosensors for bacterial detection with the following new strategies: (1) using polythiophene fused quinone moieties for carbohydrate biointerface fabrication for bacterial detection via pili; (2) enhancing bacterial recognition by combining it with an additional binding event, i.e. lectin-LPS binding, thereby enhancing the sensitivity and limit of detection; (3) using two orthogonal label-free transducers for widening the dynamic range of detection and to introduce the internal validation. The sensor fabricated in this example showed the lower detection limits of 25 cells/mL (for SWV) and 50 cells/mL (for QCM), as well as better selectivity and stability as compared to the presently available technologies. By taking advantage of such a polyvalent binding situation in carbohydrate based polymers and the built in electrochemical transduction of conductive polymers, we were able to substantially minimize possible cross-reactivity that significantly enhanced the specificity and sensitivity of detection. The glycosurface chemistry, with the flexibility of the electrochemical synthesis of polythiophene containing fused quinone moieties alongside the inherent quick, clean, high fidelity characters of coupling chemistry presented here, can be used to rapidly generate an array of sugar biointerfaces for subsequent assay with proteins. Thus, the example biosensors disclosed herein can be advantageous for multiple directions of sensor development. Combining such a biointerface with an appropriate electrochemical and QCM transducer yields sensor devices that are highly suitable for the fast, low cost, and straightforward online detection of bacterial analytes and harmful pathogens related to agriculture, the food industry, disease control, and biodefense.

Example 2

Biosensor use in Antimicrobial Susceptibiity Assay

In Example 2, an example of the label free lectin biosensor described in Example 1 was utilized for an antibiotic susceptibility assay. The biosensor utilized a polythiophene interface containing fused quinone moieties glycosylated to form a carbohydrate platform for the immobilization of Concanavalin A (Con A) and is capable of LPS binding measurements via orthogonal quartz crystal microbalance and electrochemical readouts (EQCM). The orthogonal transduction provided cross validation, better sensor sensitivity, and a large dynamic range of the measurements.

Figure 20:
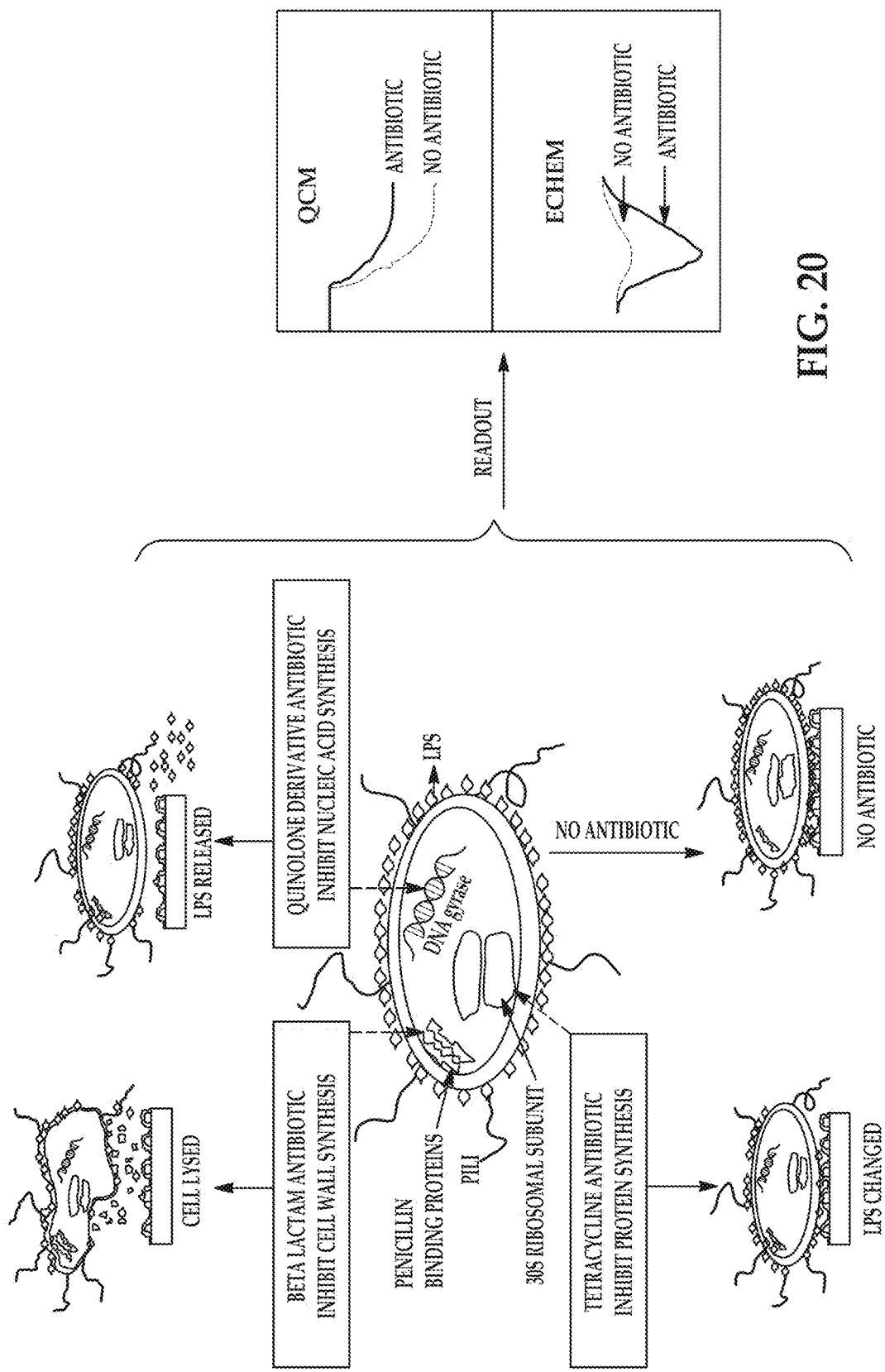
FIG. 20 is a schematic illustration of the mechanisms of action of three antibiotics studied on the bacterial cell wall, the magnitudes of the alterations vary with the type of antibiotics, which affect the bacterial binding to the lectin biosensor.

In this example, the label free lectin biosensor was used for a new antibiotic susceptibility assay by characterizing the antimicrobial activities of various antibiotics (i.e., ciprofloxacin, ceftriaxone, and tetracycline) against Escherichia coli (E. coli) W1485. If the antibiotics have effects on the E. coli, the binding between the LPS of E. coli and the Con A confined to the sensor surface will be affected, which will induce different electrochemical and QCM signal changes, as depicted in FIG. 20. According to these change of signals, the properties of the antibiotics action can be quantified.

In this Example, the label free biosensor allowed for both end point and real time measurements of antibiotic effects on the bacterial cell surface LPS, which is shown to correlate to their antibiotic effects. At the end point, after 18 hour incubation of bacterial cells with these three antibiotics respectively, the bacterial LPS binding signal was reduced to 23%, 27%, and 38%, respectively, for the three antibiotics, indicating that ciprofloxacin is the most effective against this *E. coli* strain. Real time measurements at the 1 hour time point showed a similar trend with a reduction of binding to 91%, 93%, and 95%, respectively. From the binding kinetics of these measurements, the relaxation time ($\tau$) was obtained, where higher $\tau$ value means slow binding interactions between the lectin and the bacterial LPS. The obtained order of $\tau$, (i.e., $\tau_{ciprofloxacin} > \tau_{ceftriaxone} > \tau_{tetracycline}$) again indicated that ciprofloxacin has more bactericidal activity than the other two antibiotics with the same concentrations. These results indicate that the reduction in the binding of LPS with the lectin Con A sensor upon exposure to various antibiotics has a direct relation with the antibiotic dosages making this label free biosensor assay promising for therapeutic management of these drugs as well as for applications in antibiotic research and development. The details of this example will now be described.

Chemicals and Materials (4-(2-Hydroxyethyl)-1-piper-azineethanesulfonic acid) (HEPES) was purchased from VWR International. Triethanolamine, ceftriaxone disodium salt hemi (heptahydrate) (third-generation cephalosporin antibiotic), ciprofloxacin (≥98.0% (HPLC)), and tetracycline (≥98.0% (NT)) were purchased from Sigma-Aldrich. Fresh dilutions of the antibiotics were prepared daily in either sterile culture medium or distilled water. Concanavalin A (Con A) was purchased from Sigma. *E. coli* W1485 (ATCC 12435) was obtained from ATCC. All other reagents and materials were analytical grade and solvents were purified by standard procedures.

Biosensor Interface Fabrication and Characterization

Before use, the bare gold electrode of QCM sensor (International Crystal Manufacturing Co. Inc.) was cleaned with Piranha solution (1:3 30% H2O2: concentrated H2SO4) for 5 minutes to remove organic adsorbate impurities from the gold surface. The gold electrode was then rinsed thoroughly with deionized water. Excess water was removed by drying with nitrogen gas. To avoid deposition of contaminants on the gold electrode surface, the cleaned QCM wafer was immediately used for the following experiments.

Electrochemical polymerization of 3-((2,5-dimethoxyphenyl)ethynyl)thiophene (abbreviated TQ) monomers can be carried out by using potentiometry, galvanometry, or cyclic voltammetry techniques. Cyclic voltammetry was employed in this Example. Cyclic voltammetry uses multiple potential cycles to form the polymer film allowing the electrochemical characteristics of the growing polymer to be monitored during the polymerization process and the film can be grown more uniformly.

Thus, polyTQ film was deposited on the gold electrode (surface area 0.22 cm2) in CH3CN with 0.1 M LiClO4 as supporting electrolyte (~5 mL) containing about 2 mM TQ by cyclic voltammetry. Before experiment, the supporting electrolyte was deoxygenized using nitrogen for 20 minutes. The potential sweep range was between 0.5 V and 1.2 V (vs Ag/AgCl wire) at a scan rate of 20 mV/s for 20 cycles. The yellow-brown film modified gold electrode, having TQ polymer as "solid-state probe", was washed with CH3CN and water. The cyclic voltammograms of polymerization were recorded with a GAMRY electrochemical workstation.

The yellow-brown film modified gold electrode, was washed with CH3CN and water before following experiments. The TQ modified gold electrode was incubated in a solution of 4 mg/mL conjugate of thiol-modified mannose, a DMannopyranoside, 2-[2-(2-mercaptoethoxy) ethoxy] ethyl (abbreviated SM), with 10 mM HEPES buffer containing a catalytic amount of triethanolamine and the potential was repeatedly scanned in the region from −0.2 V to 0.8 V at a scan rate of 20 mV/s.3. Then, 300 nM Con A was added onto the gold surface for 1 hour. After incubation, the modified electrode surface was washed with biograde water and HEPES buffer. This Con A sensor was then ready for the following experiments via electrochemical or quartz crystal microbalance (QCM) measurements.

Quartz Crystal Microbalance (QCM) Setup

The gold QCM electrode consisted of a thin AT-cut quartz crystal wafer with vapor deposited gold electrode on each side (10 MHz, non-polished with 1000 A gold, geometric area is 0.22 cm2, International Crystal Company). For all QCM test, the gold electrode was mounted on the side of a Kel-F cell chamber. Frequency monitoring was performed using a Maxtek RQCM quartz crystal microbalance research instrument. Baseline was recorded in 1 mL of 10 mM HEPES buffer containing 1 mM $Ca^{2+}$ and 1 mM $Mn^{2+}$. Each of the bacterial samples to be analyzed was then added into the detection sensor cell after stabilization of resonance frequency (shift less than 1 Hz·min-1). A small magnetic stir bar was used to increase the mass transfer through convection. The frequency changes ($\Delta F$) of the QCM were monitored using a network/spectrum/impedance analyzer (Agilent 4395A) controlled by a PC via an Intel card.

Electrochemical Measurements

Electrochemical measurements were performed on a GAMRY 4-channel electrochemical workstation. A three-electrode electrochemical cell composed of a Con A sensor as working electrode, platinum wire as counter electrode and Ag/AgCl (saturated KCl) electrode as reference electrode, was used. Square wave voltammetric measurements were performed under ambient conditions (21-23° C.). Each measurement had been repeated at least three times with independently prepared Con A sensors.

Atomic Force Microscopy (AFM) and FTIR Characterization of the Surface Modifications AC mode AFM images were obtained from a PicoPlus Atomic Force Microscope (Agilent Technologies, Calif.) by using Au coated silicon probes of resonant frequency 75 kHz and spring constant 3.5 N/m. The Au (111) substrate used for AFM measurement was prepared following the Clavilier method. Prior to each experiment, the Au surface was subjected to electrochemical polishing followed by flame annealing and cooling in nitrogen to obtain a clean, high-quality surface. For the FTIR experiment, the polymer was electrochemically deposited on an indium tin oxide (ITO)-coated glass electrode. FTIR spectra were recorded on a Varian Excalibur series 3100 FTIR spectrometer mounted with a liquid-nitrogen-cooled MCT detector.

Characterization of the Con A Sensor

Figure 21:
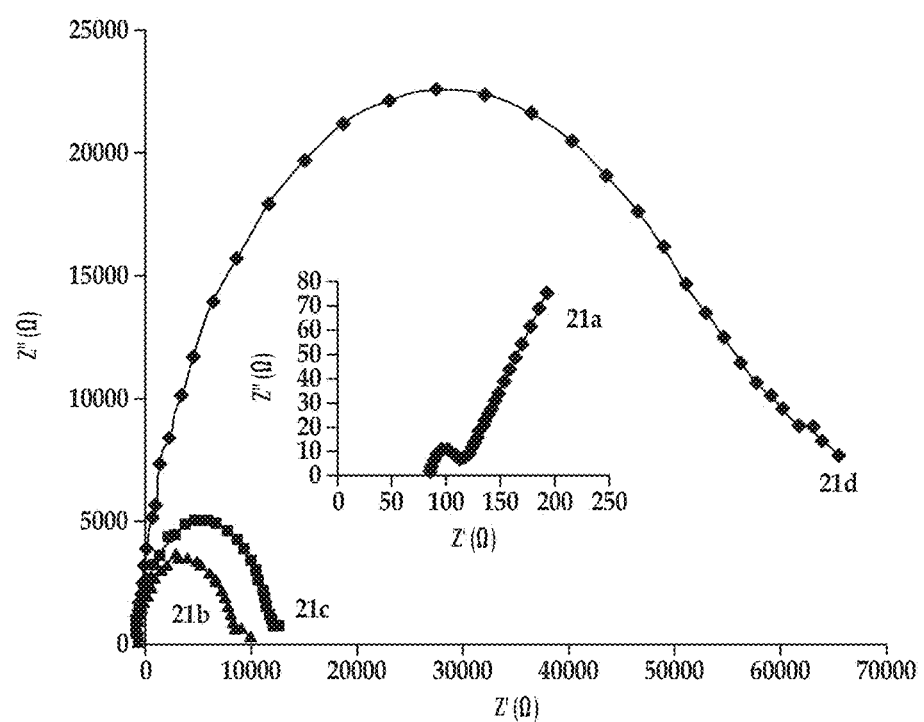
FIG. 21 depicts Nyquist plots of impedance spectra obtained in 10 mM PBS (pH 7.40) containing 10 mM $K_3Fe(CN)_6$-10 mM $K_4Fe(CN)_6$-0.1M $NaClO_4$ at (21a) bare gold electrode; (21b) TQ modified gold electrode; (21c) SM/TQ modified gold electrode; (21d) Con A/SM/TQ modified gold electrode (frequency range is 0.1 Hz-100 kHz, bias potential equals to open circuit potential, AC amplitude is 10 mV)

FIG. 21 shows the electrochemical impedance spectra (EIS) at each step of the fabrication of the Con A sensor. The EIS of the bare gold electrode (line 21a) exhibits a very small semicircle domain, suggesting a very low electron-transfer resistance ($R_{et}$, 25Ω). After the TQ was attached to the bare gold electrode using electrochemical polymerization (line 21b), the Ret increased from 25Ω to 9084Ω, attributed to the fact that hydroquinone/quinone group of TQ confined to the gold surface blocks the electrode surface. As the SM designed was coupled to quinone group of the TQ (line 21c), the $R_{et}$ increased from 9084Ω to 12576Ω. The monosaccharide unit could block the redox process of $Fe(CN)_6^{2-}/Fe(CN)_6^{3-}$ in solution to the electrode surface, leading to the increased electron-transfer resistance of $Fe(CN)_6^{2-}/Fe(CN)_6^{3-}$. After Con A was captured onto the surface of SM/TQ modified gold slide, the $R_{et}$ increased from 12576Ω to 57591Ω (line 21d). This is probably attributed to the fact that an insulating layer on the surface of SM/TQ modified gold slide is generated and the transfer of redox couple $Fe(CN)_6^{2-}/Fe(CN)_6^{3-}$ to the surface of gold slide is prohibited. The result indicates that the Con A sensor was fabricated successfully and can be used for further experiments.

Figure 22A:
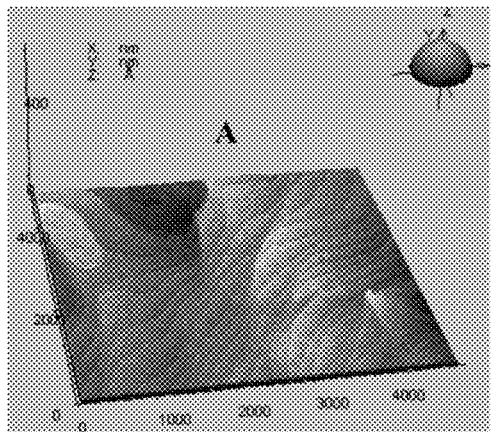
FIGS. 22A through 22D are atomic force microscopy (AFM) topographic images of (FIG. 22A) bare Au(111) surface, (FIG. 22B) TQ modified Au(111) surface, (FIG. 22C) SM/TQ modified Au(111) surface, and (FIG. 22D) ConA/SM/TQ modified Au(111) surface.
Figure 22B:
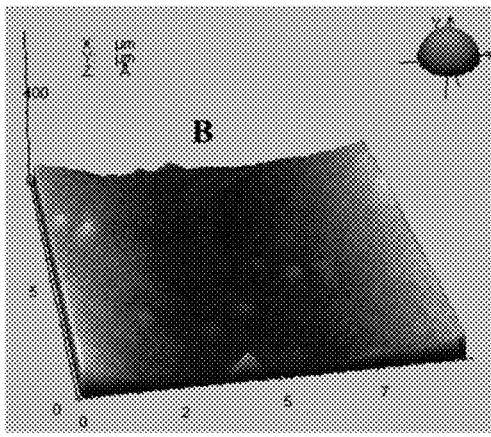
Figure 22C:
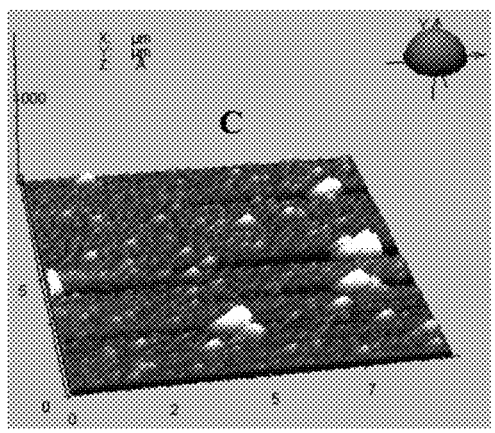
Figure 22D:
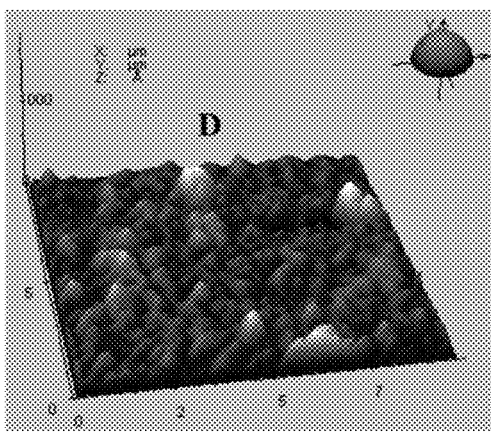

The SM/TQ modified gold electrode was characterized by AFM and FTIR. FIG. 22A shows AFM image of freshly prepared Au(111) surface. In this figure, the clear observation of Au steps indicated a clean and high quality Au(111) surface. FIG. 22B shows the Au(111) surface after the medication of TQ molecules. The formation of TQ monolayer hinders the observation of Au(111) steps in AFM measurement. After the addition of SM molecules, the topographic AFM image indicated a very rough surface, as shown in FIG. 22C. The addition of Con A led to agglomerate morphology (FIG. 22D), which is similar to the reported surface structure of Con A.

Figure 23:
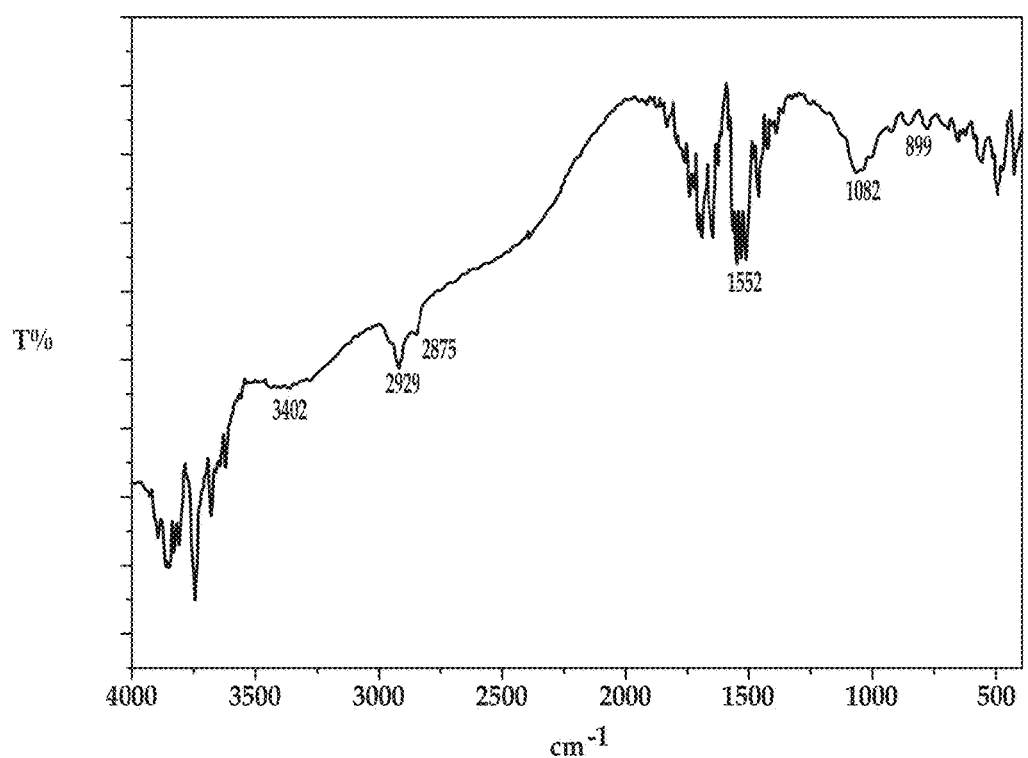
FIG. 23 is the Fourier transform infrared spectroscopy (FTIR) spectra of the SM/TQ modified indium tin oxide (ITO)

FTIR was used to further confirm the SM/TQ modified interface. For the FTIR experiment, the gold electrode was replaced by indium tin oxide (ITO). The identical electrochemical polymerization condition of TQ at gold electrode was used. The conditions may not have been optimal for an ITO electrode. Therefore, the surface density of TQ monolayer at ITO is smaller than that at gold electrode. However, the data still provides the information of the chemical analysis of the biointerface. FIG. 23 shows the FTIR spectra of SM/TQ films coated onto ITO electrodes. The Varian Excalibur series 3100 FTIR spectrometer used to obtain the FTIR spectra gives the data of transmittance (T%, Y-axis), which is normalized with the background. Thus, the transmittance values are not absolute values, and as such, the Y axis has no value. There was no distinct spectrum of the ITO electrode without TQ monolayer. In the spectrum of SM/TQ (FIG. 23), the bands between 1500 $cm^{-1}$ and 1300 $cm^{-1}$ originated from the stretching modes of C=C and C—C in the thiophene ring. The bands at 1066 $cm^{-1}$ and 1045 $cm^{-1}$ are assigned to stretching of the C—O—C bonds of SM. Vibrations from the C—S bond in the thiophene ring of TQ are shown at 893 $cm^{-1}$ and 871 $cm^{-1}$. The peaks at 1692 $cm^{-1}$, 1644 $cm^{-1}$ and 1534 $cm^{-1}$ are assigned to the stretching and bending modes of benzene ring in the structure of TQ. A strong absorption peak at 1732 $cm^{-1}$ is characteristic of the stretching vibration of the carbonyl group of TQ. Both the results of AFM and FTIR showed that the SM/TQ interface was successfully fabricated and can be used to quantify of antibiotic effects on bacterial LPS.

E. coli W1485 Culture and Sensitivity Test

The W1485 strain of E. coli was used. The culture of E. coli W1485 was grown in Levinthal broth (LB) at 37° C. for 18 hours in a shaking incubator. During the growth of a bacterial culture, a succession of phases, characterized by variations of the growth rates, are conveniently distinguished and be modeled with four different phases: lag phase, log phase (i.e., exponential phase), stationary phase, and death phase. In this Example, the cultured bacteria sample (either in log phase or stationary phase) was directly diluted with HEPES buffer to the desired concentrations and frozen for further use without any washing steps so that the E. coli was basically in a nongrowing phase.

The antimicrobial susceptibilities of various antibiotic drugs were determined by the described Con A biosensor. Three different antibiotics, cipfloxacin, ceftriaxone, and tetracycline with different mechanisms of actions, were used to study their different abilities to kill or inhibit the bacterial growth. Both end point and real time measurements were performed.

In the end point measurement, four samples containing $2×10^5$ cells/mL of E. coli obtained from log phase in fresh LB culture were prepared. Ceftriaxone (final concentration is 0.1 mg/L), ciprofloxacin (final concentration is 0.1 mg/L), or tetracycline (final concentration is 10 mg/L) was added into each sample, respectively. The four samples were incubated for 18 hours, 37° C., 280 rpm on an orbital environmental shaker. Finally, 1 μL of the E. coli culture from the each prepared sample was introduced to the Con A biosensor in 1 mL of 10 mM HEPES buffer (pH 7.4) for QCM and electrochemical biosensor measurements, respectively. The sample without addition of any antibiotic was used as control.

For the real time measurements, Con A sensor was mounted in a biosensor cell containing 1 mL of 10 mM HEPES buffer (pH 7.4). Real time QCM measurements were obtained for each experimental step. First, 1 μL of $5×10^8$ cells/mL E. coli obtained from the stationary phase was added into the biosensor cell. When frequency reached a constant value, it was washed with 1 mL of 10 mM HEPES buffer to remove the unbound E. coli. Second, ciprofloxacin, ceftriaxone, or tetracycline with the final concentration of 30 mg/L was added to the Con A sensor cell, respectively. The frequency changes vs time and the damping resistance vs time were recorded by QCM. By obtaining the damping resistance through fitting the Butterworth-van-Dyke equivalent circuit, it can be determined whether the surface layer shows viscoelastic characteristics. After the ciprofloxacin, ceftriaxone, or tetracycline was incubated with E. coli for 3 hours, the electrochemical signal changes were recorded by the same biosensor but measuring the electrochemical signal instead.

Experiments were also performed to study the concentration of the antibiotics and the length of the incubation time of antibiotics for their ability to kill or inhibit the growth of the bacteria. Different concentrations of each antibiotic were added to $5×10^8$ cells/mL E. coli respectively, and then incubated at 37° C. and 280 rpm on the shaker. After 3 hours of incubation, 1 μL of antibiotic treated E. coli culture was added to the Con A sensor cell containing 1 mL of 10 mM HEPES buffer (pH 7.4) for QCM measurements, respectively. To study the effects of length of the incubation time, ceftriaxone, ciprofloxacin, or tetracycline at concentration of 10 mg/L was added into $5×10^8$ cells/mL E. coli. 1 μL of each antibiotic treated E. coli was taken at different incubation times (i.e., 0, 1, 2, 3 hours) and was added into the Con A senor cell containing 1 mL of 10 mM HEPES buffer (pH 7.4) for QCM measurements.

Results and Discussion

Biosensors for Antimicrobial Susceptibility Tests

FIG. 20 schematically describes the modes of actions of three different antibiotics (i.e., ciprofloxacin, ceftriaxone, and tetracycline) used in this Example. The interaction of antibiotics with the bacteria cause the alterations of the outer membrane of bacterial cell wall, and subsequently the properties of LPS, located in the outer layer of the outer membrane, with the magnitude of that effect depending upon the antibiotic used. For instance, ciprofloxacin, a quinolone derivative with a broad antibacterial spectrum, destabilizes the LPS structures in the bacterial outer membrane. Ceftriaxone, one kind of lactamase-stable cephalosporins, inhibits the bacterial cell wall synthesis by acting as suicide substrates. This results in a rapid fragmentation of the bacteria and ultimate release of LPS. Tetracyclines, on the other hand, are broad-spectrum protein synthesis inhibitors. Tetracyclines also caused the LPS release; however, it is unclear what mechanism is responsible for their effect on LPS of bacteria. Regardless of the cause of its effect on LPS, tetracycline consequently affects the bacterial binding with the sensor due to lesser binding sites available.

The previously described characterization of the biosensor illustrates that the system has multiple orthogonalities: (1) the innovative biointerface with built-in solid state redox probe allows label free and reagentless transduction of both electrochemical and QCM mechanisms, and (2) the signals generated by these mechanisms are by themselves orthogonal; the electrochemical measurements is a signal OFF approach (i.e., an increase of analyte concentration results in a decrease of the signal) whereas the QCM is a signal ON approach (i.e., an increase of analyte concentration results in an increase of the signal) for this biointerface. All these functions of the biointerface positively interact to provide enhanced sensitivity, broader dynamic range of detection, and greater reliability via cross-validation.

In the present Example, the binding of Con A with LPS was used that leads to an increase in the mass loading at the interface which brings about a shift in the frequency of the QCM sensor. With increasing bacterial binding, the shift of the frequency should be increasing and vice versa, so the QCM in this sensor is a signal ON approach. Contrarily, with a similar increase in binding, the electron transport of the quinone-fused polythiophene at the interface should be hindered, thereby lowering the electrochemical signal and thus, it is a signal OFF approach. This Example demonstrates the feasibility of using this lectin sensor to quantify the difference in the modes of actions of different types of antibiotics on Gram-negative bacteria by relating their effect on the bacterial cell surface morphology and LPS properties upon the antibiotic exposures.

Figure 24A:
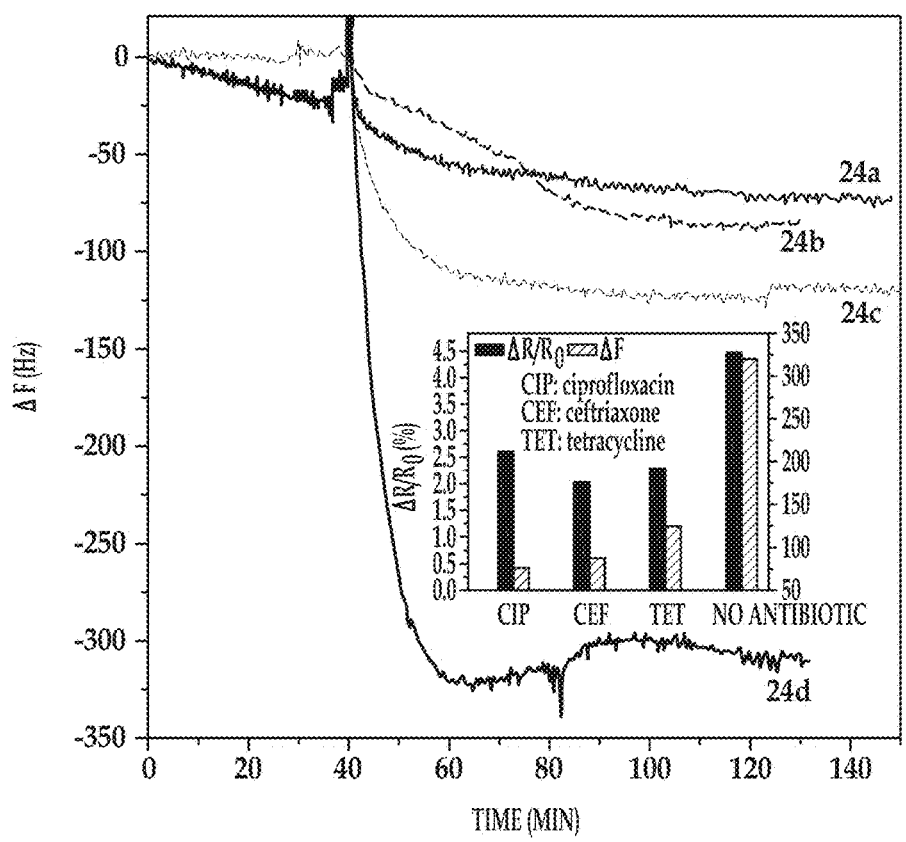
FIGS. 24A and 24B are graphs respectively showing (FIG. 24A) frequency change vs. time curve and (FIG. 24B) square wave voltammetry (SWV) responses when Con A sensor was exposed to E. coli pretreated by 0.1 mg/L ciprofloxacin (24a), 0.1 mg/L ceftriaxone (24b), and 10 mg/L tetracycline (24c), and blank samples without addition of any antibiotics (24d) in log phase, and then incubated for 18 hours, 37° C., 280 rpm on an orbital environmental shaker, in HEPES buffer (pH 7.4) with 1 mM $Mn^{2+}$ and 1 mM $Ca^{2+}$ (the insets indicate the sensor responses in comparison to control measurements both for the QCM and electrochemical approaches)

It was hypothesized that subtle changes of LPS integrity and function will lead to diminished bacterial binding with the lectin sensor that can be measured real time. Consequently, a fast antimicrobial susceptibility test can be established to determine antibiotic efficacy in vitro in an efficient manner. To validate that the described biosensor can be used for an antimicrobial susceptibility test for the chosen antibiotics, $2 \times 10^5$ cells/mL of $E.$ $coli$ samples were prepared in fresh LB culture and then incubated with antibiotics ceftriaxone (final concentration=0.1 mg/L), ciprofloxacin (finial concentration=0.1 mg/L) or tetracycline (final concentration=10 mg/L) for 18 hours, at 37° C. and 280 rpm in a shaking incubator. The concentrations used were based on the literature and current clinically used dosages. The sample without any antibiotic was used as a control. As mentioned above, $E.$ $coli$ W1485 was used as the model Gram-negative bacterial analyte. $E.$ $coli$ W1485 is a "semi-rough" bacterial strain in which the intact LPS core is capped by a single O-antigen subunit consisting of glucose, N-acetylglucosamine, galactose, and rhamnose in the ratio 1.8:1.0:0.7:0.6, which has been confirmed by the sodium dodecyl sulfate polyacrylamide gel electrophoresis (SDS-PAGE) method. Con A binds specifically at α-D-mannosyl and α-D-glucosyl residues (two hexoses differing only by the alcohol on carbon 2) in the terminal position of ramified structures from β-glycans (reach in α-mannose, or hybrid and biantennary glycanes complexes). Therefore, the multivalent binding of Con A to the $E.$ $coli$ W1485 surface O-antigen glucose receptor facilitates the strong adhesion of $E.$ $coli$ W1485 to the mannose immobilized on the QCM surface. Afterward, these samples were analyzed for their QCM and electrochemical sensor responses, which are shown in FIGS. 24A and 24B.

As shown in FIG. 4A, the blank sample with no antibiotics provided the highest QCM signal; and highest damping resistance (R) changes as the bacterial cell surface LPS in this sample are at their fully functional state, which resulted in highest binding to the sensor interface (curve 24$d$). Here the QCM frequency shift is because of the mass loading on the QCM surface due to bacterial adhesion and the change of damping resistance is a result of increasing softness of the interface which causes the damping of the oscillation wave. The detailed explanation of these phenomena can be found elsewhere; however, the present inventors have already shown that in case of Con A-LPS binding, the frequency-resistance ratio is high enough to consider this binding as rigid, and the mass loading as the dominant effect whereas the softness of the interface can be considered negligible. Once the samples having various antibiotics (ciprofloxacin (24$a$), ceftriaxone (24$b$), and tetracycline (24$c$)) were introduced, a much smaller shift in frequency was observed as well as smaller damping resistance change, which quantitatively depended upon the antibiotic used. By normalizing these frequency shifts to that obtained from the control (inset in FIG. 24A), it was found that the bacterial binding was reduced to 38%, 27%, and 23% for the given concentrations of tetracycline, ceftriaxone, and ciprofloxacin, respectively. These results suggest that the antibiotics inhibited the growth of $E.$ $coli$ in log phase and affected the LPS integrity and function at bacterial cell surface so that a smaller number of $E.$ $coli$ bound to the Con A sensor, compared to the control sample without antibiotics.

Figure 24B:
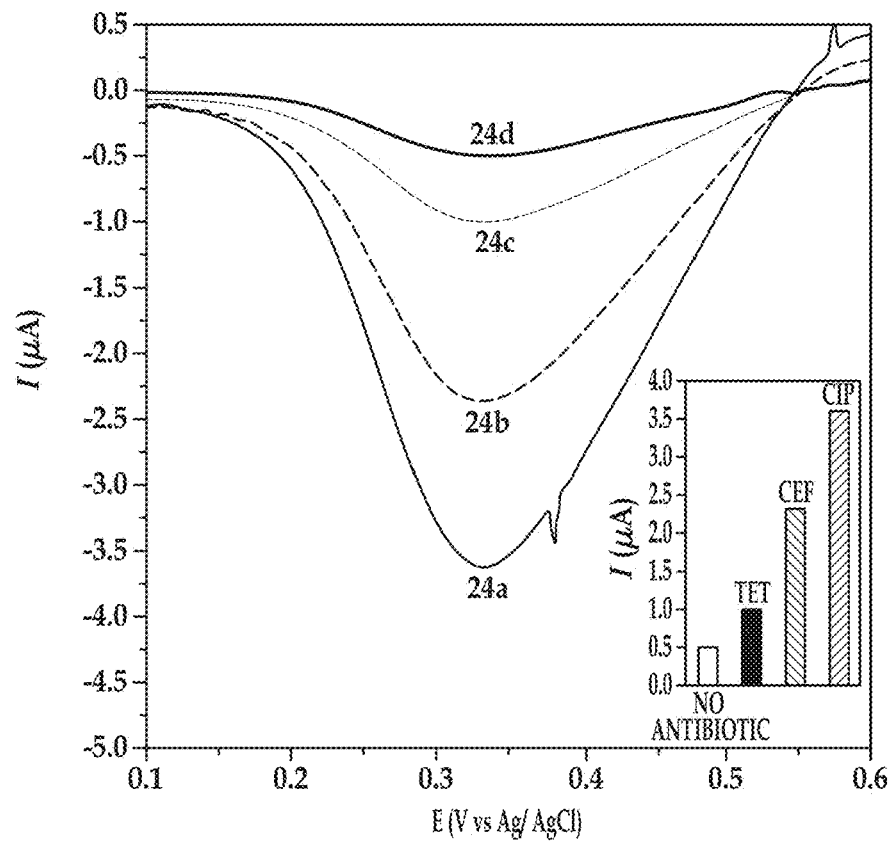

To further confirm the results by an internal validation method, the quinone-fused polythiophene solid probe allows simultaneously analyzing the same binding events via square wave voltammetry (SWV) and the results are shown in FIG. 24B. Here, the Con A sensor displayed increasing SWV signals (curves 24$a$, 24$b$, and 24$c$) when antibiotics were added, compared to control experiment (curve 24$d$). The pattern of the responses was also related to what was obtained from QCM. Normalization of the SWV signal showed a 7.2, 4.8, and 2 folds increase of the signal as compared to control experiment with addition of 0.1 mg/L of ciprofloxacin, 0.1 mg/L of ceftriaxone or 10 mg/L of tetracycline, respectively (Inset, FIG. 24B). From these results, it was clearly indicated that all three antibiotics are able to alter the LPS properties and could inhibit the $E.$ $coli$ growth. However, they differ in their strengths for this inhibition, thus having different consequences in terms of binding. Ciprofloxacin is slightly more active than ceftriaxone against $E.$ $coli$ at the same concentration, and both ceftriaxone and ciprofloxacin are superior to tetracycline against $E.$ $coli$. The electrochemical approach displayed a more distinctive difference of antibiotics susceptibilities than that shown in QCM; however, electrochemical measurement is an end point calibration. QCM, on the other hand, can be used to monitor the process real time and thus can determine the binding kinetics between Con A on the sensor surface and $E.$ $coli$ pretreated by various antibiotics. Therefore, this combined quartz crystal microbalance and electrochemical readouts (EQCM) approach has multiple advantages in addition to cross-validating the measurement results.

Real Time Analysis of Bactericidal Activities of Antibiotics

Different types of antibiotics have differing abilities to alter the LPS properties and subsequent reduction in their binding. This can be used as an indicator for the antibiotic effects for killing the bacteria or inhibiting their growth. The biosensor ability to quantitatively measure these parameters real time was tested. For that purpose, the Con A sensor was exposed to 1 µL of 5×10$^8$ cells/mL E. coli to capture the bacteria via Con A-LPS binding. The unbound E. coli was removed by washing with 1 mL of 10 mM HEPES buffer. Antibiotic samples were then added into the sensor cell with the final concentration of 30 mg/L and the frequency changes were measured in real time (FIG. 25A, ciprofloxacin (25a), ceftriaxone (25b), or tetracycline (25c)). After an incubation of 3 hours, the electrochemical signals were also recorded (FIG. 25B, ciprofloxacin (25a), ceftriaxone (25b), or tetracycline (25c)). In the three separate measurements shown in FIG. 25A, it can be clearly seen that the initial parts of the curves which are related to E. coli immobilization are almost coinciding to each other. This real time QCM measurement also allows us to observe the reproducibility of the sensor performance. In the last parts of the curves, when different antibiotics are added, their variable effects in killing the bacteria and reducing their binding caused a variable shift of the frequency. This shift was opposite in direction to what was obtained by bacterial addition which is indicative of reduced binding. These responses (shown in the inset) provided the quantitative details of this effect. During the 2 hour period after the antibiotic addition, 350 to 320 Hz (0.91-fold), 350 to 325 Hz (0.93-fold), and 370 to 350 Hz (0.95-fold) decreases in frequency for ciprofloxacin, ceftriaxone, and tetracycline, respectively, were observed. Due to real time nature of this experiment, the frequency and damping resistance change were much smaller than that of FIGS. 24A and 24B. This confirms that the antibiotic drug effect on LPS is a slow process but the high sensitivity sensor disclosed herein allows such subtle changes to be measured. Moreover, the results of the QCM and Electrochemical measurements are validating each other again. The mass effect is diminishing as compared to the control measurement due to the lesser binding as a result of real time antibiotic effect, whereas the electrochemical signal is increasing for the same reason.

Table 4 describes the magnitudes of both the frequency shifts as well as the resistance changes for all the experiments.

TABLE 4

Figure 25A:
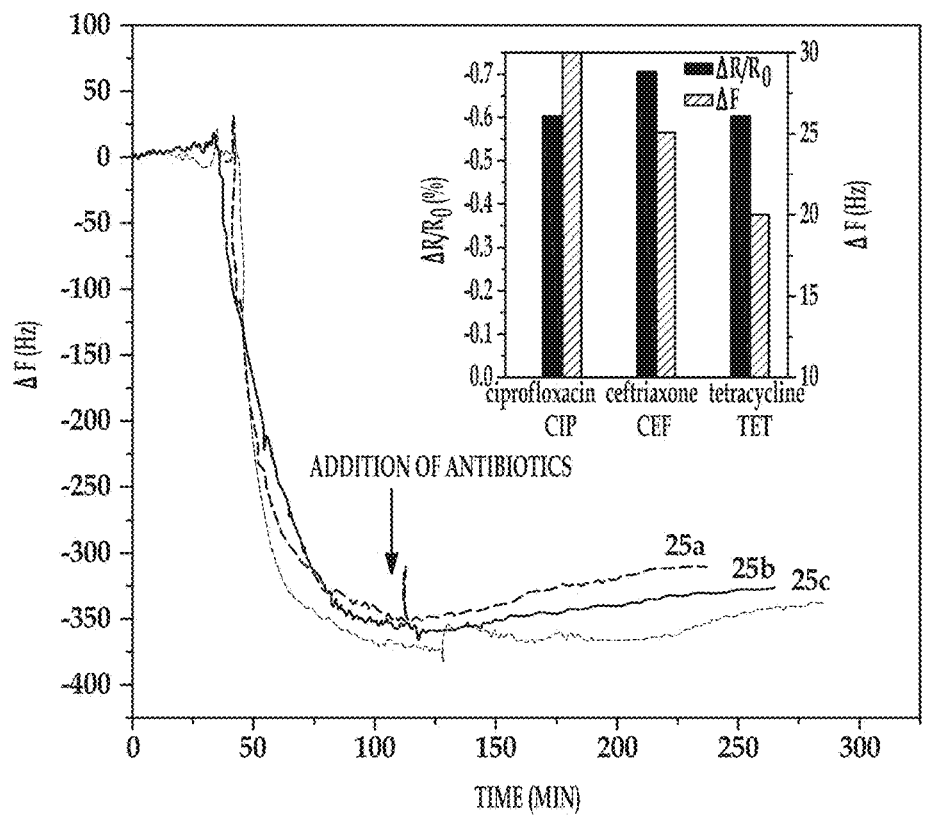
FIGS. 25A and 25B are graphs respectively showing (FIG. 25A) frequency change vs. time curve when Con A mediated sensor was exposed to E. coli W1485 obtained from stationary phase, and then 30 mg/L ciprofloxacin (25a), ceftriaxone (25b), or tetracycline (25c) was added into the QCM cell after E. coli were attached on the Con A sensor, and (FIG. 25B) the corresponding square wave voltammetry (SWV) responses with 30 mg/L ciprofloxacin (25a), ceftriaxone (25b), and tetracycline (25c), and without addition of any antibiotics (25d) in HEPES buffer (pH 7.4) with 1 mM $Mn^{2+}$ and 1 mM $Ca^{2+}$ (the insets show the sensor responses for both the electrochemical and SWV approaches)
Figure 25B:
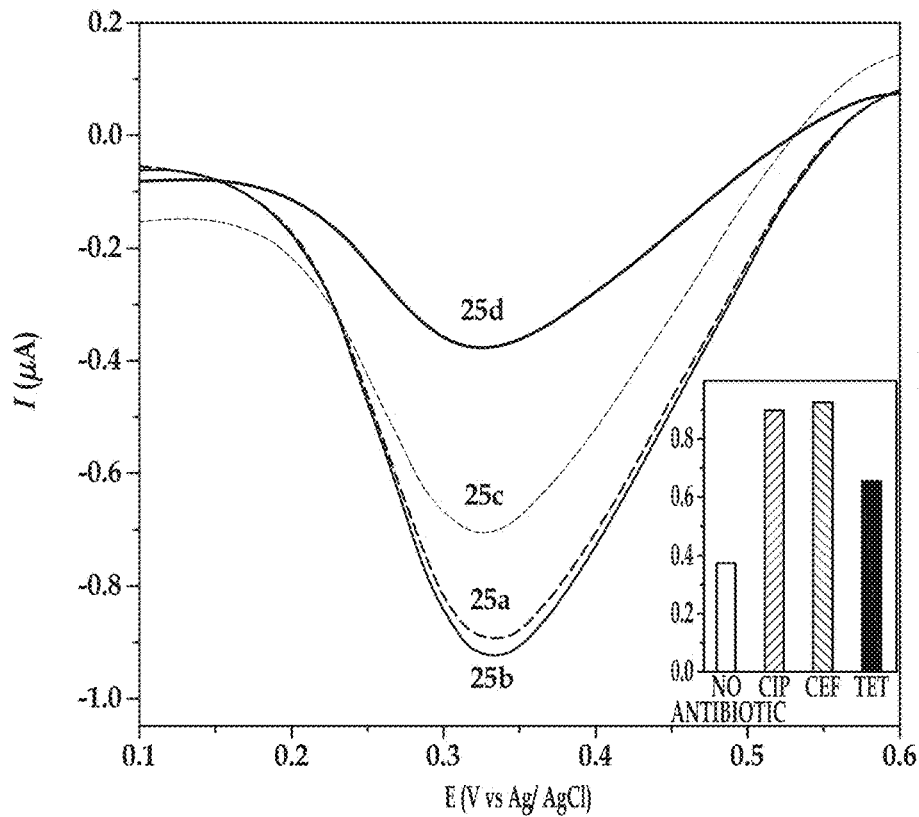
Figure 26A:
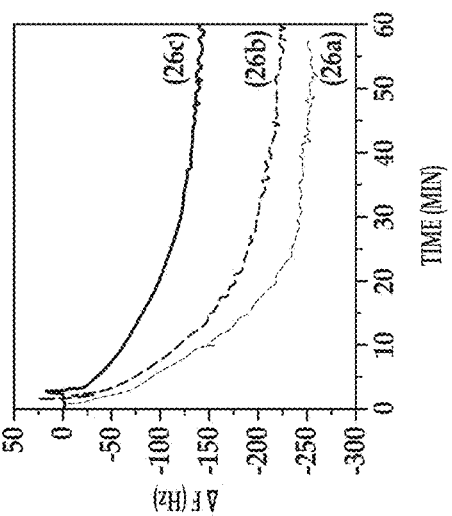
FIGS. 26A through 26C are graphs depicting the frequency change vs time curve when Con A sensors were exposed to E. coli W1485 obtained from stationary phase and then pretreated with (FIG. 26A) ceftriaxone.
Figures 26B, 26C:
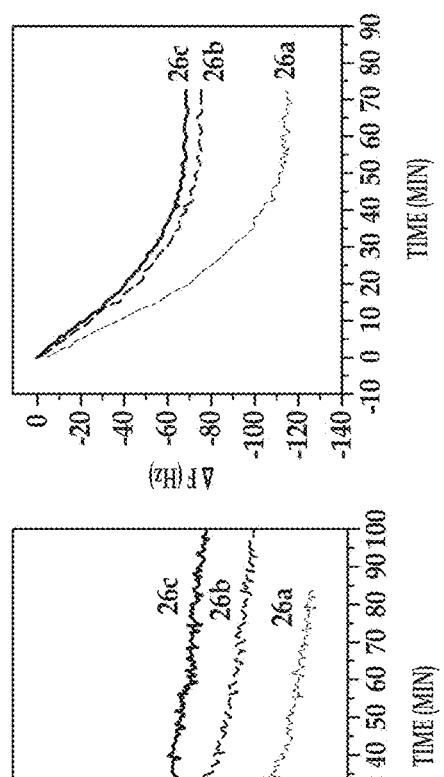
Figure 26D:
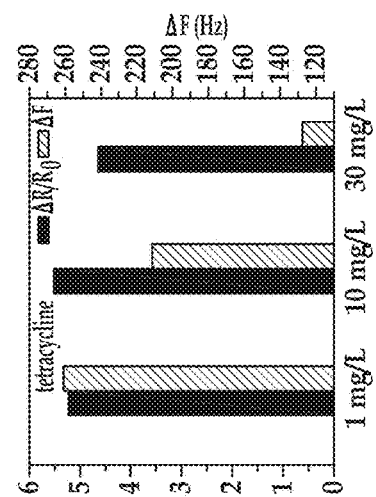
FIGS. 26D through 26F are graphs depicting the normalized QCM frequency shifts and damping resistance changes obtained from the variation of concentration of different antibiotics.
Figures 26E, 26F:
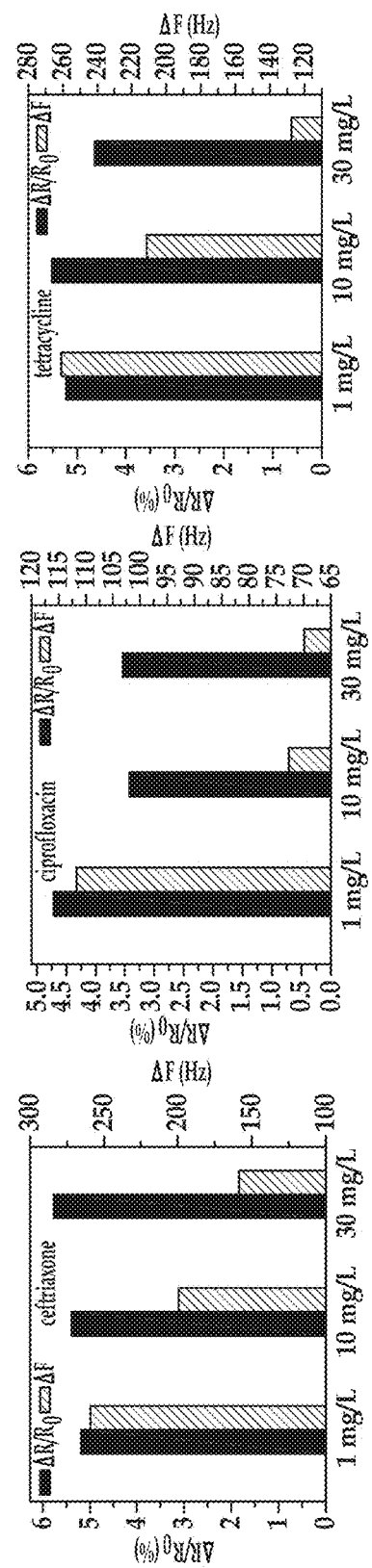
Figure 27B:
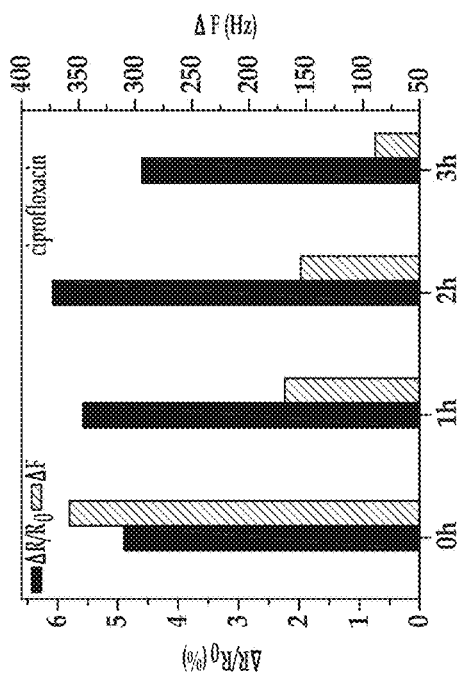
FIGS. 27A through 27D are graphs depicting (FIG. 27A) the effect of time on (27a) 10 mg/L ciprofloxacin, (27b) 10 mg/L ceftriaxone and (27c) 10 mg/L tetracycline against E. coli obtained from stationary phase determined by the SM/TQ-QCM sensor in 1 mL of stirred HEPES with 1 mM $Mn^{2+}$ and 1 mM $Ca^{2+}$, and (FIGS. 27B-27D) the normalized QCM frequency shifts and damping resistance changes obtained from the variation of different antibiotics with different incubation time.
Figure 27D:
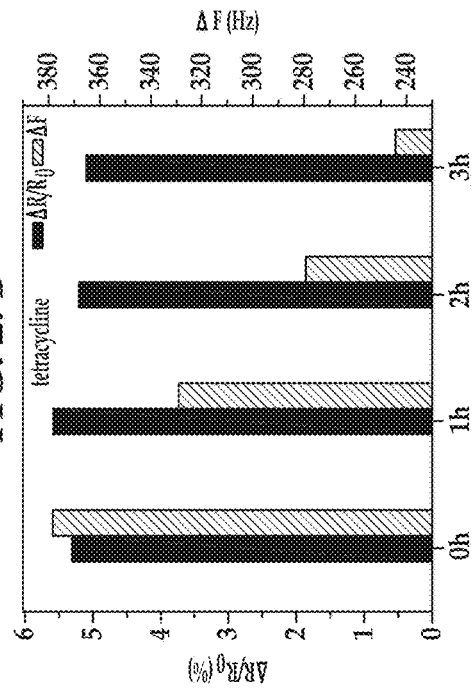
Figure 27A:
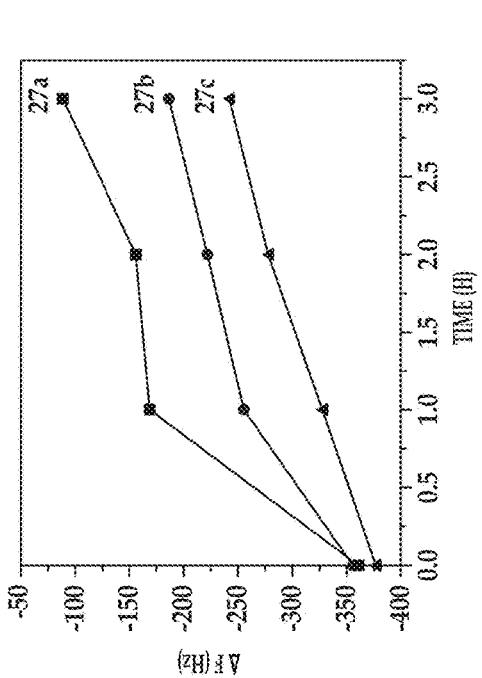
Figure 27C:
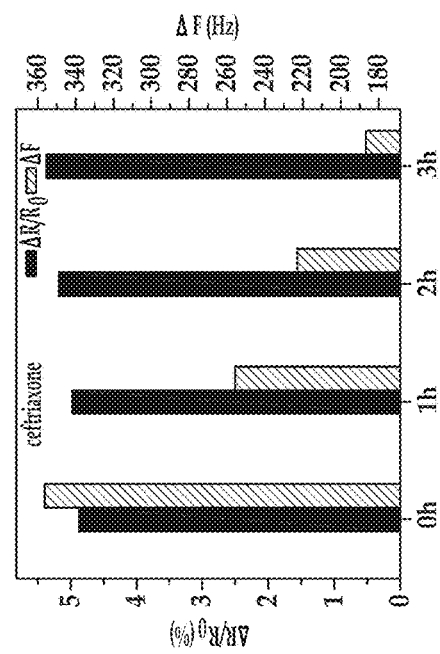

| | | | $R_0$ (Ω) | ΔR (Ω) | $ΔR/R_0$ (%) | ΔF (Hz) |
|---|---|---|---|---|---|---|
| FIGS. 24A | 24a | | 308 | 8 | 2.6 | 75 |
| | 24b | | 307 | 6 | 2.0 | 87 |
| | 24c | | 308 | 7.2 | 2.3 | 125 |
| | 24d | | 308 | 14 | 4.5 | 320 |
| FIG. 25A | 25a | | 323 | −2.0 | −0.6 | −30 |
| | 25b | | 325 | −2.2 | −0.7 | −25 |
| | 25c | | 323 | −2.0 | −0.6 | −20 |
| FIG. 26 | FIGS. 26A and 26D | (26a) | 305 | 16 | 5.2 | 260 |
| | | (26b) | 304 | 16.5 | 5.4 | 200 |
| | | (26c) | 308 | 18 | 5.8 | 160 |
| | FIGS. 26B and 26E | (26a) | 307 | 14.5 | 4.7 | 112 |
| | | (26b) | 305 | 10.5 | 3.4 | 73 |
| | | (26c) | 307 | 10.6 | 3.5 | 70 |
| | FIGS. 26C and 26F | (26a) | 306 | 16.3 | 5.3 | 262 |
| | | (26b) | 305 | 17.2 | 5.6 | 212 |
| | | (26c) | 305 | 14.5 | 4.7 | 128 |
| FIG. 27 | FIGS. 27A(a) | 0 h | 305 | 15 | 4.9 | 360 |
| | | 1 h | 304 | 17 | 5.6 | 169 |
| | and 27B | 2 h | 305 | 18.6 | 6.1 | 156 |
| | | 3 h | 307 | 14 | 4.6 | 89 |
| | FIGS. 27A(b) and 27C | 0 h | 306 | 15 | 4.9 | 356 |
| | | 1 h | 308 | 15.5 | 5.0 | 256 |
| | | 2 h | 307 | 16.1 | 5.2 | 223 |
| | | 3 h | 305 | 16.6 | 5.4 | 187 |
| | FIGS. 27A(c) and 27D | 0 h | 304 | 16 | 5.3 | 378 |
| | | 1 h | 305 | 17 | 5.6 | 329 |
| | | 2 h | 307 | 16 | 5.2 | 279 |
| | | 3 h | 304 | 15.6 | 5.1 | 244 |

From these results, it can be clearly noted that changes in frequency and the damping resistance are always in the same direction, thus these changes are correlated to each other. For instance, the frequency shifts for the data in FIG. 25A are negative, and so are the resistance changes in these experiments. However, among three antibiotics, ceftriaxone shows the highest changes in resistance in both the end point susceptibility testing as well as the real time study in this experiment. This can be related to its mechanism of action shown in FIG. 20. Ceftriaxone causes the bacterial cell to finally lyse, thus generating more fluid contents than the others, which contribute more toward the resistance changes. Thus, the damping resistance data in these experiments can also be hinting toward final fate of the bacterial cells. Similarly, as a susceptibility experiment, the SWV sensor signal for the E. coli/Con A-QCM modified gold electrode without addition of any antibiotic displayed the lowest value of 0.37 µA. After incubation with ciprofloxacin, ceftriaxone, or tetracycline with the same concentration of 30 mg/L, the modified gold electrode displayed the signal of 0.89 µA (2.41-fold), 0.92 µA (2.50-fold), and 0.65 µA (1.76-fold), respectively. These results indicate that LPS may become destabilized in the presence of antibiotics and ultimately released from the E. coli, so that the E. coli becomes unbound from the Con A sensor. The result also demonstrates that tetracycline has the least bactericidal activity against E. coli compared with ciprofloxacin and ceftriaxone of the same concentrations, whereas ciprofloxacin and ceftriaxone display almost similar bactericidal effects on E. coli. Once these effects can be determined in real time, one can quantitatively figure out the most effective drug, its time of response, and even its effective concentration to be for the best therapeutic management.

Effects of Concentration and the Length of Incubation Time on Bactericidal Activities of Antibiotics.

Because antibiotics from different classes have different mechanisms of action and antibiotic effects on bacterial morphology and viability are concentration and time dependent, it was hypothesized that the ability of antibiotics to kill the bacteria or inhibit its growth may be class and concentration dependent, which will affect the interaction between the LPS and Con A sensor. To further study the effects of concentration and length of incubation time on the bactericidal activities of antibiotics, different concentration of antibiotics were added into the broth containing E. coli and incubated for different lengths of times. FIGS. 26A through 26C shows frequency as a function of time of the Con A sensor interacted with E. coli pretreated by ceftriaxone (FIG. 26A), ciprofloxacin (FIG. 26B), and tetracycline (FIG. 26C) with different concentrations, respectively. This data also shows the similar trends as those originally obtained from the susceptibility tests, i.e., the ΔF decreased with increasing the concentration of the antibiotics. FIGS. 26D through 26F show the histogram of ΔF or ΔR changes vs antibiotics with different concentrations that are again correlated to each other with ceftriaxone showing consistent increase in resistance with increasing its concentration. This is probably due to more and more cell lysis, thereby intensifying the fluidic environment. For the tetracycline, the ΔF of QCM decreased to 260, 200 and 160 with changing concentration from 1 mg/L to 10 mg/L and 30 mg/L; for the ceftriaxone, the ΔF of QCM decreased to 112, 73 and 70 with the same variations in concentration; and for the ciprofloxacin, these numbers were 262, 212 and 128. Moreover, this data can be used to find out the dosage information for different antibiotics. For instance, ciprofloxacin at a concentration of 1 mg/L shows a frequency of 112 Hz, which quickly reaches 73 and 70 Hz at concentrations of 10 and 30 mg/L, respectively. Thus, there is no big change in the step from 10 to 30 mg/L. This means that the concentration of 10 mg/L is its most effective concentration to act against this bacterial strain. On the other hand, both ceftriaxone and tetracycline show consistent changes in frequency while changing the concentration which implies that even the dosages at the 30 mg/L level can be administered as well. The results of FIGS. 26A-26F also indicate that the concentration has distinctive effect on the bactericidal activity of the three kinds of antibiotics against *E. coli*, and ciprofloxacin is particularly effective against *E. coli* when compared with the other two antibiotics with the same concentrations.

To further compare the effect of concentrations on the bactericidal activities of the antibiotics, the binding kinetics between Con A sensor and *E. coli* were studied. The binding between Con A sensor and *E. coli* can be described by eq 2.

[Con A$_{attached\ to\ gold}$]+[*E. coli*]→[*E. coli*/Con A$_{attached\ to\ gold}$]  (2)

The amount of the complex *E. coli*/Con A formed at time t after the injection is given by eqs 3 and 34, where ΔMmax is the maximum binding amount of *E. coli*/Con A, ΔM is the measured binding amount, and t is the time after injection. τ is the relaxation time associated with *E. coli* binding, which is calculated from curve fittings of the ΔF during the binding process. A higher τ value means a longer binding time is required between the Con A and *E. coli*.

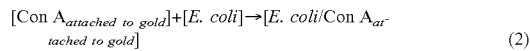

$$\left[\frac{E.coli}{Con\ A_{attached\ to\ gold}}\right]_t = \left[\frac{E.coli}{Con\ A_{attached\ to\ gold}}\right]_\infty \left(1 - e^{-\left(\frac{1}{\tau}\right)t}\right) \quad (3)$$

$$M_t = \Delta M_\infty \left(1 - e^{-\left(\frac{1}{\tau}\right)t}\right) \quad (4)$$

Table 5 summarizes the effects of concentration of antibiotics on the relaxation time τ. From Table 5, it is observed that τ increased with increasing the concentration of antibiotics while at the same concentration, τ ciprofloxacin>τ ceftriaxone τ tetracycline, which indicated that the rate of binding between Con A and *E. coli* pretreated with ciprofloxacin is smaller than that between Con A and *E. coli* pretreated with ceftriaxone and tetracycline. The result further confirmed that ciprofloxacin has more bactericidal activity than the other two antibiotics with the same concentrations.

TABLE 5

Effects of Concentration of Antibiotics on the relaxation time τ

| Concentration (mg/L) | Antibiotic | | |
|---|---|---|---|
| | ceftriaxone τ (min) | Ciprofloxacin τ (min) | tetracycline τ (min) |
| 1 | 15.5 | 21 | 11.2 |
| 10 | 18.4 | 23.5 | 13.9 |
| 30 | 22.5 | 23.6 | 19.8 |

The effect of incubation time on the bactericidal activities was studied further and the results are presented in FIGS. 27A through 27D. From the curve 27a, it can be seen that the ΔF decreased from 360 Hz to 169 Hz with extending the incubation time of ciprofloxacin to 1 hour. Within the next one hour (from 1 hour to 2 hours), the ΔF slightly decreased from 169 Hz to 156 Hz. Then from 2 hours to 3 hours, the ΔF sharply decreased again from 156 Hz to 89 Hz. Curve 27b showed the effect of incubation time of ceftriaxone against *E. coli*. In the first hour, the ΔF sharply decreased from 356 Hz to 256 Hz. And then from 1 hour to 3 hours, the ΔF gently decreased from 256 Hz to 187 Hz. Different from curves 27a and 27b, curve 27c showed the ΔF gently decreased from 378 Hz to 244 Hz with incubation time of tetracycline throughout the span of 3 hours. At the same incubation time, the ΔF shift induced by ciprofloxacin is smaller than that induced by ceftriaxone or tetracycline, but the damping resistance changes are very minimal for all three antibiotics. The results indicate that the sensor is very sensitive to measure the time effects on the bactericidal activity of the three kinds of antibiotics against *E. coli*, and ciprofloxacin has a greater killing effect on *E. coli* than either ceftriaxone or tetracycline under the same conditions, even though there are little structure changes of the bacterial cells at varying incubation times (i.e., the minimum change of the damping resistance signal). The results of FIGS. 26A-26E, Table 5, and FIGS. 27A-27D demonstrate that ciprofloxacin damaged LPS more rapidly and in greater level than that of ceftriaxone and tetracycline. This may be due to their different mechanisms of action. Ciprofloxacin may chelate divalent cations that normally bridge adjacent LPS and phospholipid molecules and stabilize the molecules in the bacterial outer membrane. LPS may become destabilized and ultimately released from the *E. coli* when divalent cation bridges are removed from the outer membrane. So, *E. coli* could not bind to the Con A sensor using LPS as a linker. Ceftriaxone does not interact with divalent cations on the bacterial outer membrane. Instead, ceftriaxone passes through water-filled porin channels in the outer membrane into the periplasmic space and interacts with penicillin binding proteins and finally cause cell lysis. The release of LPS by the ceftriaxone may be the result of fragmentation of the bacteria. Because of the multiple mechanism, ceftriaxone released LPS slower and in lesser amounts than ciprofloxacin in this Example. According to the results in FIGS. 26E and 26F, the similar ΔF changes induced by tetracycline and ceftriaxone indicate that the mechanism of LPS release by tetracycline may be similar to that of ceftriaxone. In most studies dealing with antibiotic-induced LPS release, bioreactive endotoxin has been measured by means of the Limulus amoebocyte lysate (LAL) assay, which involves an enzymatic reaction triggered by the core region of LPS. Endotoxin levels determined by means of the LAL assay therefore reflect not only the concentration of LPS but also the accessibility of the inner core which may be unfolded during exposure to cell-wall active drugs. However, some antibiotics (i.e., aminoglycoside) are known to suppress the LAL reaction, which limits the application of LAL. Reproducible ELISA also can be used to detect LPS. However, antibodies have some limitations such as their production in vivo, limited target analytes, limited shelf lives, and temperature-sensitive to denaturing. A QCM is known to provide a very sensitive mass measuring device and dispense with the time- and cost-demanding labeling step and also eliminates any possible interference of the "true" binding process due to the presence of the labels. In Example 2, the obtained results confirmed feasibility of QCM for promising detection of LPS release. Furthermore, the use of integrated electrochemical measurement in the form of EQCM benefited the reliability of the whole analytical method by providing internal validation of the results.

The minimum inhibitory concentration (MIC), the lowest concentration of an antimicrobial that will inhibit the visible growth of a microorganism after overnight incubation, is generally regarded as the most basic laboratory measurement of the activity of an antimicrobial agent against an organism. The order of antimicrobial activities, (i.e., ciprofloxacin>ceftriaxone>tetracycline) obtained from our lectin biosensor above is consistent with the trend of reported MICs (shown in Table 6).

TABLE 6

Comparison between Previously reported MIC and Example 2 Results

| | Antibiotic | | |
|---|---|---|---|
| | Ceftriaxone* | Ciprofloxacin** | Tetracycline*** |
| Previously Reported Minimum Inhibitory Concentration (MIC, mg/L) | 0.024-0.195 | 0.0075-0.015 | 0.5-4.5 |
| LPS activity Example 2 - susceptibility tests | 27% | 23% | 38% |
| LPS activity Example 2 - real time analysis | 93% | 91% | 95% |
| LPS activity Example 2 - relaxation time | $\tau_{Ciprofloxacin} > \tau_{Ceftriaxone} > \tau_{Tetracycline}$ | | |

*Ceftriaxone: 0.0125-25 mg/L (E. coli (47)), 0.06-8 mg/L (E. coli (305)).
**Ciprofloxacin: 0.015 to 0.002 mg/L (E. coli Neumann) and 0.03 to 0.002 mg/L (E. coli KL16) with increased the pH from 6.0 to 8.0.
***Tetracycline: 0.16 mg/L (ATCC 25923).

As shown in Table 6, MICs of tetracycline are distinctly higher than those of the two antibiotics against different strains. MICs of ciprofloxacin are slightly smaller than those of ceftriaxone. Theoretically, the antimicrobial activity of ceftriaxone is higher than that of ciprofloxacin because of their different antimicrobial mechanisms. The trends of antibiotics bactericidal activity are similar to the reported MICs trends, which also demonstrates that the EQCM method is an efficient method for the determination of MIC.

Conclusions for Example 2

The integrated label free lectin EQCM biosensor was utilized to evaluate the antimicrobial susceptibility of various antibiotics on the basis of quantitatively evaluating the binding between lectin Con A and LPS on the walls of E. coli cells. A measurement of the subsequent unbinding (upon the antibiotic addition causing the release of LPS) made this sensor capable of real time analysis. As noted, three typical kinds of antibiotics were used as models to study the bactericidal activities of antibiotics against E. coli. Measurements were performed both after sample incubation as well as real time to provide the proof of concept. In both the cases, the biosensor demonstrated that all three kinds of antibiotics effectively inhibit the growth of E. coli. However, ciprofloxacin was slightly more active than ceftriaxone against E. coli W1485 with the same concentration, and both ceftriaxone and ciprofloxacin were superior to tetracycline. Variations in antibiotic concentrations and incubation times further elaborated the bactericidal phenomena and enabled the study of the binding kinetics and the relaxation time. This is believed to be a rare example of using a biosensor in this fashion to find out the antibiotic actions, and such studies can form the basis of real time analysis of antibiotic selection, their therapeutic management, and the control over their empiric use that usually gives rise to antibiotic resistance.

Moreover, this sensor can be used to analyze the impact of antibiotic treatment, both for those bacteria that are sensitive to and those that are resistant to the antibiotics. One of the largest drawbacks to use culture in order to detect bacteremia (i.e., bacteria in the blood) in septic patients is that frequently these patients have already been given empiric antibiotics by the time the blood is drawn. The presence of antibiotics in the blood is frequently inhibitory to the growth of pathogens, at times even if the pathogen is resistant to the antibiotic. The reported biosensor can detect the presence of pathogens and identify them in conditions including the presence of antibiotics, which is of even greater value. Going even further, bacteria that have undergone lysis due to antibiotics may still be detectable via this biosensor, as it finds fragments of the bacteria containing the appropriate pili or LPS. Such new dimensions of biosensor based detection can lead to new research efforts toward drug discovery for infectious diseases.

It is to be understood that the ranges provided herein include the stated range and any value or sub-range within the stated range. For example, a range from $2.0 \times 10^3$ cells/mL to $7.0 \times 10^4$ cells/mL should be interpreted to include not only the explicitly recited limits of $2.0 \times 10^3$ cells/mL to $7.0 \times 10^4$ cells/mL, but also to include individual values, such as $2.5 \times 10^3$ cells/mL, $3.0 \times 10^4$ cells/mL, etc., and sub-ranges, such as from $2.25 \times 10^3$ cells/mL to $6.5 \times 10^4$ cells/mL, from $3.0 \times 10^3$ cells/mL to $5.0 \times 10^4$ cells/mL, etc. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:
1. A method for real-time determination of antibiotic effects, the method comprising:
  exposing a surface of a label free biosensor to a sample including a gram-negative bacteria, the label free biosensor including an electrode and a carbohydrate plat- form formed on a surface of the electrode, the carbohydrate platform including:
a conductive polymer;
a quinone moiety attached to the conductive polymer; and
a carbohydrate moiety attached to the quinone moiety;
whereby pili of the gram-negative bacteria binds to the carbohydrate moiety of the carbohydrate platform or a lipopolysaccharide of the gram-negative bacteria binds to a lectin mediator bound to the carbohydrate moiety of the carbohydrate platform;
then allowing a frequency or a current or both the frequency and the current of the biosensor to reach a constant value;
then exposing the surface of the biosensor to an antibiotic;
then measuring i) a frequency change versus time and a damping resistance versus time, or ii) a current versus voltage or the current versus time at a fixed potential, or iii) both i and ii using the biosensor; and
correlating i) the frequency change versus time and the damping resistance versus time, or ii) the current versus voltage or the current versus time at the fixed potential, or iii) both i and ii to an effect of the antibiotic on the gram-negative bacteria.

2. The method as defined in claim 1, further comprising cross-validating the frequency change versus time and the damping resistance versus time measurements with the current versus voltage or the current versus time at the fixed potential measurements.

3. The method as defined in claim 1 wherein the effect of the antibiotic on the gram-negative bacteria is the antibiotic killing the gram-negative bacteria or the antibiotic inhibiting growth of the gram-negative bacteria.

4. The method as defined in claim 1 wherein the correlating includes recognizing that i) the frequency change versus time and the damping resistance versus time, or ii) the current versus voltage or the current versus time at the fixed potential, or iii) both i and ii signals shift in a direction opposite to respective corresponding signals measured after the exposing of the surface of the biosensor to the sample including the gram-negative bacteria.

5. The method as defined in claim 1, further comprising identifying an effective concentration of the antibiotic by measuring the i) the frequency change versus time and the damping resistance versus time, or ii) the current versus voltage or the current versus time at the fixed potential, or iii) both i and ii at different antibiotic concentrations.

6. The method as defined in claim 1, further comprising identifying a response time of the antibiotic by measuring the i) the frequency change versus time and the damping resistance versus time, or ii) the current versus voltage or the current versus time at the fixed potential, or iii) both i and ii at different incubation times.

7. The method as defined in claim 1 wherein the correlating includes recognizing that i) the frequency change versus time and the damping resistance versus time, or ii) the current versus voltage or the current versus time at the fixed potential, or iii) both i and ii signals shift in comparison with a baseline value.

8. A method for end point determination of antibiotic effects, the method comprising:
exposing a surface of a label free biosensor to a sample including a gram-negative bacteria and an antibiotic, the label free biosensor including an electrode and a carbohydrate platform formed on a surface of the electrode, the carbohydrate platform including:
a conductive polymer;
a quinone moiety attached to the conductive polymer; and
a carbohydrate moiety attached to the quinone moiety;
whereby pili of the gram-negative bacteria binds to the carbohydrate moiety of the carbohydrate platform or a lipopolysaccharide of the gram-negative bacteria binds to a lectin mediator bound to the carbohydrate moiety of the carbohydrate platform;
incubating the sample either before or after its exposure to the surface of the label free biosensor; and
measuring any of a frequency, a damping resistance, or an electrochemical signal of the sample using the label free biosensor.

9. The method as defined in claim 8, further comprising:
normalizing i) the frequency of the sample to a frequency obtained for a control sample including the gram-negative bacteria and no antibiotic, or ii) the damping resistance of the sample to a damping resistance obtained for a control sample including the gram-negative bacteria and no antibiotic, or ii) the electrochemical signal of the sample to an electrochemical signal obtained for a control sample including the gram-negative bacteria and no antibiotic to identify a relative signal change of the gram-negative bacteria for a given concentration of the antibiotic; and
determining an effect of the antibiotic on the gram-negative bacteria from the binding percentage.

10. The method as defined in claim 8, further comprising identifying an effect of a length of an incubation time by measuring the any of the frequency, the damping resistance, or the electrochemical signal of the sample at different incubation times.

11. The method as defined in claim 8, further comprising identifying an effect of a concentration of the antibiotic by measuring the any of the frequency, the damping resistance, or the electrochemical signal of the sample at different antibiotic concentrations.

12. The method as defined in claim 11, further comprising determining a dosage of the antibiotic for treating the gram-negative bacteria from the any of the frequency, the damping resistance, or the electrochemical signal measurements at different antibiotic concentrations.

13. A method for label free detection of gram-negative bacteria, comprising,
exposing a surface of a label free biosensor to a sample including a gram-negative bacteria, the label free biosensor including an electrode and a carbohydrate platform formed on a surface of the electrode, the carbohydrate platform including:
a conductive polymer;
a quinone moiety attached to the conductive polymer; and
a carbohydrate moiety attached to the quinone moiety;
whereby pili of the gram-negative bacteria binds to the carbohydrate moiety of the carbohydrate platform or a lipopolysaccharide of the gram-negative bacteria binds to a lectin mediator bound to the carbohydrate moiety of the carbohydrate platform; and
measuring any of a frequency, a damping resistance, or an electrochemical signal of the sample using the label free biosensor.

14. The method as defined in claim 13, further comprising quantifying a concentration of the gram-negative bacteria using calibrations based on a quantitative relationship of the frequency, the damping resistance, or the electrochemical signal versus concentration linear regression fitting curves.

15. The method as defined in claim 13 wherein prior to the exposing of the surface of the label free biosensor to the sample including the gram-negative bacteria, the method further comprises exposing the surface of a label free biosensor to a solution including a lectin mediator.

16. A label free biosensor, comprising:
an electrode; and
a carbohydrate platform formed on a surface of the electrode, the carbohydrate platform including:
a conductive polymer;
a quinone moiety attached to the conductive polymer; and
a carbohydrate moiety attached to the quinone moiety.

17. The label free biosensor as defined in claim 16, further comprising a lectin mediator attached to the carbohydrate moiety.

18. The label free biosensor as defined in claim 17 wherein the lectin mediator is selected from the group consisting of *Anguilla anguilla, Artocarpus integrifolia, Bauhinia purpurea, Canavalia ensiformis, Dolichos biflorus, Datura stramonium, Erythrina cristagalli, Galanthus nivalis, Griffonia simplicifolia*-I, *Griffonia simplicifolia*-II, *Helix pomatia, Lens culinaris, Lotus tetragonolobus, Maackia amurensis, Persea Americana, Arachis hypogaea, Glycine max, Sambucus nigra, Solanum tuberosum, Ulex europaeus*-I, and *Triticum vulgare*.

19. The label free biosensor as defined in claim 16 wherein:
the conductive polymer is selected from the group consisting of polythiophene, polypyrrole, polyaniline, poly(para-phenylene), poly(indole), poly(thienylene-vinylene), poly(furylene-vinylene), poly(phenylene-vinylene), poly(fluorene), polyvinyl ferrocene and polypyridine; and
the carbohydrate moiety is selected from the group consisting of D-(+)-mannose (Man), methyl α-D-mannopyranoside (MeMan), D-(+)-glucose (Glc), D-(+)-galactose (Gal), lactose, acetylglycosamine, 2-O-α-D-mannopyranosyl-D-mannopyranose (Man2), 3,6-di-O-(α-D-mannopyranosyl)-D-mannopyranose, Galα1-3Gal oligosaccharides, fucosylated oligosaccharides, gangliosides, and sialylated oligosaccharides.

20. The label free biosensor as defined in claim 16 wherein:
the conductive polymer is polythiophene;
the carbohydrate moiety is a thiol-modified mannose; and
the biosensor further comprises a lectin confined to the thiol-modified mannose.

21. The label free biosensor as defined in claim 16 wherein the electrode is an electrode of a quartz crystal microbalance.

* * * * *